US012805796B2

(12) United States Patent
Kariv et al.

(10) Patent No.: US 12,805,796 B2
(45) Date of Patent: Nov. 24, 2026

(54) INITIALIZING MEDICAL DEVICES

(71) Applicant: Itamar Medical Ltd., Caesarea (IL)

(72) Inventors: Itay Kariv, Caesarea (IL); Michael Pasternak, Caesarea (IL)

(73) Assignee: Itamar Medical Ltd., Caesarea (IL)

( * ) Notice: Subject to any disclaimer, the term of this patent is extended or adjusted under 35 U.S.C. 154(b) by 219 days.

(21) Appl. No.: 18/587,088

(22) Filed: Feb. 26, 2024

(65) Prior Publication Data

US 2024/0285229 A1 Aug. 29, 2024

Related U.S. Application Data

(60) Provisional application No. 63/448,817, filed on Feb. 28, 2023.

(51) Int. Cl.

| | |
|---|---|
| ***A61B 5/00*** | (2006.01) |
| ***A61B 5/0205*** | (2006.01) |
| ***G16H 40/67*** | (2018.01) |
| *A61B 5/024* | (2006.01) |
| *A61B 5/113* | (2006.01) |

(52) U.S. Cl.

CPC .......... *A61B 5/4818* (2013.01); *A61B 5/0002* (2013.01); *A61B 5/0205* (2013.01); *G16H 40/67* (2018.01); *A61B 5/02438* (2013.01); *A61B 5/113* (2013.01); *A61B 2560/029* (2013.01)

(58) Field of Classification Search

CPC ............ A61B 2560/029; A61B 5/0002; A61B 5/0205; A61B 5/02438; A61B 5/113; A61B 5/4818; A61B 5/6826; G16H 40/67

See application file for complete search history.

(56) References Cited

U.S. PATENT DOCUMENTS

| | | | | |
|---|---|---|---|---|
| 5,891,023 | A * | 4/1999 | Lynn | A61B 7/003 600/323 |
| 6,319,205 | B1 | 11/2001 | Goor et al. | |
| 6,461,305 | B1 | 10/2002 | Schnall | |
| 8,639,240 | B2 | 1/2014 | Romine et al. | |
| 10,193,721 | B2 | 1/2019 | Huomo | |
| 2003/0204213 | A1 * | 10/2003 | Jensen | A61B 5/0538 607/17 |
| 2004/0215095 | A1 * | 10/2004 | Lee | A61B 5/14551 600/324 |
| 2005/0181839 | A1 | 8/2005 | Tiainen et al. | |
| 2011/0218409 | A1 * | 9/2011 | Kugler | A61B 7/003 600/301 |
| 2014/0351832 | A1 * | 11/2014 | Cho | H04L 67/141 719/328 |

OTHER PUBLICATIONS

ZzzPAT For Watch-PAT Software Operation Manual, Itamar Medical Ltd., REF OM2197434, copyright 2022, 146 pages.

* cited by examiner

*Primary Examiner* — Amanda K Hulbert

(74) *Attorney, Agent, or Firm* — The Webb Law Firm

(57) ABSTRACT

Systems and methods can initialize medical devices. The system includes an external programming device configured to: transmit a voltage-based index value through a wired connection to an uninitialized medical device of the plurality of uninitialized medical devices, wherein the voltage-based index value identifies the external programming device; and establish a wireless connection between the external programming device and the uninitialized medical device based on the voltage-based index value.

13 Claims, 37 Drawing Sheets

INITIALIZING MEDICAL DEVICES

CROSS-REFERENCE TO RELATED APPLICATIONS

This application claims priority under 35 U.S.C. § 119(e) to U.S. Provisional Patent Application Ser. No. 63/448,817, filed Feb. 28, 2023 and titled INITIALIZING MEDICAL DEVICES, the entirety of which is hereby incorporated by reference herein.

Embodiments of the current disclosure are directed toward initializing of medical devices.

BACKGROUND OF THE DISCLOSURE

Sleep disordered breathing (SDB) refers to a wide spectrum of sleep-related conditions such as apnea, hypopnea, hyperpnea, central sleep apnea, obstructive sleep apnea, mixed sleep apnea, airway obstruction, hypoxemia, sleep disruption, etc. For example, sleep apnea is an affliction in which breathing repeatedly stops when a person is sleeping, and hypopnea is an affliction in which breathing repeatedly becomes reduced (e.g., shallow breathing, reduced airflow, and/or the like) when a person is sleeping. These serious sleep disorders can be associated with an elevated risk for certain heart conditions that can be fatal if left untreated.

Home and/or remote sleep apnea tests (e.g., HSATs) and/or home and/or remote sleep disordered breathing (SDB) tests may be used to diagnose sleep apnea. Such HSAT devices may include a worn device that is provided to a patient, where measurements are performed when the patient is sleeping in the comfort of the patient's own bed. For example, HSAT worn devices may include worn photoplethysmography (PPG) devices, such as wrist-worn smart watches and/or the like, which may include one or more PPG sensors.

In the event that sleep apnea is diagnosed, a medical device may be provided for treating sleep apnea. The medical device may be provided to a patient such that treatment is performed when the patient is sleeping in the comfort of the patient's own bed. For example, sleep apnea treatment devices may use nasal Continuous Positive Airway Pressure (CPAP) therapy to treat obstructive sleep apnea or an implantable phrenic nerve stimulator to treat central sleep apnea.

When HSAT devices and/or the like are available from the factory or after manufacturing, they need to be initialized before they are deployed in the field.

SUMMARY

Embodiments of the current disclosure include systems, devices, products, apparatus, and/or methods for initializing medical devices.

According to some non-limiting embodiments or aspects, provided is a programming system for initializing a plurality of uninitialized medical devices that are patient-wearable, including: an external programming device configured to initialize an uninitialized medical device of the plurality of uninitialized medical devices by: transmitting a voltage-based index value through a wired connection to an uninitialized medical device of the plurality of uninitialized medical devices, wherein the voltage-based index value identifies the external programming device; and establishing a wireless connection between the external programming device and the uninitialized medical device based on the voltage-based index value.

In some non-limiting embodiments or aspects, the uninitialized medical device includes a sleep apnea diagnostic or treatment device, the sleep apnea diagnostic or treatment device including: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of sleep data based on the one or more physiological signals.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the non-volatile memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

In some non-limiting embodiments or aspects, the external programming device includes index generation circuitry, the index generation circuitry configured to generate the voltage-based index value as a voltage signal based on a predetermined input to the index generation circuitry.

In some non-limiting embodiments or aspects, the external programming device includes a user interface configured to receive a user input and produce the predetermined input to the index generation circuitry based on the user input.

In some non-limiting embodiments or aspects, the index generation circuitry is configured to generate the voltage-based index value as the voltage signal by generating the voltage signal as a predetermined supply voltage associated with the voltage-based index value.

In some non-limiting embodiments or aspects, the index generation circuitry is configured to generate the voltage-based index value as the voltage signal by generating the voltage signal as varying voltages between two predefined voltage levels to encode the voltage-based index value in the voltage signal.

In some non-limiting embodiments or aspects, the voltage-based index value is encoded in the voltage signal as a binary sequence of bits.

In some non-limiting embodiments or aspects, the external programming device includes a square wave generator configured to generate the voltage signal as the varying voltages between the two predefined voltage levels as a changing square wave pulse train in which the voltage-based index value is encoded.

In some non-limiting embodiments or aspects, the wired connection to the uninitialized medical device includes a pair of electrical battery terminals of the uninitialized medical device.

In some non-limiting embodiments or aspects, the external programming device includes a battery adapter including a pair of electrical adapter terminals configured to connect to the pair of electrical battery terminals of the uninitialized medical device.

In some non-limiting embodiments or aspects, the uninitialized medical device includes voltage receiving circuitry connected to the pair of electrical battery terminals, wherein the voltage receiving circuitry is configured to: receive the voltage signal; determine, based on the voltage signal, a binary sequence of bits; and store, in a buffer, the binary sequence of bits.

In some non-limiting embodiments or aspects, the uninitialized medical device further includes at least one processor coupled to a memory, wherein the at least one processor is configured to: read, from the buffer, the binary sequence of bits; and determine, based on the binary sequence of bits, the voltage-based index value that identifies the external programming device.

In some non-limiting embodiments or aspects, in response to receiving the voltage signal via the wired connection, the uninitialized medical device is configured to: operate in a first mode in response to a voltage of the voltage signal being within a first voltage range; and operate in a second mode different than the first mode in response to the voltage of the voltage signal being within a second voltage range higher than and disjoint of the first voltage range.

In some non-limiting embodiments or aspects, the first voltage range is between about 1.6 V and about 3.3 V, and wherein the voltage of the voltage signal is within the first voltage range.

In some non-limiting embodiments or aspects, the voltage-based index value uniquely identifies the external programming device among a plurality of external programming devices.

In some non-limiting embodiments or aspects, the uninitialized medical device includes a sleep apnea diagnostic or treatment device, the sleep apnea diagnostic or treatment device including: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of the sleep data.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

In some non-limiting embodiments or aspects, the external programming device is configured to: transmit, via the wireless connection between the external programming device and the uninitialized medical device, a unique medical device identifier to the uninitialized medical device that causes the uninitialized medical device to be uniquely addressable.

In some non-limiting embodiments or aspects, the wireless connection includes at least one of the following: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, or any combination thereof.

In some non-limiting embodiments or aspects, the external programming device is configured to establish the wireless connection between the external programming device and the uninitialized medical device based on the voltage-based index value in response to receiving a wireless connection request from the uninitialized medical device, wherein the wireless connection request includes the voltage-based index value.

In some non-limiting embodiments or aspects, the external programming device is configured to: program, via the wireless connection between the external programming device and the uninitialized medical device, one or more monitoring and/or treatment parameters and/or thresholds of the uninitialized medical device for use in operation of the uninitialized medical device.

In some non-limiting embodiments or aspects, the one or more monitoring and/or treatment parameters and/or thresholds include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

In some non-limiting embodiments or aspects, the external programming device is configured to: receive, via the wireless connection between the external programming device and the uninitialized medical device, a result of one or more hardware and/or software tests executed by the uninitialized medical device, wherein the one or more hardware and/or software tests include a test of hardware and/or software associated with at least one of the following: an LED operation; a photodiode operation; a DC-DC Component; a battery; a flash memory integrity; an actigraphy sensor; a chest motion sensor; or any combination thereof.

In some non-limiting embodiments or aspects, the uninitialized medical device includes a sleep apnea diagnostic or treatment device, the sleep apnea diagnostic or treatment device including: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of the sleep data.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

According to some non-limiting embodiments or aspects, provided is an uninitialized medical device, including: one or more physiological sensors configured to be bodily-attached to a patient and sense physiological signals from the patient over a period of time; medical device wireless communications circuitry configured to transmit data based on the sensed one or more physiological signals from the patient over the period of time; and at least one processor coupled to a memory and configured to: receive, via a wired connection with an external programming device, a voltage-based index value that identifies the external programming device; and control the wireless communications circuitry to establish a wireless connection between the external programming device and the uninitialized medical device based on the voltage-based index value.

In some non-limiting embodiments or aspects, the uninitialized medical device includes a sleep apnea diagnostic or treatment device, wherein the one or more physiological sensors are configured to sense the one or more physiological signals from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

In some non-limiting embodiments or aspects, the at least one processor is configured to receive, via the wired connection with the external programming device, the voltage-based index value that identifies the external programming device via a voltage signal voltage signal transmitted by the external programming device through the wired connection.

In some non-limiting embodiments or aspects, the external programming device includes index generation circuitry, the index generation circuitry configured to generate the voltage-based index value as the voltage signal based on a predetermined input to the index generation circuitry.

In some non-limiting embodiments or aspects, the external programming device includes a user interface configured to receive a user input and produce the predetermined input to the index generation circuitry based on the user input.

In some non-limiting embodiments or aspects, the index generation circuitry is configured to generate the voltage-based index value as the voltage signal by generating the voltage signal as a predetermined supply voltage associated with the voltage-based index value.

In some non-limiting embodiments or aspects, the index generation circuitry is configured to generate the voltage-based index value as the voltage signal by generating the voltage signal as varying voltages between two predefined voltage levels to encode the voltage-based index value in the voltage signal.

In some non-limiting embodiments or aspects, the voltage-based index value is encoded in the voltage signal as a binary sequence of bits.

In some non-limiting embodiments or aspects, the external programming device includes a non-sinusoidal square wave generator configured to generate the voltage signal as the varying voltages between the two predefined voltage levels as a changing square wave pulse train in which the voltage-based index value is encoded.

In some non-limiting embodiments or aspects, the wired connection to the uninitialized medical device includes a pair of electrical battery terminals of the uninitialized medical device.

In some non-limiting embodiments or aspects, the external programming device includes a battery adapter including a pair of electrical adapter terminals configured to connect to the pair of electrical battery terminals of the uninitialized medical device.

In some non-limiting embodiments or aspects, the voltage signal includes a predetermined supply voltage associated with the voltage-based index value.

In some non-limiting embodiments or aspects, the voltage signal includes varying voltages between two predefined voltage levels by which the voltage-based index value is encoded in the voltage signal.

In some non-limiting embodiments or aspects, the wired connection with the external programming device includes a pair of electrical battery terminals of the uninitialized medical device.

In some non-limiting embodiments or aspects, the external programming device includes a battery adapter including a pair of electrical adapter terminals configured to connect to the pair of electrical battery terminals of the uninitialized medical device.

In some non-limiting embodiments or aspects, the uninitialized medical device further includes: voltage receiving circuitry connected to the pair of electrical battery terminals, wherein the voltage receiving circuitry is configured to: receive the voltage signal; determine, based on the voltage signal, a binary sequence of bits; and store, in a buffer, the binary sequence of bits.

In some non-limiting embodiments or aspects, the at least one processor is further configured to: read, from the buffer, the binary sequence of bits; and determine, based on the binary sequence of bits, the voltage-based index value that identifies the external programming device.

In some non-limiting embodiments or aspects, in response to receiving the voltage signal via the wired connection, the at least one processor is configured to: operate in a first mode in response to a voltage of the voltage signal being within a first voltage range; and operate in a second mode different than the first mode in response to the voltage of the voltage signal being within a second voltage range higher than and disjoint of the first voltage range.

In some non-limiting embodiments or aspects, the first voltage range is between about 1.6 V and about 3.3 V, and wherein the voltage of the voltage signal is within the first voltage range.

In some non-limiting embodiments or aspects, the voltage-based index value uniquely identifies the external programming device among a plurality of external programming devices.

In some non-limiting embodiments or aspects, the uninitialized medical device includes a sleep apnea diagnostic or treatment device, wherein the one or more physiological signals are sensed from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

In some non-limiting embodiments or aspects, the at least one processor is configured to: receive, via the wireless connection between the external programming device and the uninitialized medical device, a unique medical device identifier that causes the uninitialized medical device to be uniquely addressable.

In some non-limiting embodiments or aspects, the wireless connection includes at least one of the following: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, or any combination thereof.

In some non-limiting embodiments or aspects, the at least one processor is configured to control the medical device wireless communications circuitry to transmit a wireless connection request including the voltage-based index value to the external programming device to establish the wireless connection between the external programming device and the uninitialized medical device.

In some non-limiting embodiments or aspects, the at least one processor is configured to: store, in the non-volatile memory, the unique medical device identifier to initialize the uninitialized medical device by causing the uninitialized medical device to be uniquely addressable.

In some non-limiting embodiments or aspects, the at least one processor is configured to: receive, via the wireless connection between the external programming device and the uninitialized medical device, one or more monitoring and/or treatment parameters and/or thresholds of the uninitialized medical device for use in operation of the uninitialized medical device.

In some non-limiting embodiments or aspects, the one or more monitoring and/or treatment parameters and/or thresholds include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

In some non-limiting embodiments or aspects, the at least one processor is configured to: execute one or more hardware and/or software tests; and transmit, via the wireless connection between the external programming device and the uninitialized medical device, a result of the one or more hardware and/or software tests, wherein the one or more hardware and/or software tests include a test of hardware and/or software associated with at least one of the following: an LED operation; a photodiode operation; a DC-DC Component; a battery; a flash memory integrity; an actigraphy sensor; a chest motion sensor; or any combination thereof.

In some non-limiting embodiments or aspects, the uninitialized medical device includes a sleep apnea diagnostic or treatment device, wherein the one or more physiological signals are sensed from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

In some non-limiting embodiments or aspects, the one or more physiological sensors includes a photoplethysmography (PPG) sensor configured to be bodily-attached to a portion of the patient's body and sense an arterial pulse of the patient.

In some non-limiting embodiments or aspects, the one or more physiological sensors is configured to apply a substantially uniform subdiastolic pressure to a portion of the patient's body while sensing an arterial pulse as a peripheral arterial signal of the patient.

In some non-limiting embodiments or aspects, the one or more physiological sensors includes a finger probe including a pneumo-optical sensor.

In some non-limiting embodiments or aspects, the one or more portions of the patient's body includes one or more of a finger of the patient, a wrist of the patient, a toe of the patient, a lower arm of the patient, an upper arm of the patient, and/or a hand of the patient.

In some non-limiting embodiments or aspects, the pneumo-optical sensor includes a PPG sensor configured to be utilized in conjunction with a pressure device configured to apply the uniform subdiastolic pressure to the portion of the patient's body.

In some non-limiting embodiments or aspects, the pneumo-optical sensor is configured to apply the uniform subdiastolic pressure to a distal two-thirds of the finger and fingertip of the patient's finger.

In some non-limiting embodiments or aspects, the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

In some non-limiting embodiments or aspects, the sleep apnea diagnostic or treatment device includes a wrist-worn device, wherein the wrist-worn device includes the medical device wireless communications circuitry and the at least one processor coupled to the memory.

In some non-limiting embodiments or aspects, the sleep apnea diagnostic or treatment device includes a finger probe, wherein the finger probe includes the medical device wireless communications circuitry and the at least one processor coupled to the memory.

In some non-limiting embodiments or aspects, the one or more physiological sensors includes a chest motion sensor configured to be disposed on an upper chest area of the patient, the chest motion sensor including one or more of a snoring microphone and an accelerometer.

In some non-limiting embodiments or aspects, the one or more physiological sensors includes one or more of ECG electrodes and a body impedance sensor.

In some non-limiting embodiments or aspects, the sleep apnea diagnostic or treatment device includes a system-on-chip (SoC) that includes the medical device wireless communications circuitry and the at least one processor coupled to the memory.

According to some non-limiting embodiments or aspects, provided is an uninitialized medical device, including: one or more physiological sensors configured to be bodily-attached to one or more portions of a patient's body and sense one or more physiological signals from the patient over a period of time; medical device wireless communications circuitry configured to transmit data based on the sensed one or more physiological signals from the patient over the period of time; and at least one processor coupled to a memory and configured to: receive, via a non-wired connection using the one or more physiological sensors, from an external programming device, an index value that identifies the external programming device; and control the medical device wireless communications circuitry to establish a wireless connection between the external programming device and the uninitialized medical device based on the index value.

In some non-limiting embodiments or aspects, the one or more physiological sensors comprise at least one of the following: a microphone configured to receive the index value that identifies the external programming device via an audio signal; an optical sensor configured to receive the index value that identifies the external programming device via an optical signal; a pressure transducer configured to receive the index value that identifies the external programming device via a pressure signal; an accelerometer configured to receive the index value that identifies the external programming device via at least one of vibration of the uninitialized medical device, modification of an orientation of the uninitialized medical device, or any combination thereof; or any combination thereof.

In some non-limiting embodiments or aspects, the uninitialized medical device includes a sleep apnea diagnostic or treatment device, wherein the one or more physiological sensors are configured to sense the one or more physiological signals from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

In some non-limiting embodiments or aspects, the at least one processor is configured to: receive, via the wireless connection between the external programming device and the uninitialized medical device, a unique medical device identifier that causes the uninitialized medical device to be uniquely addressable.

According to some non-limiting embodiments or aspects, provided is a programming system for initializing a plurality of uninitialized medical devices that are patient-wearable, including: an external programming device configured to: transmit, an index value through a non-wired connection to one or more physiological sensors of an uninitialized medical device of the plurality of uninitialized medical devices, wherein the one or more physiological sensors % are configured to be bodily-attached to one or more portions of the patient's body and sense one or more physiological signals from the patient over a period of time, and wherein the index value identifies the external programming device; and establish a wireless connection between the external programming device and the uninitialized medical device based on the voltage-based index value.

In some non-limiting embodiments or aspects, the external programming device comprises at least one of the following: a speaker configured to generate the index value that identifies the external programming device as an audio output; an optical emitter configured to generate the index value that identifies the external programming device as an optical signal; a pressure generator configured to generate the index value that identifies the external programming device as a pressure applied to the uninitialized medical device; a vibrator configured to generate the index value that identifies the external programming device as a vibration signal; a serial or parallel manipulator robot configured to generate the index value that identifies the external programming device as a modification of an orientation of the uninitialized medical device; or any combination thereof.

In some non-limiting embodiments or aspects, the uninitialized medical device comprises a sleep apnea diagnostic or treatment device, the sleep apnea diagnostic or treatment device including: the one or more physiological sensors; medical device wireless communications circuitry configured to transmit sleep data based on the sensed one or more physiological signals from the patient over the period of time; and at least one processor coupled to a memory configured to: control acquisition of the one or more physiological signals from the one or more physiological sensors; and/or control the transmission of sleep data based on the one or more physiological signals.

According to some non-limiting embodiments or aspects, provided is an uninitialized medical device, including: an accelerometer configured to be bodily-attached to a patient's body and sense an orientation of the patient's body over a period of time; medical device wireless communications circuitry configured to transmit data based on the sensed orientation of the patient's body over the period of time; and at least one processor coupled to a memory and configured to: receive, via the accelerometer, from an external programming device, an orientation change-based index value that identifies the external programming device; and control the medical device wireless communications circuitry to establish a wireless connection between the external programming device and the uninitialized medical device based on the orientation change-based index value.

According to some non-limiting embodiments or aspects, provided is an uninitialized medical device, including: an optical sensor including photodiode configured to be bodily-attached to a patient's body and sense a light intensity for determining an oxygen saturation and/or pulse rate of the patient over a period of time; medical device wireless communications circuitry configured to transmit data based on the sensed light intensity from the patient over the period of time; and at least one processor coupled to a memory and configured to: receive, via the photodiode, from an external programming device, a light-based index value that identifies the external programming device; and control the medical device wireless communications circuitry to establish a wireless connection between the external programming device and the uninitialized medical device based on the light-based index value.

According to some non-limiting embodiments or aspects, provided is an uninitialized medical device, including: a chest sensor including a microphone configured to be bodily-attached to a patient's chest and sense an audio signal for determining a snoring sound of the patient over a period of time; medical device wireless communications circuitry configured to transmit data based on the sensed audio signal from the patient over the period of time; and at least one processor coupled to a memory and configured to: receive, via the microphone, from an external programming device, an audio-based index value that identifies the external programming device; and control the medical device wireless communications circuitry to establish a wireless connection between the external programming device and the uninitialized medical device based on the audio-based index value.

According to some non-limiting embodiments or aspects, provided is an uninitialized medical device, including: a finger probe including a pressure transducer configured to be bodily-attached to a patient's finger and sense a pressure signal for determining a pressure applied to the patient's finger; medical device wireless communications circuitry configured to transmit data based on the sensed pressure signal from the patient over the period of time; and at least one processor coupled to a memory and configured to: receive, via the pressure transducer, from an external programming device, a pressure-based index value that identifies the external programming device; and control the medical device wireless communications circuitry to establish a wireless connection between the external programming device and the uninitialized medical device based on the pressure-based index value.

Further embodiments or aspects are set forth in the following numbered clauses:

Clause 1. A programming system for initializing a plurality of uninitialized medical devices that are patient-wearable, comprising: an external programming device configured to initialize an uninitialized medical device of the plurality of uninitialized medical devices by: transmitting a voltage-based index value through a wired connection to an uninitialized medical device of the plurality of uninitialized medical devices, wherein the voltage-based index value identifies the external programming device; and establishing a wireless connection between the external programming device and the uninitialized medical device based on the voltage-based index value.

Clause 2. The programming system of clause 1, wherein the uninitialized medical device comprises a sleep apnea diagnostic or treatment device, the sleep apnea diagnostic or treatment device comprising: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of sleep data based on the one or more physiological signals.

Clause 3. The programming system of any of clauses 1 or 2, wherein the one or more physiological sensors comprises a photoplethysmography (PPG) sensor configured to be bodily-attached to a portion of the patient's body and sense an arterial pulse of the patient.

Clause 4. The programming system of any of clauses 1-3, wherein the one or more physiological sensors is configured to apply a substantially uniform subdiastolic pressure to a portion of the patient's body while sensing an arterial pulse as a peripheral arterial signal of the patient.

Clause 5. The programming system of any of clauses 1-4, wherein the one or more physiological sensors comprises a finger probe comprising a pneumo-optical sensor.

Clause 6. The programing system of any of clauses 1-5, wherein the one or more portions of the patient's body comprises one or more of a finger of the patient, a wrist of the patient, a toe of the patient, a lower arm of the patient, an upper arm of the patient, and/or a hand of the patient.

Clause 7. The programming system of any of clauses 1-6, wherein the pneumo-optical sensor comprises a PPG sensor configured to be utilized in conjunction with a pressure device configured to apply the uniform subdiastolic pressure to the portion of the patient's body.

Clause 8. The programming system of any of clauses 1-7, wherein the pneumo-optical sensor is configured to apply the uniform subdiastolic pressure to a distal two-thirds of the finger and fingertip of the patient's finger.

Clause 9. The programming system of any of clauses 1-8, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 10. The programming system of any of clauses 1-9, wherein the sleep apnea diagnostic or treatment device comprises a wrist-worn device, wherein the wrist-worn device includes the medical device wireless communications circuitry and the at least one processor coupled to the non-volatile memory.

Clause 11. The programming system of any of clauses 1-10, wherein the sleep apnea diagnostic or treatment device comprises a finger probe, wherein the finger probe comprises the medical device wireless communications circuitry and the at least one processor coupled to the memory.

Clause 12. The programming system of any of clauses 1-11, wherein the one or more physiological sensors comprises a chest motion sensor configured to be disposed on an upper chest area of the patient, the chest motion sensor comprising one or more of a snoring microphone and an accelerometer.

Clause 13. The programming system of any of clauses 1-12, wherein the one or more physiological sensors comprises one or more of ECG electrodes and a body impedance sensor.

Clause 14. The programming system of any of clauses 1-13, wherein the sleep apnea diagnostic or treatment device includes a system-on-chip (SoC) that includes the medical device wireless communications circuitry and the at least one processor coupled to the memory.

Clause 15. The programming system of any of clauses 1-14, wherein the external programming device comprises index generation circuitry, the index generation circuitry configured to generate the voltage-based index value as a voltage signal based on a predetermined input to the index generation circuitry.

Clause 16. The programming system of any of clauses 1-15, wherein the external programming device comprises a user interface configured to receive a user input and produce the predetermined input to the index generation circuitry based on the user input.

Clause 17. The programming system of any of clauses 1-16, wherein the index generation circuitry is configured to generate the voltage-based index value as the voltage signal by generating the voltage signal as a predetermined supply voltage associated with the voltage-based index value.

Clause 18. The programming system of any of clauses 1-17, wherein the index generation circuitry is configured to generate the voltage-based index value as the voltage signal by generating the voltage signal as varying voltages between two predefined voltage levels to encode the voltage-based index value in the voltage signal.

Clause 19. The programming system of any of clauses 1-18, wherein the voltage-based index value is encoded in the voltage signal as a binary sequence of bits.

Clause 20. The programming system of any of clauses 1-19, wherein the external programming device includes a square wave generator configured to generate the voltage signal as the varying voltages between the two predefined voltage levels as a changing square wave pulse train in which the voltage-based index value is encoded.

Clause 21. The programming system of any of clauses 1-20, wherein the wired connection to the uninitialized medical device includes a pair of electrical battery terminals of the uninitialized medical device.

Clause 22. The programming system of any of clauses 1-21, wherein the external programming device includes a battery adapter including a pair of electrical adapter terminals configured to connect to the pair of electrical battery terminals of the uninitialized medical device.

Clause 23. The programming system of any of clauses 1-22, wherein the uninitialized medical device includes voltage receiving circuitry connected to the pair of electrical battery terminals, wherein the voltage receiving circuitry is configured to: receive the voltage signal; determine, based on the voltage signal, a binary sequence of bits; and store, in a buffer, the binary sequence of bits.

Clause 24. The programming system of any of clauses 1-23, wherein the uninitialized medical device further includes at least one processor coupled to a memory, wherein the at least one processor is configured to: read, from the buffer, the binary sequence of bits; and determine, based on the binary sequence of bits, the voltage-based index value that identifies the external programming device.

Clause 25. The programming system of any of clauses 1-24, wherein, in response to receiving the voltage signal via the wired connection, the uninitialized medical device is configured to: operate in a first mode in response to a voltage of the voltage signal being within a first voltage range; and operate in a second mode different than the first mode in response to the voltage of the voltage signal being within a second voltage range higher than and disjoint of the first voltage range.

Clause 26. The programming system of any of clauses 1-25, wherein the first voltage range is between about 1.6 V and about 3.3 V, and wherein the voltage of the voltage signal is within the first voltage range.

Clause 27. The programming system of any of clauses 1-26, wherein the voltage-based index value uniquely identifies the external programming device among a plurality of external programming devices.

Clause 28. The programming system of any of clauses 1-27, wherein the uninitialized medical device comprises a sleep apnea diagnostic or treatment device, the sleep apnea diagnostic or treatment device comprising: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of the sleep data.

Clause 29. The programming system of any of clauses 1-28, wherein the one or more physiological sensors comprises a photoplethysmography (PPG) sensor configured to be bodily-attached to a portion of the patient's body and sense an arterial pulse of the patient.

Clause 30. The programming system of any of clauses 1-29, wherein the one or more physiological sensors is configured to apply a substantially uniform subdiastolic pressure to a portion of the patient's body while sensing an arterial pulse as a peripheral arterial signal of the patient.

Clause 31. The programming system of any of clauses 1-30, wherein the one or more physiological sensors comprises a finger probe comprising a pneumo-optical sensor.

Clause 32. The programing system of any of clauses 1-31, wherein the one or more portions of the patient's body comprises one or more of a finger of the patient, a wrist of the patient, a toe of the patient, a lower arm of the patient, an upper arm of the patient, and/or a hand of the patient.

Clause 33. The programming system of any of clauses 1-32, wherein the pneumo-optical sensor comprises a PPG sensor configured to be utilized in conjunction with a pressure device configured to apply the uniform subdiastolic pressure to the portion of the patient's body.

Clause 34. The programming system of any of clauses 1-33, wherein the pneumo-optical sensor is configured to apply the uniform subdiastolic pressure to a distal two-thirds of the finger and fingertip of the patient's finger.

Clause 35. The programming system any of clauses 1-34, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 36. The programming system of any of clauses 1-35, wherein the sleep apnea diagnostic or treatment device comprises a wrist-worn device, wherein the wrist-worn device includes the medical device wireless communications circuitry and the at least one processor coupled to the memory.

Clause 37. The programming system of any of clauses 1-36, wherein the sleep apnea diagnostic or treatment device comprises a finger probe, wherein the finger probe comprises the medical device wireless communications circuitry and the at least one processor coupled to the memory.

Clause 38. The programming system of any of clauses 1-37, wherein the one or more physiological sensors comprises a chest motion sensor configured to be disposed on an upper chest area of the patient, the chest motion sensor comprising one or more of a snoring microphone and an accelerometer.

Clause 39. The programming system of any of clauses 1-38, wherein the one or more physiological sensors comprises one or more of ECG electrodes and a body impedance sensor.

Clause 40. The programming system of any of clauses 1-39, wherein the sleep apnea diagnostic or treatment device includes a system-on-chip (SoC) that includes the medical device wireless communications circuitry and the at least one processor coupled to the memory.

Clause 41. The programming system of any of clauses 1-40, wherein the external programming device is configured to: transmit, via the wireless connection between the external programming device and the uninitialized medical device, a unique medical device identifier to the uninitialized medical device that causes the uninitialized medical device to be uniquely addressable.

Clause 42. The programming system of any of clauses 1-41, wherein the wireless connection includes at least one of the following: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, or any combination thereof.

Clause 43. The programming system of any of clauses 1-42, wherein the external programming device is configured to establish the wireless connection between the external programming device and the uninitialized medical device based on the voltage-based index value in response to receiving a wireless connection request from the uninitialized medical device, wherein the wireless connection request includes the voltage-based index value.

Clause 44. The programming system of any of clauses 1-43, wherein the external programming device is configured to: program, via the wireless connection between the external programming device and the uninitialized medical device, one or more monitoring and/or treatment parameters and/or thresholds of the uninitialized medical device for use in operation of the uninitialized medical device.

Clause 45. The programming system of any of clauses 1-44, wherein the one or more monitoring and/or treatment parameters and/or thresholds include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

Clause 46. The programming system of any of clauses 1-45, wherein the external programming device is configured to: receive, via the wireless connection between the external programming device and the uninitialized medical device, a result of one or more hardware and/or software tests executed by the uninitialized medical device, wherein the one or more hardware and/or software tests include a test of hardware and/or software associated with at least one of the following: an LED operation; a photodiode operation; a DC-DC Component; a battery; a flash memory integrity; an actigraphy sensor; a chest motion sensor; or any combination thereof.

Clause 47. The programming system of any of clauses 1-46, wherein the uninitialized medical device comprises a sleep apnea diagnostic or treatment device, the sleep apnea diagnostic or treatment device comprising: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory configured to: control acquisition of the one or more physiological signals from the one or more physiological sensors; and/or control the transmission of the sleep data.

Clause 48. The programming system of any of clauses 1-47, wherein the one or more physiological sensors comprises a photoplethysmography (PPG) sensor configured to be bodily-attached to a portion of the patient's body and sense an arterial pulse of the patient.

Clause 49. The programming system of any of clauses 1-48, wherein the one or more physiological sensors is configured to apply a substantially uniform subdiastolic pressure to a portion of the patient's body while sensing an arterial pulse as a peripheral arterial signal of the patient.

Clause 50. The programming system of any of clauses 1-49, wherein the one or more physiological sensors comprises a finger probe comprising a pneumo-optical sensor.

Clause 51. The programing system of any of clauses 1-50, wherein the one or more portions of the patient's body comprises one or more of a finger of the patient, a wrist of the patient, a toe of the patient, a lower arm of the patient, an upper arm of the patient, and/or a hand of the patient.

Clause 52. The programming system of any of clauses 1-51, wherein the pneumo-optical sensor comprises a PPG sensor configured to be utilized in conjunction with a pressure device configured to apply the uniform subdiastolic pressure to the portion of the patient's body.

Clause 53. The programming system of any of clauses 1-52, wherein the pneumo-optical sensor is configured to apply the uniform subdiastolic pressure to a distal two-thirds of the finger and fingertip of the patient's finger.

Clause 54. The programming system of any of clauses 1-53, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 55. The programming system of any of clauses 1-54, wherein the sleep apnea diagnostic or treatment device comprises a wrist-worn device, wherein the wrist-worn device includes the medical device wireless communications circuitry and the at least one processor coupled to the memory.

Clause 56. The programming system of any of clauses 1-55, wherein the sleep apnea diagnostic or treatment device comprises a finger probe, wherein the finger probe comprises the medical device wireless communications circuitry and the at least one processor coupled to the memory.

Clause 57. The programming system of any of clauses 1-56, wherein the one or more physiological sensors comprises a chest motion sensor configured to be disposed on an upper chest area of the patient, the chest motion sensor comprising one or more of a snoring microphone and an accelerometer.

Clause 58. The programming system of any of clauses 1-57, wherein the one or more physiological sensors comprises one or more of ECG electrodes and a body impedance sensor.

Clause 59. The programming system of any of clauses 1-58, wherein the sleep apnea diagnostic or treatment device includes a system-on-chip (SoC) that includes the medical device wireless communications circuitry and the at least one processor coupled to the memory.

Clause 60. An uninitialized medical device, comprising: one or more physiological sensors configured to be bodily-attached to a patient and sense physiological signals from the patient over a period of time; medical device wireless communications circuitry configured to transmit data based on the sensed one or more physiological signals from the patient over the period of time; and at least one processor coupled to a memory and configured to: receive, via a wired connection with an external programming device, a voltage-based index value that identifies the external programming device; and control the wireless communications circuitry to establish a wireless connection between the external programming device and the uninitialized medical device based on the voltage-based index value.

Clause 61. The uninitialized medical device of clause 60, wherein the uninitialized medical device includes a sleep apnea diagnostic or treatment device, wherein the one or more physiological sensors are configured to sense the one or more physiological signals from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

Clause 62. The uninitialized medical device of any of clauses 60 or 61, wherein the one or more physiological sensors comprises a photoplethysmography (PPG) sensor configured to be bodily-attached to a portion of the patient's body and sense an arterial pulse of the patient.

Clause 63. The uninitialized medical device of any of clauses 60-62, wherein the one or more physiological sensors is configured to apply a substantially uniform subdiastolic pressure to a portion of the patient's body while sensing an arterial pulse as a peripheral arterial signal of the patient.

Clause 64. The uninitialized medical device of any of clauses 60-63, wherein the one or more physiological sensors comprises a finger probe comprising a pneumo-optical sensor.

Clause 65. The uninitialized medical device of any of clauses 60-64, wherein the one or more portions of the patient's body comprises one or more of a finger of the patient, a wrist of the patient, a toe of the patient, a lower arm of the patient, an upper arm of the patient, and/or a hand of the patient.

Clause 66. The uninitialized medical device of any of clauses 60-65, wherein the pneumo-optical sensor comprises a PPG sensor configured to be utilized in conjunction with a pressure device configured to apply the uniform subdiastolic pressure to the portion of the patient's body.

Clause 67. The uninitialized medical device of any of clauses 60-66, wherein the pneumo-optical sensor is configured to apply the uniform subdiastolic pressure to a distal two-thirds of the finger and fingertip of the patient's finger.

Clause 68. The uninitialized medical device of any of clauses 60-67, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 69. The uninitialized medical device of any of clauses 60-68, wherein the sleep apnea diagnostic or treatment device comprises a wrist-worn device, wherein the wrist-worn device includes the medical device wireless communications circuitry and the at least one processor coupled to the memory.

Clause 70. The uninitialized medical device of any of clauses 60-69, wherein the sleep apnea diagnostic or treatment device comprises a finger probe, wherein the finger probe comprises the medical device wireless communications circuitry and the at least one processor coupled to the memory.

Clause 71. The uninitialized medical device of any of clauses 60-70, wherein the one or more physiological sensors comprises a chest motion sensor configured to be disposed on an upper chest area of the patient, the chest motion sensor comprising one or more of a snoring microphone and an accelerometer.

Clause 72. The uninitialized medical device of any of clauses 60-71, wherein the one or more physiological sensors comprises one or more of ECG electrodes and a body impedance sensor.

Clause 73. The uninitialized medical device of any of clauses 60-72, wherein the sleep apnea diagnostic or treatment device includes a system-on-chip (SoC) that includes the medical device wireless communications circuitry and the at least one processor coupled to the memory.

Clause 74. The uninitialized medical device of any of clauses 60-73, wherein the at least one processor is configured to receive, via the wired connection with the external programming device, the voltage-based index value that identifies the external programming device via a voltage signal voltage signal transmitted by the external programming device through the wired connection.

Clause 75. The uninitialized medical device of any of clauses 60-74, wherein the external programming device comprises index generation circuitry, the index generation circuitry configured to generate the voltage-based index value as the voltage signal based on a predetermined input to the index generation circuitry.

Clause 76. The uninitialized medical device of any of clauses 60-75, wherein the external programming device comprises a user interface configured to receive a user input and produce the predetermined input to the index generation circuitry based on the user input.

Clause 77. The uninitialized medical device of any of clauses 60-76, wherein the index generation circuitry is configured to generate the voltage-based index value as the voltage signal by generating the voltage signal as a predetermined supply voltage associated with the voltage-based index value.

Clause 78. The uninitialized medical device of any of clauses 60-77, wherein the index generation circuitry is configured to generate the voltage-based index value as the voltage signal by generating the voltage signal as varying voltages between two predefined voltage levels to encode the voltage-based index value in the voltage signal.

Clause 79. The uninitialized medical device of any of clauses 60-78, wherein the voltage-based index value is encoded in the voltage signal as a binary sequence of bits.

Clause 80. The uninitialized medical device of any of clauses 60-79, wherein the external programming device includes a non-sinusoidal square wave generator configured to generate the voltage signal as the varying voltages between the two predefined voltage levels as a changing square wave pulse train in which the voltage-based index value is encoded.

Clause 81. The uninitialized medical device of any of clauses 60-80, wherein the wired connection to the uninitialized medical device includes a pair of electrical battery terminals of the uninitialized medical device.

Clause 82. The uninitialized medical device of any of clauses 60-81, wherein the external programming device includes a battery adapter including a pair of electrical adapter terminals configured to connect to the pair of electrical battery terminals of the uninitialized medical device.

Clause 83. The uninitialized medical device of any of clauses 60-82, wherein the voltage signal includes a predetermined supply voltage associated with the voltage-based index value.

Clause 84. The uninitialized medical device of any of clauses 60-83, wherein the voltage signal includes varying voltages between two predefined voltage levels by which the voltage-based index value is encoded in the voltage signal.

Clause 85. The uninitialized medical device of any of clauses 60-84, wherein the wired connection with the external programming device includes a pair of electrical battery terminals of the uninitialized medical device.

Clause 86. The uninitialized medical device of any of clauses 60-85, wherein the external programming device includes a battery adapter including a pair of electrical adapter terminals configured to connect to the pair of electrical battery terminals of the uninitialized medical device.

Clause 87. The uninitialized medical device of any of clauses 60-86, further comprising: voltage receiving circuitry connected to the pair of electrical battery terminals, wherein the voltage receiving circuitry is configured to: receive the voltage signal; determine, based on the voltage signal, a binary sequence of bits; and store, in a buffer, the binary sequence of bits.

Clause 88. The uninitialized medical device of any of clauses 60-87, wherein the at least one processor is further configured to: read, from the buffer, the binary sequence of bits; and determine, based on the binary sequence of bits, the voltage-based index value that identifies the external programming device.

Clause 89. The uninitialized medical device any of clauses 60-88, wherein, in response to receiving the voltage signal via the wired connection, the at least one processor is configured to: operate in a first mode in response to a voltage of the voltage signal being within a first voltage range; and operate in a second mode different than the first mode in response to the voltage of the voltage signal being within a second voltage range higher than and disjoint of the first voltage range.

Clause 90. The uninitialized medical device of any of clauses 60-89, wherein the first voltage range is between about 1.6 V and about 3.3 V, and wherein the voltage of the voltage signal is within the first voltage range.

Clause 91. The uninitialized medical device of any of clauses 60-90, wherein the voltage-based index value uniquely identifies the external programming device among a plurality of external programming devices.

Clause 92. The uninitialized medical device of any of clauses 60-91, wherein the uninitialized medical device includes a sleep apnea diagnostic or treatment device, wherein the one or more physiological signals are sensed from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

Clause 93. The uninitialized medical device of any of clauses 60-92, wherein the one or more physiological sensors comprises a photoplethysmography (PPG) sensor configured to be bodily-attached to a portion of the patient's body and sense an arterial pulse of the patient.

Clause 94. The uninitialized medical device of any of clauses 60-93, wherein the one or more physiological sensors is configured to apply a substantially uniform subdiastolic pressure to a portion of the patient's body while sensing an arterial pulse as a peripheral arterial signal of the patient.

Clause 95. The uninitialized medical device of any of clauses 60-94, wherein the one or more physiological sensors comprises a finger probe comprising a pneumo-optical sensor.

Clause 96. The uninitialized medical device of any of clauses 60-95, wherein the one or more portions of the patient's body comprises one or more of a finger of the patient, a wrist of the patient, a toe of the patient, a lower arm of the patient, an upper arm of the patient, and/or a hand of the patient.

Clause 97. The uninitialized medical device of any of clauses 60-96, wherein the pneumo-optical sensor comprises a PPG sensor configured to be utilized in conjunction with a pressure device configured to apply the uniform subdiastolic pressure to the portion of the patient's body.

Clause 98. The uninitialized medical device of any of clauses 60-97, wherein the pneumo-optical sensor is configured to apply the uniform subdiastolic pressure to a distal two-thirds of the finger and fingertip of the patient's finger.

Clause 99. The uninitialized medical device of any of clauses 60-98, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 100. The uninitialized medical device of any of clauses 60-99, wherein the sleep apnea diagnostic or treatment device comprises a wrist-worn device, wherein the wrist-worn device includes the medical device wireless communications circuitry and the at least one processor coupled to the memory.

Clause 101. The uninitialized medical device of any of clauses 60-100, wherein the sleep apnea diagnostic or treatment device comprises a finger probe, wherein the finger probe comprises the medical device wireless communications circuitry and the at least one processor coupled to the memory.

Clause 102. The uninitialized medical device of any of clauses 60-101, wherein the one or more physiological sensors comprises a chest motion sensor configured to be disposed on an upper chest area of the patient, the chest motion sensor comprising one or more of a snoring microphone and an accelerometer.

Clause 103. The uninitialized medical device of any of clauses 60-102, wherein the one or more physiological sensors comprises one or more of ECG electrodes and a body impedance sensor.

Clause 104. The uninitialized medical device of any of clauses 60-103, wherein the sleep apnea diagnostic or treatment device includes a system-on-chip (SoC) that includes the medical device wireless communications circuitry and the at least one processor coupled to the memory.

Clause 105. The uninitialized medical device of any of clauses 60-104, wherein the at least one processor is configured to: receive, via the wireless connection between the external programming device and the uninitialized medical device, a unique medical device identifier that causes the uninitialized medical device to be uniquely addressable.

Clause 106. The uninitialized medical device of any of clauses 60-105, wherein the wireless connection includes at least one of the following: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, or any combination thereof.

Clause 107. The uninitialized medical device of any of clauses 60-106, wherein the at least one processor is configured to control the medical device wireless communications circuitry to transmit a wireless connection request including the voltage-based index value to the external programming device to establish the wireless connection between the external programming device and the uninitialized medical device.

Clause 108. The uninitialized medical device of any of clauses 60-107, wherein the at least one processor is configured to: store, in the non-volatile memory, the unique medical device identifier to initialize the uninitialized medical device by causing the uninitialized medical device to be uniquely addressable.

Clause 109. The uninitialized medical device of any of clauses 60-108, wherein the at least one processor is configured to: receive, via the wireless connection between the external programming device and the uninitialized medical device, one or more monitoring and/or treatment parameters and/or thresholds of the uninitialized medical device for use in operation of the uninitialized medical device.

Clause 110. The uninitialized medical device of any of clauses 60-109, wherein the one or more monitoring and/or treatment parameters and/or thresholds include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

Clause 111. The uninitialized medical device of any of clauses 60-110, wherein the at least one processor is configured to: execute one or more hardware and/or software tests; and transmit, via the wireless connection between the external programming device and the uninitialized medical device, a result of the one or more hardware and/or software tests, wherein the one or more hardware and/or software tests include a test of hardware and/or software associated with at least one of the following: an LED operation; a photodiode operation; a DC-DC Component; a battery; a flash memory integrity; an actigraphy sensor; a chest motion sensor; or any combination thereof.

Clause 112. The uninitialized medical device of any of clauses 60-111, wherein the uninitialized medical device includes a sleep apnea diagnostic or treatment device, wherein the one or more physiological signals are sensed from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

Clause 113. The uninitialized medical device of any of clauses 60-112, wherein the one or more physiological sensors comprises a photoplethysmography (PPG) sensor configured to be bodily-attached to a portion of the patient's body and sense an arterial pulse of the patient.

Clause 114. The uninitialized medical device of any of clauses 60-113, wherein the one or more physiological sensors is configured to apply a substantially uniform subdiastolic pressure to a portion of the patient's body while sensing an arterial pulse as a peripheral arterial signal of the patient.

Clause 115. The uninitialized medical device of any of clauses 60-114, wherein the one or more physiological sensors comprises a finger probe comprising a pneumo-optical sensor.

Clause 116. The uninitialized medical device of any of clauses 60-115, wherein the one or more portions of the patient's body comprises one or more of a finger of the patient, a wrist of the patient, a toe of the patient, a lower arm of the patient, an upper arm of the patient, and/or a hand of the patient.

Clause 117. The uninitialized medical device of any of clauses 60-116, wherein the pneumo-optical sensor comprises a PPG sensor configured to be utilized in conjunction with a pressure device configured to apply the uniform subdiastolic pressure to the portion of the patient's body.

Clause 118. The uninitialized medical device of any of clauses 60-117, wherein the pneumo-optical sensor is configured to apply the uniform subdiastolic pressure to a distal two-thirds of the finger and fingertip of the patient's finger.

Clause 119. The uninitialized medical device of any of clauses 60-118, wherein the uniform subdiastolic pressure is configured to one or more of: clamp the finger probe to the patient's finger; facilitate unloading of arterial wall tension; facilitate increase in a dynamic range of a peripheral arterial signal of the patient relative to PPG signals without the uniform subdiastolic pressure; and/or mitigate distal venous pooling or distention to avoid induction of venoarterial-mediated vasoconstriction.

Clause 120. The uninitialized medical device of any of clauses 60-119, wherein the sleep apnea diagnostic or treatment device comprises a wrist-worn device, wherein the wrist-worn device includes the medical device wireless communications circuitry and the at least one processor coupled to the memory.

Clause 121. The uninitialized medical device of any of clauses 60-120, wherein the sleep apnea diagnostic or treatment device comprises a finger probe, wherein the finger probe comprises the medical device wireless communications circuitry and the at least one processor coupled to the memory.

Clause 122. The uninitialized medical device of any of clauses 60-121, wherein the one or more physiological sensors comprises a chest motion sensor configured to be disposed on an upper chest area of the patient, the chest motion sensor comprising one or more of a snoring microphone and an accelerometer.

Clause 123. The uninitialized medical device of any of clauses 60-122, wherein the one or more physiological sensors comprises one or more of ECG electrodes and a body impedance sensor.

Clause 124. The uninitialized medical device of any of clauses 60-123, wherein the sleep apnea diagnostic or treatment device includes a system-on-chip (SoC) that includes the medical device wireless communications circuitry and the at least one processor coupled to the memory.

Clause 125. An uninitialized medical device, comprising: one or more physiological sensors configured to be bodily-attached to one or more portions of a patient's body and sense one or more physiological signals from the patient over a period of time; medical device wireless communications circuitry configured to transmit data based on the sensed one or more physiological signals from the patient over the period of time; and at least one processor coupled to a memory and configured to: receive, via a non-wired connection using the one or more physiological sensors, from an external programming device, an index value that identifies the external programming device; and control the medical device wireless communications circuitry to establish a wireless connection between the external programming device and the uninitialized medical device based on the index value.

Clause 126. The uninitialized medical device of clause 125, wherein the one or more physiological sensors comprise at least one of the following: a microphone configured to receive the index value that identifies the external programming device via an audio signal; an optical sensor configured to receive the index value that identifies the external programming device via an optical signal; a pressure transducer configured to receive the index value that identifies the external programming device via a pressure signal; an accelerometer configured to receive the index value that identifies the external programming device via at least one of vibration of the uninitialized medical device, modification of an orientation of the uninitialized medical device, or any combination thereof; or any combination thereof.

Clause 127. The uninitialized medical device of any of clauses 125 or 126, wherein the uninitialized medical device includes a sleep apnea diagnostic or treatment device, wherein the one or more physiological sensors are configured to sense the one or more physiological signals from the patient during sleep over the period of time, wherein the data includes sleep data based on the one or more physiological signals sensed from the patient during sleep over the period of time, and wherein the at least one processor is further configured to: control acquisition of the one or more physiological signals from the one or more physiological sensors; and/or control the transmission of the sleep data.

Clause 128. The uninitialized medical device of any of clauses 125-127, wherein the at least one processor is configured to: receive, via the wireless connection between the external programming device and the uninitialized medical device, a unique medical device identifier that causes the uninitialized medical device to be uniquely addressable.

Clause 129. A programming system for initializing a plurality of uninitialized medical devices that are patient-wearable, comprising: an external programming device configured to: transmit, an index value through a non-wired connection to one or more physiological sensors of an uninitialized medical device of the plurality of uninitialized medical devices, wherein the one or more physiological sensors are configured to be bodily-attached to one or more portions of the patient's body and sense one or more physiological signals from the patient over a period of time, and wherein the index value identifies the external programming device; and establish a wireless connection between the external programming device and the uninitialized medical device based on the voltage-based index value.

Clause 130. The programming system of clause 129, wherein the external programming device comprises at least one of the following: a speaker configured to generate the index value that identifies the external programming device as an audio output; an optical emitter configured to generate the index value that identifies the external programming device as an optical signal; a pressure generator configured to generate the index value that identifies the external programming device as a pressure applied to the uninitialized medical device; a vibrator configured to generate the index value that identifies the external programming device as a vibration signal; a serial or parallel manipulator robot configured to generate the index value that identifies the external programming device as a modification of an orientation of the uninitialized medical device; or any combination thereof.

Clause 131. The programming system of any of clauses 129 or 130, wherein the uninitialized medical device comprises a sleep apnea diagnostic or treatment device, the sleep apnea diagnostic or treatment device comprising: the one or more physiological sensors; medical device wireless communications circuitry configured to transmit sleep data based on the sensed one or more physiological signals from the patient over the period of time; and at least one processor coupled to a memory configured to: control acquisition of the one or more physiological signals from the one or more physiological sensors; and/or control the transmission of sleep data based on the one or more physiological signals.

Clause 132. An uninitialized medical device, comprising: an accelerometer configured to be bodily-attached to a patient's body and sense an orientation of the patient's body over a period of time; medical device wireless communications circuitry configured to transmit data based on the sensed orientation of the patient's body over the period of time; and at least one processor coupled to a memory and configured to: receive, via the accelerometer, from an external programming device, an orientation change-based index value that identifies the external programming device; and control the medical device wireless communications circuitry to establish a wireless connection between the external programming device and the uninitialized medical device based on the orientation change-based index value.

Clause 133. An uninitialized medical device, comprising: an optical sensor including photodiode configured to be bodily-attached to a patient's body and sense a light intensity for determining an oxygen saturation and/or pulse rate of the patient over a period of time; medical device wireless communications circuitry configured to transmit data based on the sensed light intensity from the patient over the period of time; and at least one processor coupled to a memory and configured to: receive, via the photodiode, from an external programming device, a light-based index value that identifies the external programming device; and control the medical device wireless communications circuitry to establish a wireless connection between the external programming device and the uninitialized medical device based on the light-based index value.

Clause 134. An uninitialized medical device, comprising: a chest sensor including a microphone configured to be bodily-attached to a patient's chest and sense an audio signal for determining a snoring sound of the patient over a period of time; medical device wireless communications circuitry configured to transmit data based on the sensed audio signal from the patient over the period of time; and at least one processor coupled to a memory and configured to: receive, via the microphone, from an external programming device, an audio-based index value that identifies the external programming device; and control the medical device wireless communications circuitry to establish a wireless connection between the external programming device and the uninitialized medical device based on the audio-based index value.

Clause 135. An uninitialized medical device, comprising: a finger probe including a pressure transducer configured to be bodily-attached to a patient's finger and sense a pressure signal for determining a pressure applied to the patient's finger; medical device wireless communications circuitry configured to transmit data based on the sensed pressure signal from the patient over the period of time; and at least one processor coupled to a memory and configured to: receive, via the pressure transducer, from an external programming device, a pressure-based index value that identifies the external programming device; and control the medical device wireless communications circuitry to establish a wireless connection between the external programming device and the uninitialized medical device based on the pressure-based index value.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the . . . drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
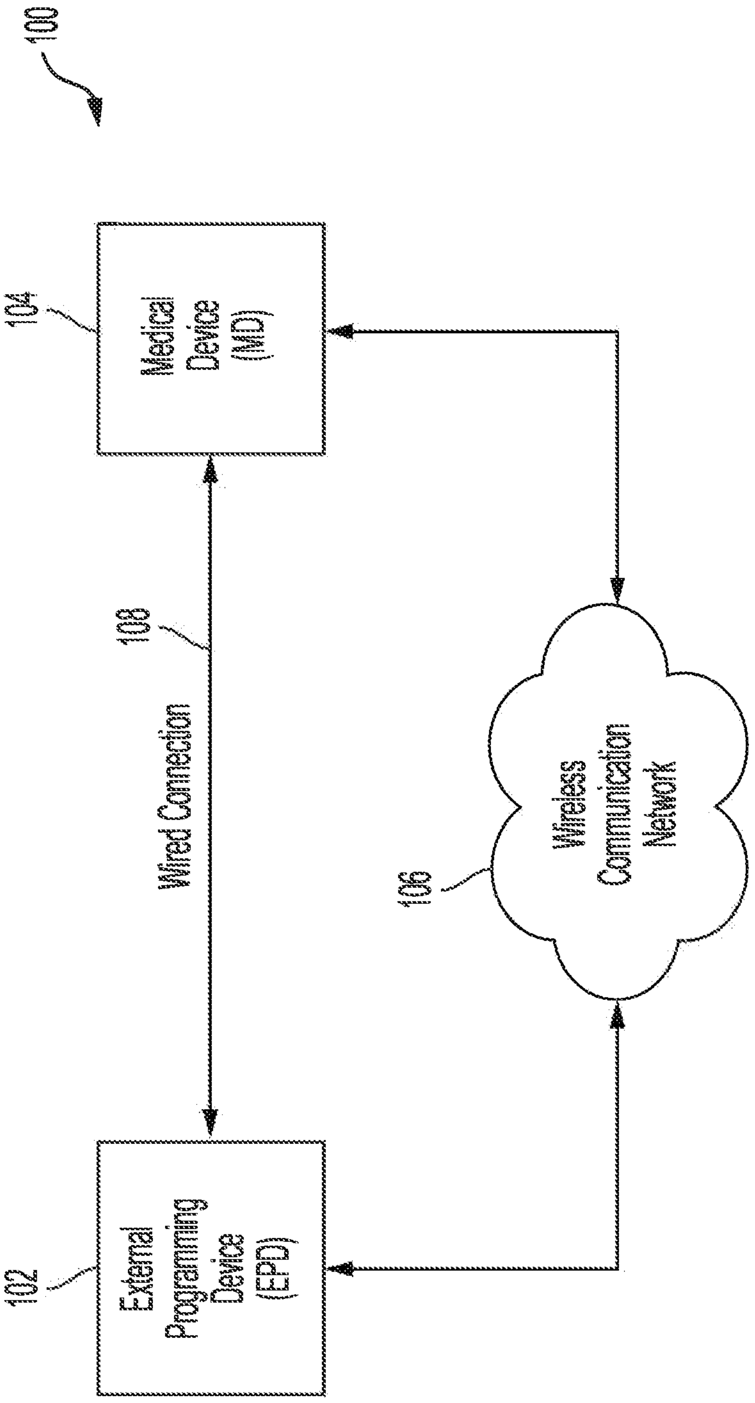
FIGS. 1A and 1B show example block diagrams of a system for initializing medical devices, according to some embodiments.

This disclosure relates to techniques, systems, and devices for initializing wearable medical devices. For example, the wearable medical devices can be pre-programmed or pre-configured before being deployed in the field. Wearable medical devices can be configured to be worn for a predetermined monitoring period, e.g., a study period during which one or more physiological signals of the patient are being monitored. Wearable medical devices can be configured to be worn for a predetermined protection period, e.g., a period of time during which the patient is being protected against an underlying medical condition. For example, the wearable medical device can be worn by, e.g., having all or a portion of the device be physically attached to a portion of the body of the patient for the monitoring or protection period, e.g., for an extended period of time, such as a full night of sleep, and/or the like. Wearable medical devices as described herein include devices for home and/or remote sleep apnea tests (e.g., HSATs) and/or home and/or remote sleep disordered breathing (SDB) tests. In example scenarios, a wearable medical device is provided to a patient, and measurements are performed when the patient is sleeping in the comfort of the patient's own bed. For example, an HSAT wearable device may include a sensor for measuring a PPG signal and/or a peripheral arterial signal, e.g., through the application of a pressure field on the portion of the patient's body to which the sensor is attached. For example, such a sensor may be part of a finger probe. In examples, HSATs may provide a more limited set of physiological signals and measurements than a polysomnography (PSG) study. It is desirable to make less burdensome the initial pre-programming of equipment required for a sleep study such as HSAT or remote or home-based SDB testing so that manufacturing, set up, and configuration of such devices can be performed without extension training, skill, or professional technical intervention. Embodiments herein provide improvements in this regard.

Sleep apnea is a common sleep disorder that affects millions of people. With this condition, a person may have an interruption in their breathing while sleeping that occurs through repetitive pauses or apneic events. There are several types of sleep apnea, of which two prominent types include obstructive sleep apnea (OSA) and central sleep apnea (CSA). CSA can be characterized by pauses in breathing due to a lack of respiratory effort during sleep. Unlike OSA, the pauses in breathing throughout the night may be due to the lack of respiratory muscles activating or the brain failing to cause the respiratory muscles to activate. CSA can often be characterized as Cheyne-Stokes Respiration (CSR) in heart failure (HF) patients, and is a common comorbidity, affecting 30-50% of patients with reduced left ventricular ejection fraction (LVEF) and up to 18-30% of patients with preserved LVEF. Untreated CSA has shown to be independently associated with increased mortality and hospitalizations, especially in patients with heart failure. The symptoms of sleep apnea-fatigue, daytime somnolence, shortness of breath, and nocturnal dyspnea-often overlap with those of heart failure, making it difficult to evaluate the effect of cardiovascular therapies on patient symptoms while the sleep apnea remains untreated.

Clinicians are commonly presented with complaints of fatigue and problems sleeping. Understanding who to systematically screen and test can be challenging. In addition, heart failure clinicians need to be aware of treatment options for their patients as they may differ from the best options for other sleep apnea patients.

OSA may result from the muscles in the upper airway relaxing or collapsing during sleep, narrowing the breathing passage, and impeding airflow. While OSA is substantially more prevalent than CSA in the general population it is often the focus of the majority of sleep-disordered breathing diagnostic and treatment efforts. However, the two types of apnea may be nearly equally represented in heart failure, where CSA affects approximately 40% of patients and OSA approximately 36% of patients. The 2017 ACC/AHA/HFSA guidelines recognize the "clinical necessity to distinguish obstructive versus central sleep apnea" in patients with heart failure.

Medical devices including sleep apnea diagnostic or treatment devices may be initialized or configured before being assigned and/or provided to a patient for diagnostic or treatment purposes. For example, after being assembled, an uninitialized medical device may be programmed with a unique medical device identifier (e.g., by burning-in a unique serial number into the medical device to give the medical device its "identity", etc.), programmed with one or more parameters and/or thresholds for use in operation of the medical device, and/or caused to execute and provide a result of one or more hardware and/or software tests to ensure proper function of the medical device, before the medical device is assigned and/or provided to a patient. As an example, uninitialized medical devices may be initialized or configured by a manufacturer or other authorized entity in a production assembly line, a factory setting, or a repair facility, and/or by a provider (e.g., a doctor, a nurse, etc.) in a care facility or office.

Some medical devices may not include an accessible data port (e.g., a Universal Serial Bus (USB) port, etc.). For example, in order to keep device cost low and/or minimize access points for cyber-attacks, the use of input peripherals or ports may be reduced or eliminated. However, a lack of an accessible data port may increase a complexity of an initialization or configuration process of these medical devices. For example, even though the uninitialized devices may have built-in wireless communications capability, such uninitialized devices may not be able to communicate without initial configuration information, such as a unique medical device identifier or other information used by, e.g., an onboard microcontroller with an embedded Bluetooth radio (such as a Bluetooth system-on-chip (SoC)).

In implementations, an external programming device may be configured to initialize a single medical device at a time. In examples, multiple external programming devices may be used to program multiple uninitialized medical devices concurrently or in parallel to reduce the programming time, which may be significantly greater if only a single external programming device were to be used to program the multiple programming devices in a serial manner. For example, multiple uninitialized medical devices may be initialized or configured concurrently or in parallel at a same location by multiple external programming devices by establishing wireless connections between the uninitialized medical devices and the external programming devices. In such an example scenario, an initialization or configuration to be programmed by a particular external programming device may be related to individual characteristics (e.g., previously measured sensor parameters, a predetermined unique identifier, etc.) of a specific uninitialized medical device. There is therefore a need to ensure that the specific uninitialized medical device wirelessly connects to the particular external programming device that is configured to program the individual characteristics for that specific medical device. As an example, at a location including multiple external programming devices, there may be a different network identifier (e.g., a different Bluetooth address, a different Wi-Fi service set identifier (SSID), etc.) broadcast by each external programming device (and/or other wireless devices at the location), for example, such that a wireless signal from each external programming device is received by the specific uninitialized medical device. As such, the specific uninitialized medical device may not know which of the multiple external programming devices is the particular external programming device to wirelessly connect to for initialization and subsequent programming of the individual characteristics for that specific medical device. In this way, there is a need for uninitialized medical devices to distinguish or differentiate between multiple external programming devices and/or their associated wireless communication networks to facilitate the concurrent or in parallel initialization and subsequent programming of the multiple uninitialized medical devices in an individualized manner.

Accordingly, this disclosure relates to systems, devices, methods, and computer program products for initializing medical devices. For example, a programming system for initializing a plurality of uninitialized medical devices that are patient-wearable may include an external programming device configured to transmit an index value (e.g., a voltage-based index value through a wired connection, etc.) to an uninitialized medical device of the plurality of uninitialized medical devices. The index value may identify the external programming device (e.g., uniquely identify the external programming device among a plurality of external programming devices). In this way, the external programming device may be identified as the particular external programming device to wirelessly connect to for initializing and subsequently programming individual characteristics for that specific medical device. For example, the external programming device may establish a wireless connection between the external programming device and the uninitialized medical device based on the index value.

As another example, an uninitialized medical device may include one or more physiological sensors configured to be bodily-attached to a patient and sense physiological signals from the patient over a period of time. The uninitialized medical device can include medical device wireless communications circuitry configured to transmit data based on the sensed one or more physiological signals from the patient over the period of time, and, in some implementations, at least one processor that can be coupled to a memory. The at least one processor may be configured to receive (e.g., via a wired connection with an external programming device, etc.) an index value, e.g., in some implementations, a voltage-based index value, that is configured to identify the external programming device. For example, the voltage-based index value may be configured to be coded into a voltage signal as described in further detail below. In this way, the uninitialized medical device may know the identity of which external programming device to wirelessly connect to for receiving the individual characteristics for that specific medical device. For example, the at least one processor may be configured to control the wireless communications circuitry to establish a wireless connection between the external programming device and the uninitialized medical device based on the index value.

In some embodiments, the external programming device includes index generation circuitry configured to generate the index value. In examples, the index value can be transmitted optically or via a mechanical transfer mechanism as detailed further below. Turning to voltage based index generation, for example, the index value is generated as a voltage signal based on a predetermined input to the index generation circuitry. The at least one processor of the uninitialized medical device may be configured to receive, via the wired connection with the external programming device, the index value that identifies the external programming device via the voltage signal transmitted by the external programming device through the wired connection. For example, the external programming device includes a user interface configured to receive a user input and produce the predetermined input to the index generation circuitry based on the user input. The index generation circuitry is configured to generate the voltage-based index value as the voltage signal by generating the voltage signal as a predetermined supply voltage associated with the voltage-based index value and/or by generating the voltage signal as varying voltages between two predefined voltage levels to encode the voltage-based index value in the voltage signal (e.g., as a binary sequence). In this way, the external programming device may identify itself to the uninitialized medical device as the particular external programming device to wirelessly connect to for initializing and subsequently programming the individual characteristics of that specific medical device.

In some embodiments, the wired connection to the uninitialized medical device may include a pair of electrical battery terminals of the uninitialized medical device, and the external programming device may include a battery adapter including a pair of electrical adapter terminals configured to connect to the pair of electrical battery terminals of the uninitialized medical device. Additionally, the uninitialized medical device may include voltage receiving circuitry connected to the pair of electrical battery terminals. As such, the voltage receiving circuitry may be configured to receive the voltage signal, determine, based on the voltage signal, a binary sequence of bits, and store, in a buffer, the binary sequence of bits. As such, the at least one processor of the uninitialized medical device may be configured to read, from the buffer, the binary sequence of bits, and determine, based on the binary sequence of bits, the voltage-based index value that identifies the external programming device. In this way, the voltage-based index value that identifies the particular external programming device for initializing and subsequently programming individual characteristics for that specific medical device may be provided to an uninitialized medical device that lacks an accessible data port.

In some embodiments, in response to receiving the voltage signal via the wired connection, the uninitialized medical device may be configured to operate in a first mode (e.g., an initialization mode, a pre-programming mode, a production mode, or other such mode configured for initializing the uninitialized medical device) in response to a voltage of the voltage signal being within a first voltage range (e.g., voltage-based index is within a first voltage range), and operate in a second mode (e.g., a diagnostic or treatment mode, a normal operation mode, or the like) different than the first mode in response to the voltage of the voltage signal being within a second voltage range higher than and disjoint of the first voltage range. For example, the voltage-based index can include a first voltage range of between about 1.6 V and about 3.3 V. The voltage of the voltage signal representing the voltage-based index can be within the first voltage range. In this way, the uninitialized medical device may know, based on the voltage range of the voltage signal whether to look for and/or use the voltage-based index value.

The index value may be stored in a local device buffer of the uninitialized medical device. The uninitialized medical device may load the index value from the local device buffer for wireless advertising (e.g., for Bluetooth or BLE advertising, etc.). For example, the uninitialized medical device may transmit the index value on one or more advertising channels (e.g., one or more BLE channels, etc.). The external programming device may receive the index value on the one or more advertising channels (e.g., the one or more BLE channels, etc.). The external programming device can send a response packet indicating that the external programming device is prepared to establish a BLE connection if the index value is correct and corresponds to an uninitialized medical device that is authorized to connect to the external programming device. The uninitialized medical device may receive the response packet and, assuming the uninitialized medical device receives a legitimate response packet, the uninitialized medical device can connect to the external programming device via BLE on one of the data channels.

In some embodiments, the at least one processor of the uninitialized medical device may be configured to control the medical device wireless communications circuitry to transmit a wireless connection request including the voltage-based index value to the external programming device to establish the wireless connection between the external programming device and the uninitialized medical device, and the external programming device may be configured to establish the wireless connection between the external programming device and the uninitialized medical device based on the voltage-based index value in response to receiving the wireless connection request including the voltage-based index value from the uninitialized medical device. In such an example, the wireless connection may include at least one of the following: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, or any combination thereof. In this way, the uninitialized medical device may be wirelessly connected to the particular external programming device for wirelessly programming the individual characteristics for that specific medical device.

In some embodiments, the external programming device may be configured to transmit, via the wireless connection between the external programming device and the uninitialized medical device, a unique medical device identifier to the uninitialized medical device that causes the uninitialized medical device to be uniquely addressable, and the at least one processor of the uninitialized medical device may be configured to receive, via the wireless connection between the external programming device and the uninitialized medical device, the unique medical device identifier that causes the uninitialized medical device to be uniquely addressable. As such, the at least one processor may store, in the memory, the unique medical device identifier to initialize the uninitialized medical device by causing the uninitialized medical device to be uniquely addressable.

In some embodiments, the external programming device may be configured to program, via the wireless connection between the external programming device and the uninitialized medical device, one or more monitoring and/or treatment parameters and/or thresholds of the uninitialized medical device for use in operation of the uninitialized medical device. For example, the at least one processor of the uninitialized medical device may be configured to receive, via the wireless connection between the external programming device and the uninitialized medical device, the one or more monitoring and/or treatment parameters and/or thresholds of the uninitialized medical device for use in operation of the uninitialized medical device. In this way, a manufacturer in a production assembly line and/or by a provider (e.g., a doctor, a nurse, etc.) in a care facility may ensure that the individual characteristics of the uninitialized medical device are delivered to that specific device and/or customize monitoring and/or treatment parameters and/or thresholds for a particular care facility (e.g., a particular location, a particular doctor, etc.) and/or for a particular patient.

In some embodiments, the one or more monitoring and/or treatment parameters and/or thresholds may include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

In some embodiments, the at least one processor is configured to execute one or more hardware and/or software tests and transmit, via the wireless connection between the external programming device and the uninitialized medical device, a result of the one or more hardware and/or software tests. For example, the external programming device may be configured to receive, via the wireless connection between the external programming device and the uninitialized medical device, the result of the one or more hardware and/or software tests executed by the uninitialized medical device. In this way, a hardware and/or software testing time for multiple uninitialized medical devices may be reduced by performing the testing concurrently or in parallel for the multiple uninitialized medical devices.

In some embodiments, the one or more hardware and/or software tests may include a test of hardware and/or software associated with at least one of the following: an LED operation; a photodiode operation; a DC-DC Component; a battery; a flash memory integrity; an actigraphy sensor; a chest motion sensor; or any combination thereof.

In some embodiments, the uninitialized medical device comprises a sleep apnea diagnostic or treatment device, the sleep apnea diagnostic or treatment device including: one or more physiological sensors configured to be bodily-attached to one or more portions of the patient's body and sense one or more physiological signals from the patient during sleep over a period of time; medical device wireless communications circuitry configured to transmit sleep data based on the sensed one or more physiological signals from the patient during sleep over the period of time; and at least one processor coupled to a memory. The at least one processor may be configured to control acquisition of the one or more physiological signals from the one or more physiological sensors and/or control the transmission of sleep data based on the one or more physiological signals. The one or more physiological sensors may include a photoplethysmography (PPG) sensor configured to be bodily-attached to a portion of the patient's body and sense an arterial pulse of the patient. The one or more physiological sensors may be configured to apply a substantially uniform subdiastolic pressure to a portion of the patient's body while sensing an arterial pulse as a peripheral arterial signal of the patient. The one or more portions of the patient's body may include one or more of a finger of the patient, a wrist of the patient, a toe of the patient, a lower arm of the patient, an upper arm of the patient, and/or a hand of the patient. As such, the one or more physiological sensors may include a finger probe including an optical sensor, a pneumatic sensor, and/or a pneumo-optical sensor. For example, the one or more physiological sensors may include a PPG sensor configured to be utilized in conjunction with a pressure device configured to apply the uniform subdiastolic pressure to the portion of the patient's body, and the pneumo-optical sensor may be configured to apply the uniform subdiastolic pressure to a distal two-thirds of the finger and fingertip of the patient's finger. As such, the uniform subdiastolic pressure may be configured to one or more of clamp the finger probe to the patient's finger, facilitate unloading of arterial wall tension, facilitate increase in a dynamic range of a peripheral arterial signal of the patient relative to PPG signals without the uniform subdiastolic pressure, and/or mitigate distal venous pooling or distention to avoid induction of venoarterial-mediated vasoconstriction.

In some embodiments, the sleep apnea diagnostic or treatment device may include a wrist-worn device, and the wrist-worn device may include the medical device wireless communications circuitry and the at least one processor coupled to the memory. In some embodiments, the sleep apnea diagnostic or treatment device may include a finger probe, and the finger probe may include the medical device wireless communications circuitry and the at least one processor coupled to a memory. In some embodiments, the one or more physiological sensors may include a chest motion sensor configured to be disposed on an upper chest area of the patient, the chest motion sensor including one or more of a snoring microphone and an accelerometer. In some embodiments, the one or more physiological sensors comprises one or more of ECG electrodes and a body impedance sensor. In some embodiments, the sleep apnea diagnostic or treatment device includes an onboard microcontroller implemented as a system-on-chip (SoC) that includes the medical device wireless communications circuitry and the at least one processor coupled to a memory.

Figure 1B:
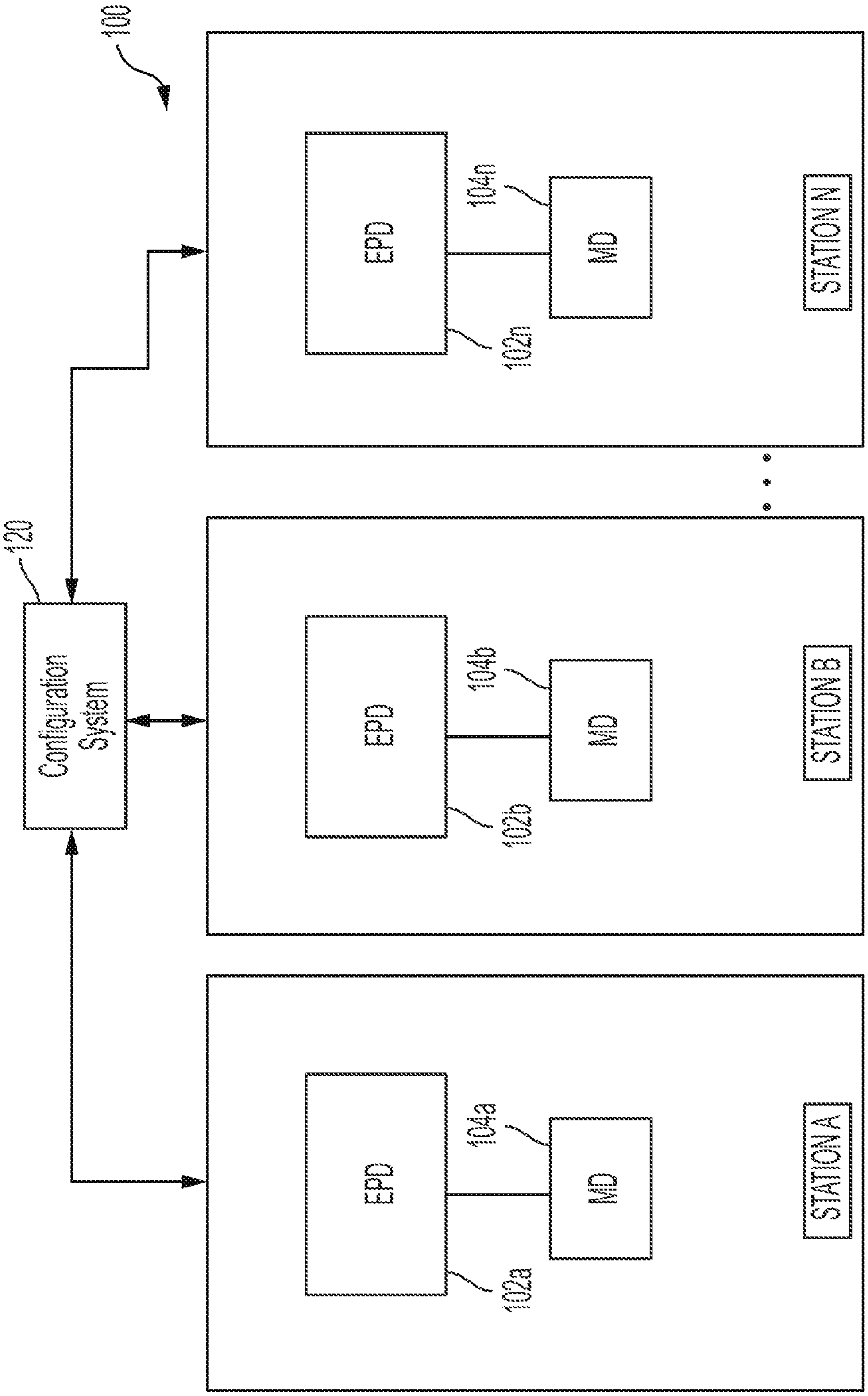

Referring to FIGS. 1A and 1B, FIGS. 1A and 1B show example block diagrams of a system 100 for initializing and subsequent programming of medical devices, according to some embodiments. As shown in FIG. 1A, system 100 includes external programming device (EPD) 102, medical device (MD) 104, wireless communication network 106, and/or wired connection 108. In some embodiments, as shown in FIG. 1B, system 100 includes a configuration system 120 and/or a plurality of programming stations or locations Station A, Station B, . . . Station N. For example, each programming station, Station A, Station B, . . . Station N may include an EPD 102 of a plurality of EPDs 102_a_, 102_b_, . . . 102_n_ and/or a MD 104 of a plurality of MDs 104_a_, 104_b_, . . . 104_n_. As an example, the plurality of programming stations or locations Station A, Station B, . . . Station N may be located proximate each other such that a coverage area or field of a wireless communication network associated with one or more of the plurality of programming stations or locations Station A, Station B, . . . Station N at least partially overlaps with a coverage area or field of a wireless communication network associated with one or more others of the plurality of programming stations or locations Station A, Station B, . . . Station N.

EPD 102 may include one or more devices capable of receiving information from and/or communicating information to MD 104 and/or configuration system 120 (e.g., via wireless communication network 106, via wired connection 108, etc.). In some embodiments, EPD 102 may include a server, a group of servers, and/or other like devices, as described herein. Additionally or alternatively, EPD 102 may include at least one other computing device separate from or including the server and/or group of servers, such as a portable and/or handheld device (e.g., a computer, a laptop, a personal digital assistant (PDA), a smartphone, a tablet, and/or the like), a desktop computer, and/or other like devices, as described herein. In some embodiments, EPD 102 may include at least one network interface (e.g., a server network interface and/or the like), at least one data storage device (e.g., a server database and/or the like), at least one processor (e.g., a server processor and/or the like), any combination thereof, and/or the like. For example, EPD 102 may include at least one processor operatively connected to a non-transitory computer-readable medium, as described herein. In some embodiments, EPD 102 may be in communication with at least one data storage device (e.g., a server database and/or the like), which may be local or remote to EPD 102. In some embodiments, EPD 102 may be capable of receiving information from, storing information in, communicating information to, or searching information stored in the data storage device (e.g., a server database and/or the like).

Figure 2:
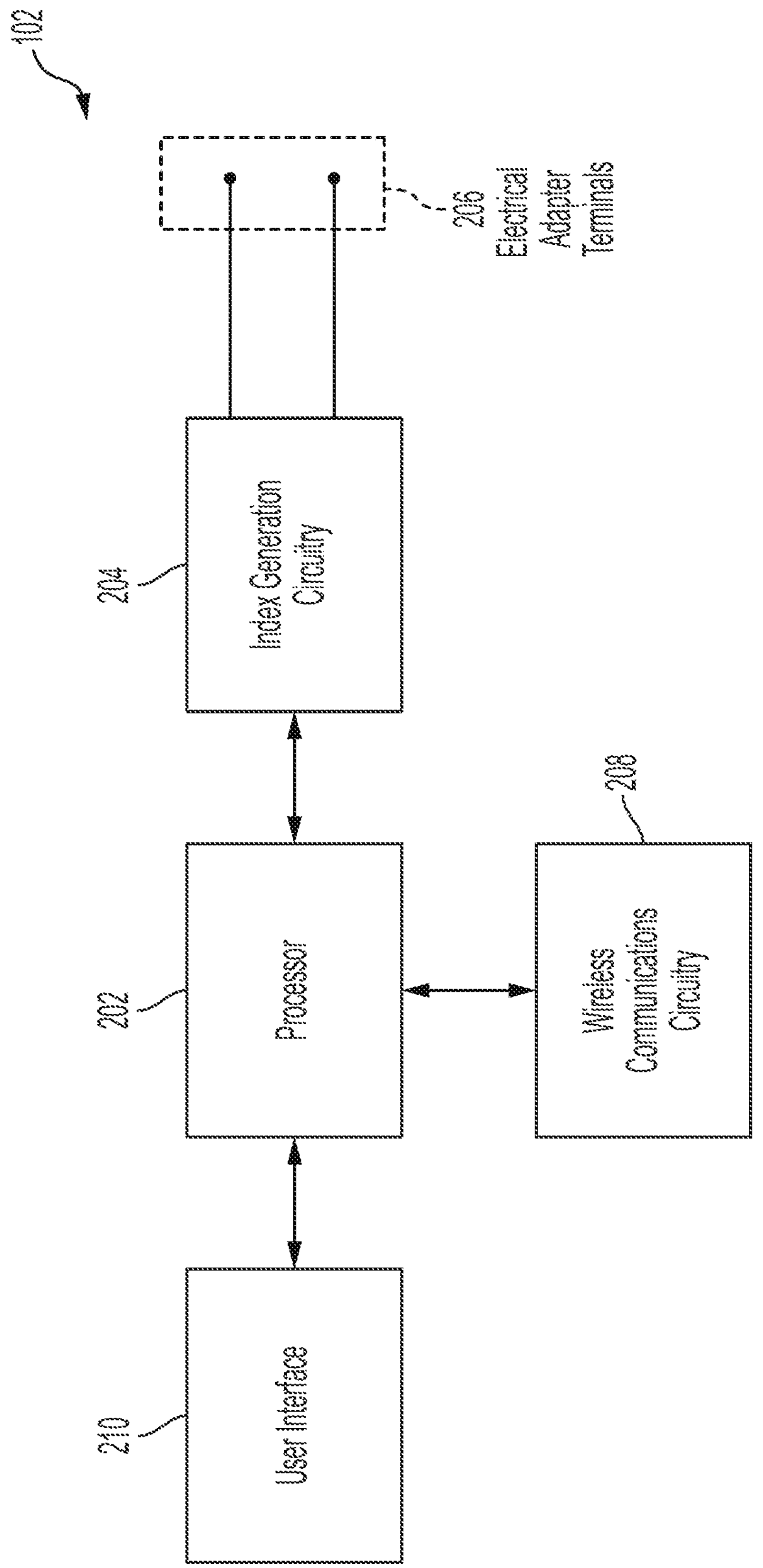
FIG. 2 shows an example block diagram of an external programming device (EPD), according to some embodiments.

Referring also to FIG. 2, FIG. 2 shows an example block diagram of EPD 102, according to some embodiments. As shown in FIG. 2, EPD 102 may include processor 202, index generation circuitry 204, electrical adapter terminals 206, wireless communications circuitry 208, and/or user interface 210.

Processor 202 may be coupled to a memory and operatively connected to index generation circuitry 204, electrical adapter terminals 206, wireless communications circuitry 208, and/or user interface 210. For example, processor 202 may be configured to control index generation circuitry 204 to transmit a voltage-based index value through wired connection 108 to MD 104 (e.g., to one of the plurality of MDs 104_a_, 104_b_, . . . 104_n_), the voltage-based index value identifying EPD 102 (e.g., uniquely identifying one of the plurality of EPDs 102_a_, 102_b_, . . . 102_n_). As an example, processor 202 may be configured to control wireless communication circuitry 208 to establish a wireless connection between EPD 102 and MD 104 based on the voltage-based index value (e.g., in response to receiving a wireless connection request including the voltage-based index value from MD 104). In such an example, processor 202 may be configured to control wireless communication circuitry to transmit, via the wireless connection between EPD 102 and MD 104, a unique medical device identifier to MD 104 that causes MD 104 to be uniquely addressable. For example, EPD 102 may be configured to burn-in MD 104, via the wireless connection between EPD 102 and MD 104, the unique medical device identifier and/or program, via the wireless connection between EPD 102 and MD 104, one or more monitoring and/or treatment parameters and/or thresholds of MD 104 for use in operation of MD 104.

Index generation circuitry 204 may be configured to generate a voltage-based index value as a voltage signal based on a predetermined input to the index generation circuitry. User interface 210 (e.g., a touch screen display, a keyboard, a keypad, a mouse, a button, a switch, a microphone, a camera, input component 810, and/or the like) may be configured to receive a user input and produce the predetermined input to index generation circuitry 204 based on the user input. The user input may include an index value that identifies EPD 102 and/or a wireless communication network associated with EPD 102 (e.g., a Bluetooth address, a Wi-Fi service set identifier (SSID), etc.).

In some embodiments, index generation circuitry 204 may be configured to generate a voltage-based index value as a voltage signal by generating the voltage signal as a predetermined supply voltage associated with the voltage-based index value. For example, index generation circuitry 204 may be configured to generate the voltage signal within a predetermined voltage range (e.g., between about 1.6 V and about 3.3 V) sufficient to feed stable power to MD 104 to boot or power-on and operate (e.g., to boot and operate in a first mode, such as an initialization mode, a pre-programming mode, a production mode, or other such mode configured for initializing the uninitialized medical device as described herein) and at a predetermined supply voltage level within the voltage range that identifies EPD 102. As an example, a voltage level of about 1.7V (e.g., ±0.1 V) may power-on MD 104 and identify a first EPD 102*a* of the plurality of EPDs 102*a*, 102*b*, . . . 102*n*, a voltage level of about 2.0 V (e.g., ±0.1 V) may power-on MD 104 and identify a second EPD 102*b* of the plurality of EPDs 102*a*, 102*b*, . . . 102*n*, and/or a voltage level of about 2.3V (e.g., ±0.1 V) may power-on MD 104 and identify an nth EPD 102*a* of the plurality of EPDs 102*a*, 102*b*, . . . 102*n*, and/or the like. In such an example, the voltage level may directly identify the EPD 102 to MD 104, such as directly identify a Bluetooth address of EPD 102, directly identify a Wi-Fi SSID of EPD 102, and/or the like (e.g., the Bluetooth address of EPD 102*a* may be preconfigured as 1.7, the Bluetooth address of EPD 10*b* may be preconfigured as 2.0, etc.) and/or MD 104 may access a look-up table (e.g., pre-stored in memory 307, etc.) that determines which voltage level identifies which EPD of the plurality of EPDs 102*a*, 102*b*, . . . 102*n*. Accordingly, a number of EPDs 102 that can be used concurrently or in parallel may be as large as allowed by the available range of predetermined supply voltages and/or a degree at which the available range is segmented into the predetermined supply voltages assigned to identify the plurality of EPDs 102*a*, 102*b*, . . . 102*n*.

In some embodiments, index generation circuitry 204 is configured to generate a voltage-based index value as a voltage signal by generating the voltage signal as varying voltages between two predefined voltage levels to encode the voltage-based index value in the voltage signal. For example, the voltage-based index value may be encoded in the voltage signal as a binary sequence of bits. As an example, index generation circuitry 204 may be configured for digital communication over a DC and/or battery-powered line using a universal asynchronous receiver-transmitter (UART)-based protocol, and/or the like.

Figure 1C:
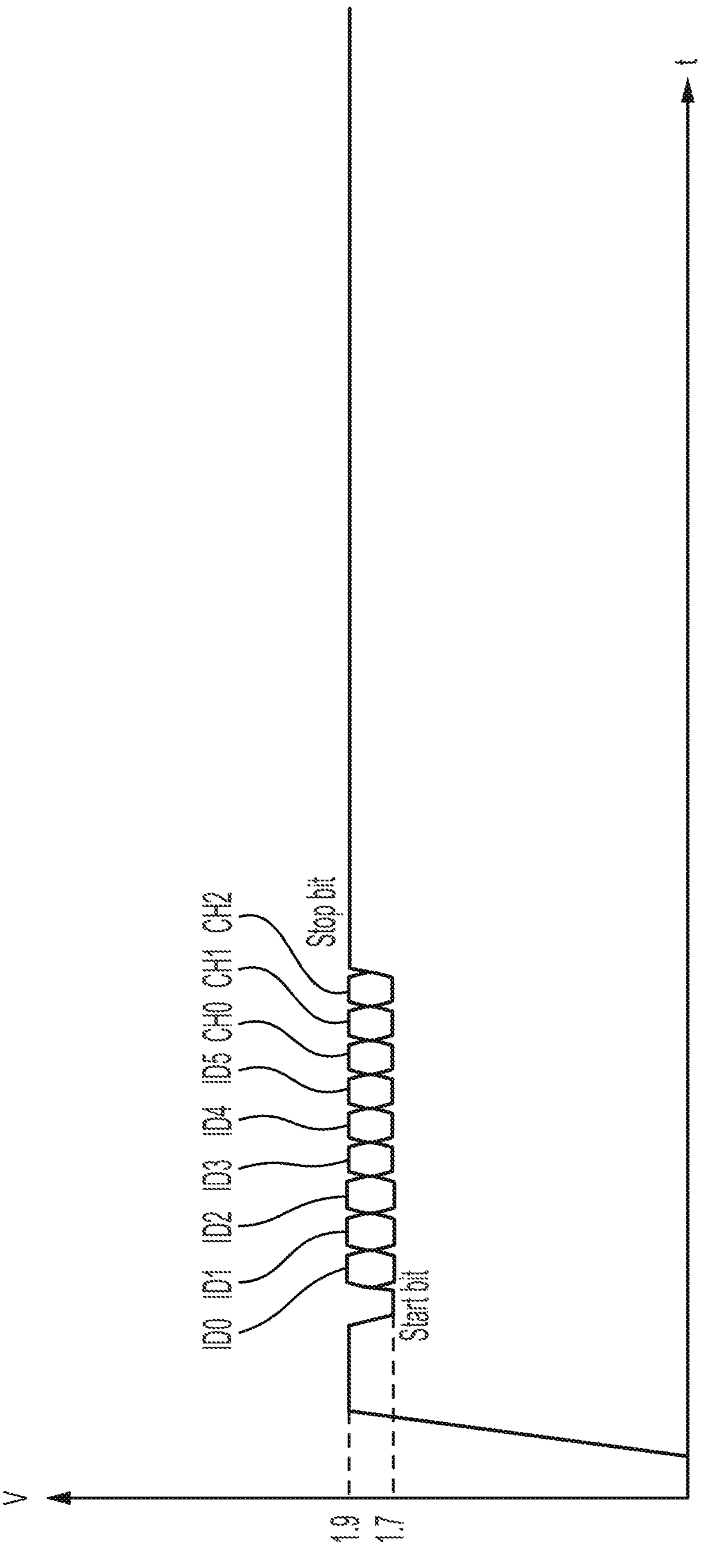
FIG. 1C is a graph of an example voltage-based index value transmitted as varying voltages between two predefined voltage levels, according to some embodiments.

FIG. 1C is a graph of an example voltage-based index value transmitted as varying voltages between two predefined voltage levels. As shown in FIG. 1C, the voltage-based index value may be generated and/or transmitted according to a specification or protocol that defines a voltage of greater than or equal to 1.9 V as a high or "1" bit value and a voltage of greater than or equal to 1.5 V and less than or equal to 1.7 V as a low or "0" bit value (e.g., with the threshold between the "1" and "0" bit values being 1.8 V). The varying voltage levels may be used to code a 6-bit word on wired connection 108 that is defined according to the specification or protocol as including a start bit of "0" bit value, a bit duration of 10 ms, a word structure of 6 bits of data ID0-ID5 (e.g., the voltage-based index value that identifies EPD 102) and 3 checksum bits CH0-CH2 (e.g., a sum of all the bits), and a stop bit of "1" bit value. For example, an initial voltage (e.g., 1.97 V) for an initial period of time (e.g., 4 seconds) on wired connection 108 may cause MD 104 to "power-on" in an initialization mode, a pre-programming mode, a production mode, or other such mode configured for initializing the uninitialized medical device, and indicate that the MD 104 is going to receive a voltage-based index value via its battery terminals or power line. After the initial period, the start bit, the 6 data bits, the 3 checksum bits, and the stop bit may be transferred with the bit duration of 10 ms, which may be received and reconstructed as the voltage-based index value by MD 104.

Figure 1D:
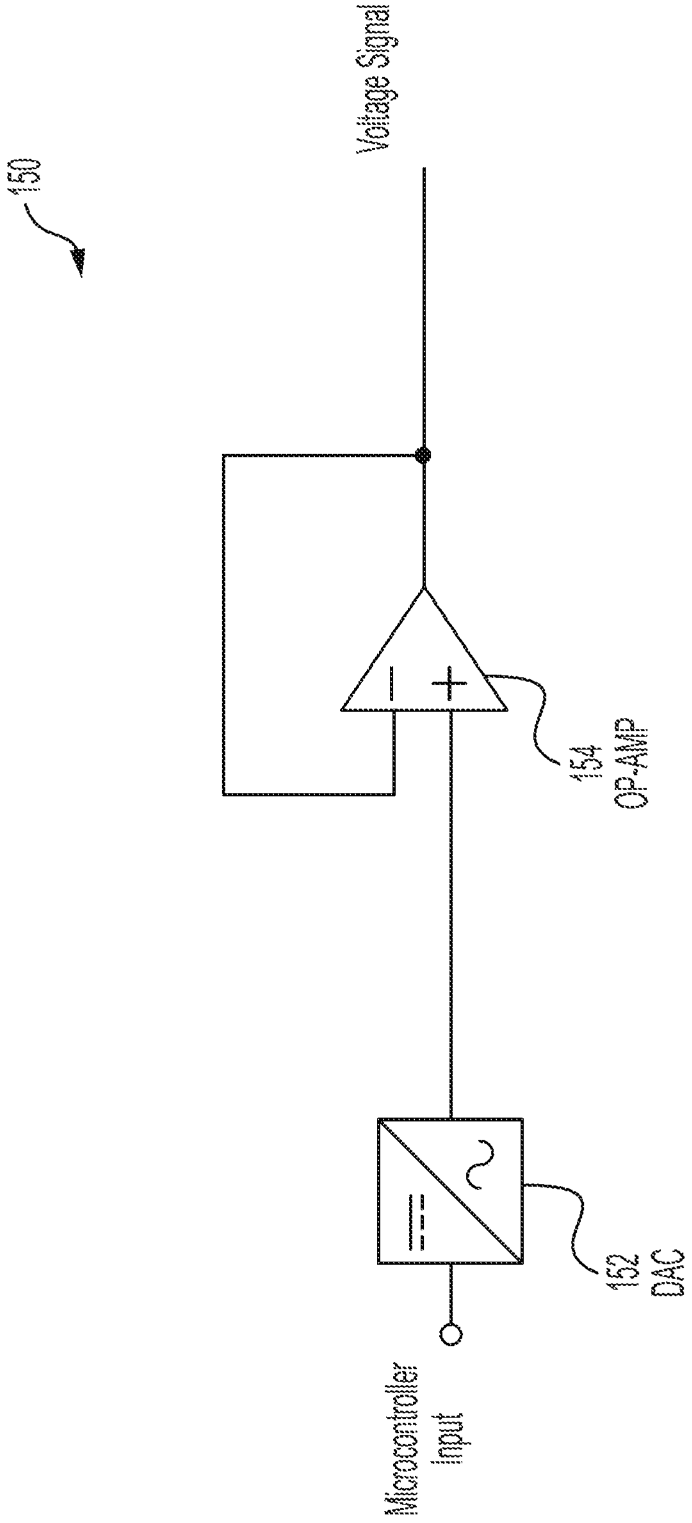
FIG. 1D is a circuit diagram of example voltage generation circuitry, according to some embodiments.

FIG. 1D is a circuit diagram of example voltage generation circuitry 150. For example, index generation circuitry 204 may include voltage generation circuitry 150, and/or voltage generation circuitry 150 may be configured to generate the voltage signal as the predetermined supply voltage associated with the voltage-based index value and/or the voltage signal as the varying voltages between the two predefined voltage levels to encode the voltage-based index value in the voltage signal. As an example, voltage generation circuitry 150 may be configured to modulate the index value on the power supply provided to MD 104 from EPD 102 via wired connection 108. In such an example, EPD 102 may include a tool microcontroller program digital-to-analog (DAC) converter configured generate the desired voltage, and the DAC output may be amplified to drive the target uninitialized medical device power supply.

As shown in FIG. 1D, voltage generation circuitry 150 may include a DAC 152 (e.g., a 16-bit DAC, etc.) and an operational amplifier (OP-AMP) 154. DAC 152 may be configured to provide a desired output voltage in response to an input from the microcontroller (e.g., processor 306, etc.). OP-AMP 154 may be configured to amplify the DAC output voltage. The output of OP-AMP 154 may be a voltage signal used to drive the power supply of the target uninitialized medical device.

In such an example, a 16-bit DAC provides a capability to modulate 63 different index values. The index value can be coded and transmitted digitally as a serial asynchronous communication (e.g., UART, etc.) modulated on two voltage levels (e.g., 1.7V and 1.9V, etc.). 6 bits ID5 . . . ID0 can be used to encode 63 different IDs (1-63) and an additional 3 bits CH2 . . . CH0 may be used as checksum for verification. The index value can be transmitted on power-up of the target uninitialized medical device and read by the target uninitialized medical device, which may repeatedly sample the supply voltage and decode the index value therefrom.

Figure 1E:
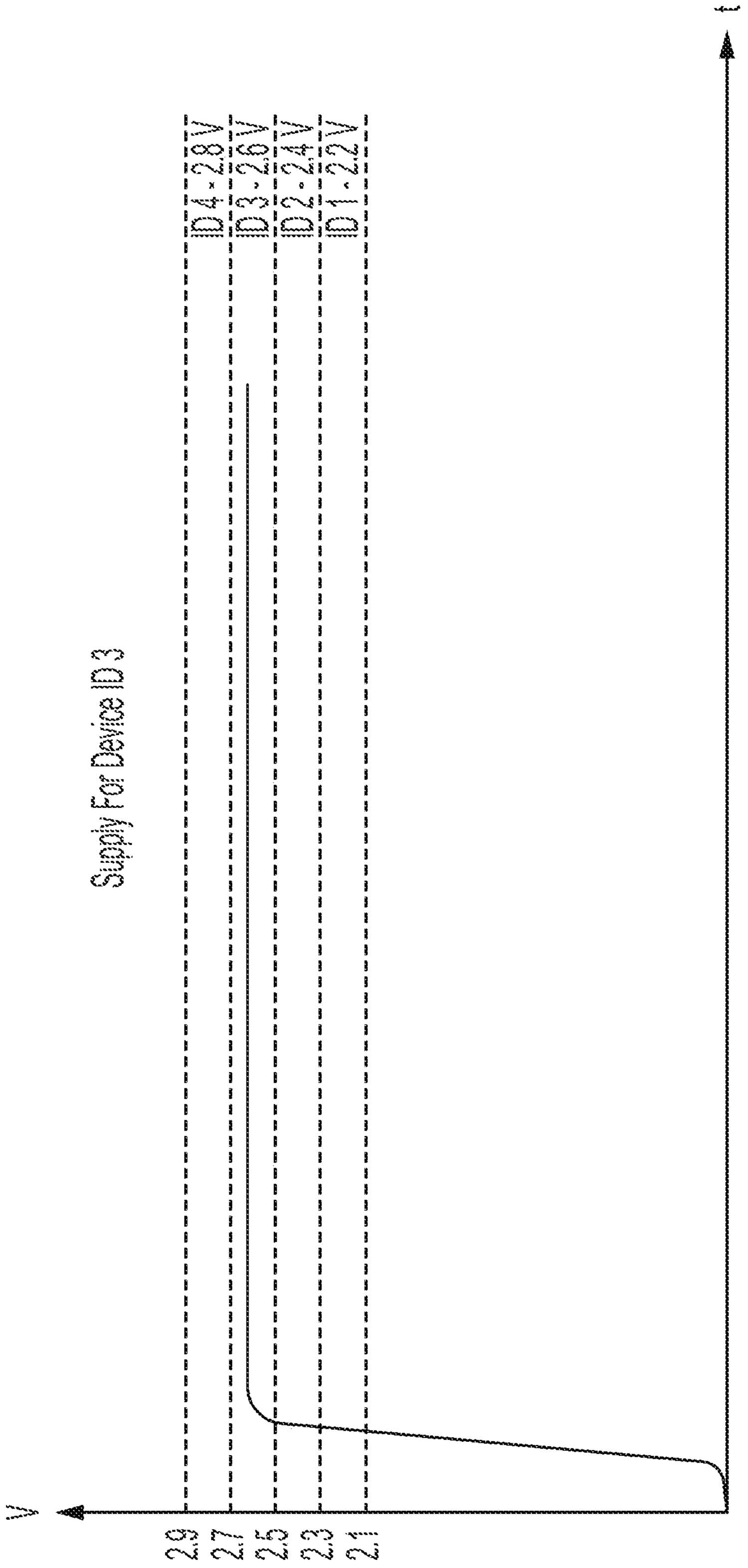
FIG. 1E is a graph of an example voltage-based index value transmitted as a predetermined supply voltage, according to some embodiments.

FIG. 1E is a graph of an example voltage-based index value transmitted as a predetermined supply voltage. As shown in FIG. 1E, different predetermined supply voltages may be associated with different index values. For example, a first index value ID1 may be associated with a first predetermined supply voltage of 2.2 V (e.g., a predetermined voltage range between 2.1 V and 2.3 V), a second index value ID2 may be associated with a second predetermined supply voltage of 2.4 V (e.g., a predetermined voltage range between 2.3 V and 2.5 V), a third index value ID3 may be associated with a third predetermined supply voltage of 2.6 V (e.g., a predetermined voltage range between 2.5 V and 2.7 V), and a fourth index value ID4 may be associated with a fourth predetermined supply voltage of 2.8V (e.g., a predetermined voltage range between 2.7 V and 2.9 V). A same or similar circuit as used for generating the voltage signal as the varying voltages between the two predefined voltage levels may be used for generating the voltage-based index value as the predetermined supply voltage. As an example, voltage generation circuitry 150 can be configured to provide the predetermined supply voltage in response to the input from the microcontroller (e.g., processor 306, etc.). In such an example, the target uninitialized medical device includes circuitry configured to measure the power supply voltage on power-up and extract the index value according to the measurement result. For example, MD 104 may access a look-up table (e.g., pre-stored in memory 307, etc.), such as that shown below in Table 1, that determines which predetermined supply voltage level identifies which EPD of the plurality of EPDs 102*a*, 102*b*, 102*n*.

TABLE 1

| Predetermined Supply Voltage | EPD ID # |
|---|---|
| 2.2 V | 1 |
| 2.4 V | 2 |
| 2.6 V | 3 |
| 2.8 V | 4 |

Figure 1F:
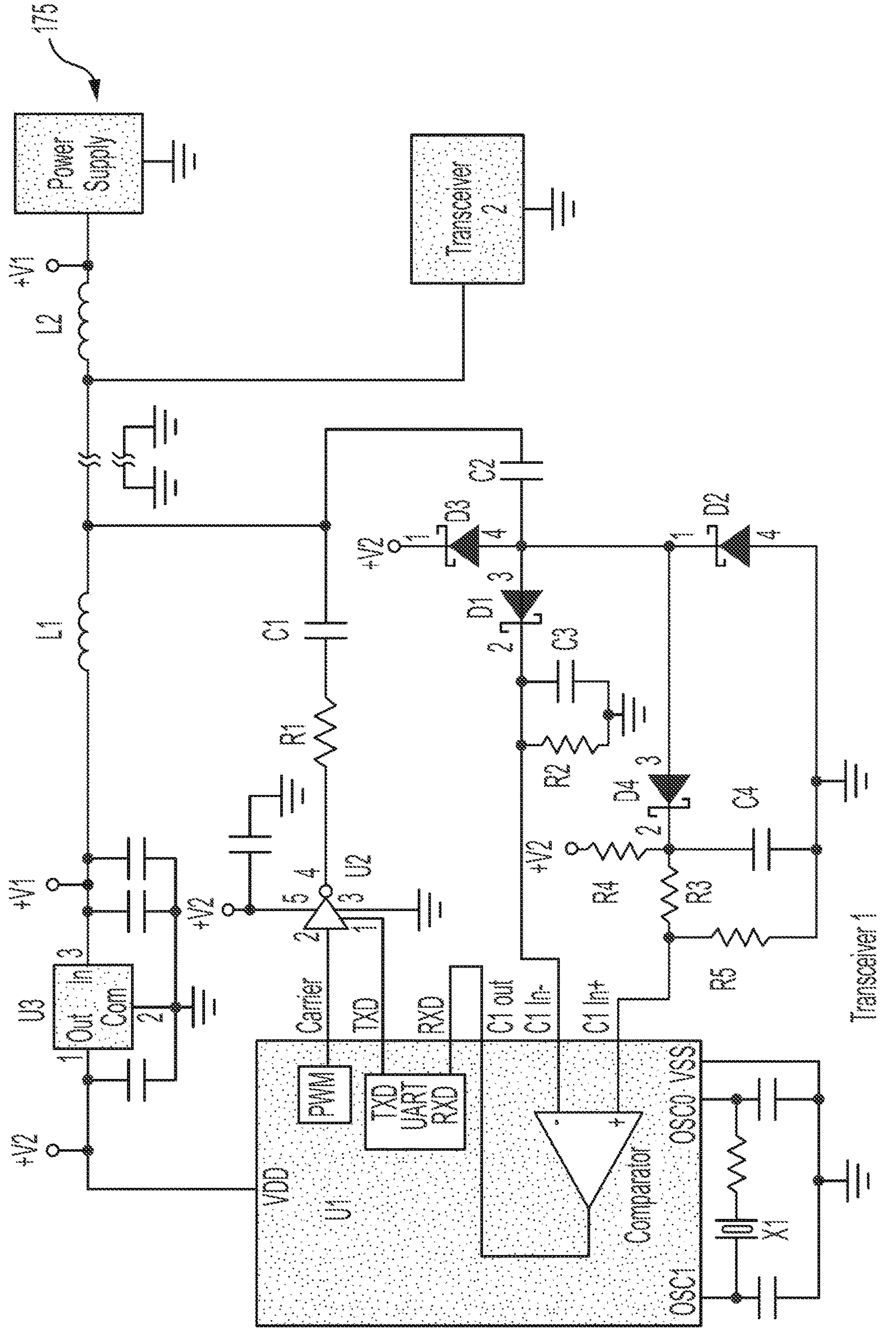
FIG. 1F shows an example circuit diagram of a power line communication system, according to some embodiments.

Referring to FIG. 1F, FIG. 1F shows an example circuit diagram of a UART-compatible power line communication system 175. Devices of system 175 may correspond to one or more devices of EPD 102 and/or MD 104 (e.g., index generation circuitry 204, voltage receiving circuitry 310, etc.), and/or EPD 102 and/or MD 104 (e.g., index generation circuitry 204, voltage receiving circuitry 310, etc.) may include at least one device of system 175 and/or at least one component of a device of system 175. As shown in FIG. 1F, power line communication system 175 may include a two-transceiver system in which Transceiver 1 (e.g., MD 104, power receiving circuitry 310, etc.) is a "remote" node receiving power from a "base" unit Transceiver 2 (e.g., EPD 102, index generation circuitry 204, etc.). Inductors L1 and L2 may isolate the high-frequency carrier from the low impedances on the power sides. A microcontroller unit (MCU) U1 (e.g., a PIC microcontroller, etc.) may include a pulse-width modulation (PWM) module or programmable time base for generating a square-wave carrier (e.g., a changing square wave pulse train in which the voltage-based index value is encoded, etc.) and a high-speed analog comparator whose input common-mode range includes ground or very close to ground. A transmitter portion of each transceiver, which may be omitted from MD 104 and/or voltage receiving circuitry 310, may include a tri-state line driver U2, the output of which may be coupled to the bus (e.g., wired connection 108, etc.) by resistor RI and capacitor C1. Resistor RI may provide filtering to minimize electromagnetic interference (EMI) from the sharp edges of the square-wave carrier. A receiver portion of a transceiver (e.g., Transceiver 1, Transceiver 2, etc.), which may be omitted from EPD 102 and/or index generating circuitry 204, may include a clamp formed by capacitor C2, diode D2, and diode D3, followed by two peak detectors. The first peak detector, which may have a time constant of approximately one-third of the data bit time, may demodulate the carrier to recover the data timing. The second peak detector, which may have a time constant of about 50 times the bit time, may adaptively follow the carrier level. Resistor R3 and Resistor R5 may divide this level to approximately two-thirds of the carrier amplitude. Demodulator and reference level outputs may be applied to the inputs of the MCU U1*s* internal analog comparator to square up the final data, which may be routed externally to the MCU U1's UART. Resistor R4 may bias the positive input of the comparator slightly positive to ensure a predictable logic-high idle state. As such, the voltage-based index may be sent from the EPD 102's transceiver's UART TX port, provided as a modulated carrier on the bus (e.g., on wired connection 108, etc.), and/or provided as demodulated and reconstructed data by the MD 104's receiver's comparator to the receiver's UART RXD port.

In some embodiments, index generation circuitry 204 may be configured to generate the voltage-based index value as the voltage signal or modulated carrier (and/or voltage receiving circuitry 310 may be configured to read the voltage based index value from the voltage signal or modulated carrier) according to a specification or protocol that defines a voltage of greater than or equal to 1.9 V as a high or "1" bit value and a voltage of greater than or equal to 1.5 V and less than or equal to 1.7 V as a low or "0" bit value (e.g., with the threshold between the "1" and "0" bit values being 1.8 V). Index generation circuitry 204 may use the different voltage levels to code a 6-bit word on wired connection 108 that is defined according to the specification or protocol as including a start bit of "0" bit value, a bit duration of 10 ms, a word structure of 6 bits of data (e.g., the voltage-based index value that identifies EPD 102) and 3 checksum bits (e.g., a sum of all the bits), and a stop bit of "1" bit value. For example, index generation circuitry 204 may provide an initial voltage (e.g., 1.97 V) for an initial period of time (e.g., 4 seconds) on wired connection 108, which may cause MD 104 to cause the MD 104 to initiate in an initialization mode, a pre-programming mode, a production mode, or other such mode configured for initializing the uninitialized medical device, and indicate that the MD 104 should receive a voltage-based index value is to be transferred to MD 104 via its battery terminals or power line. After the initial period, index generation circuitry 204 may transfer the start bit, the 6 data bits, the 3 checksum bits, and the stop bit with the bit duration of 10 ms, which may be received by voltage receiving circuitry 310 and reconstructed as the voltage-based index value by MD 104.

Wired connection 108 may include electrical adapter terminals 206 of EPD 102 and/or electrical battery terminals 312 of MD 104. For example, EPD 102 may include a battery adapter including electrical adapter terminals 206 configured to connect to electrical battery terminals 312 of MD 104. (e.g., a pair of electrical adapter terminals including a positive terminal and a negative terminal configured to connect to a pair of electrical battery terminals including a positive terminal and a negative terminal, etc.).

Wireless communications circuitry 208 may include at least one of the following: cellular communications circuitry, Bluetooth communications circuitry, Advanced Message Queuing Protocol (AMQP) circuitry, Constrained Application Protocol (CoAP) circuitry, Wi-Fi circuitry, ZigBee circuitry, Z-Wave circuitry, wireless personal area network (WPAN) circuitry, Infrared Data Association (IrDA) circuitry, any combination thereof, and/or the like. For example, wireless communications circuitry 208 of EPD 102 may be configured to establish at least one of the following types of wireless connections with wireless communications circuitry 304 of MD 104: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, any combination thereof, and/or the like.

MD 104 may include one or more devices capable of receiving information from and/or communicating information to EPD 102 (e.g., via wireless communication network 106, via wired connection 108, etc.). As an example, MD 104 may include a wearable device 1500 for diagnosing, recording sleep related physiological parameters, storing such sleep related physiological parameters, and/or monitoring such sleep related physiological parameters. For example, such sleep related physiological parameters include sleep disordered breathing parameters as described herein below with respect to FIGS. 15-18 and 19A-19F. However, non-limiting embodiments or aspects of the present disclosure are not limited thereto, and MD 104 may include other wearable medical devices for diagnosing sleep and/or cardiac conditions, recording physiological signals, storing such physiological signals, monitoring physiological signals and/or treatment of a patient's underlying sleep and/or cardiac condition, such as a cardiac monitor, a wearable defibrillator, and/or the like.

Figure 3:
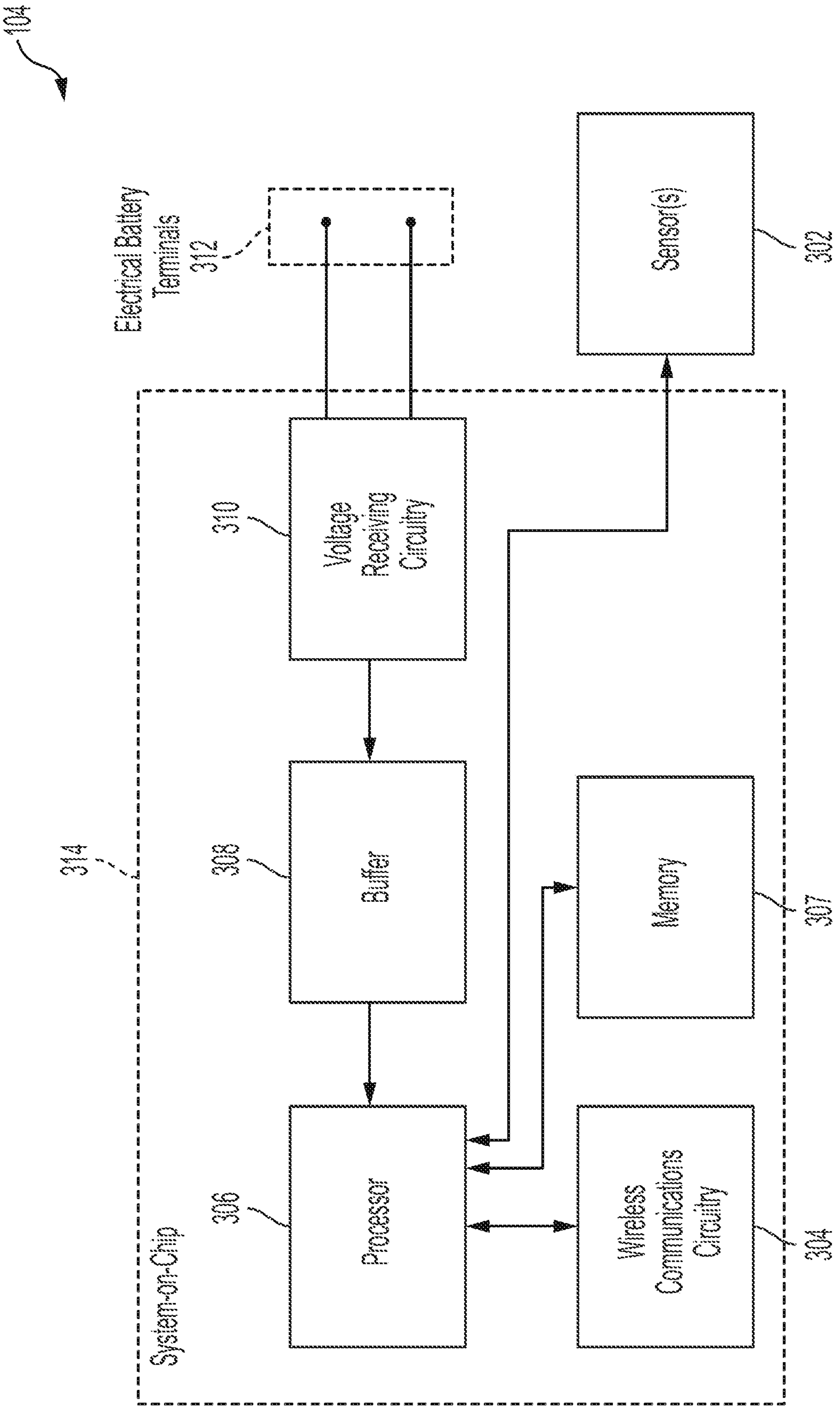
FIG. 3 shows an example block diagram of a medical device (MD), according to some embodiments.

Referring also to FIG. 3, FIG. 3 shows an example block diagram of MD 104, according to some embodiments. As shown in FIG. 3, MD 104 may include one or more physiological sensors 302, wireless communications circuitry 304, and/or processor 306 coupled to a memory 307.

The one or more physiological sensors 302 may be configured to be bodily-attached to a patient and sense physiological signals from the patient over a period of time. Processor 306 may be operatively connected to the one or more physiological sensors 302. The one or more physiological sensors 302 may include at least one of the following: a heart rate sensor, an oxygen saturation sensor, an actigraphy sensor (e.g., an accelerometer), a snoring sensor (e.g., a microphone, a vibration sensor, and/or the like), a chest motion sensor, a body position sensor, an arm position sensor, a sleep stage sensor, an accelerometer, an electrode, a gyroscope, a PPG sensor, a pneumo-optical sensor, any combination thereof, and/or the like.

Wireless communications circuitry 304 may include at least one of the following: cellular communications circuitry, Bluetooth communications circuitry, Advanced Message Queuing Protocol (AMQP) circuitry, Constrained Application Protocol (CoAP) circuitry, Wi-Fi circuitry, ZigBee circuitry, Z-Wave circuitry, wireless personal area network (WPAN) circuitry, Infrared Data Association (IrDA) circuitry, any combination thereof, and/or the like. For example, wireless communications circuitry 304 of MD 104 may be configured to establish at least one of the following types of wireless connections with a remote computing system and/or wireless communications circuitry 304 of MD 104: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, any combination thereof, and/or the like.

Processor 306 may be configured to control acquisition of the one or more physiological signals from the one or more physiological sensors and/or control the transmission of data by wireless communications circuitry 304 based on the one or more physiological signals. In some embodiments, processor 306 may be configured to receive, via wired connection 108 with EPD 102, a voltage-based index value that identifies EPD 102. For example, processor 306 may control wireless communications circuitry 304 to establish a wireless connection between EPD 102 and wireless communications circuitry 304 based on the voltage-based index value. As an example, processor 306 may be configured to receive, via the wireless connection between EPD 102 and MD 104, a unique medical device identifier that causes MD 104 to be uniquely addressable. In such an example, processor 306 may store or burn-in, in memory 307, the unique medical device identifier to initialize MD 104 by causing MD 104 to be uniquely addressable.

In some embodiments, processor 306 may be configured to receive and/or store, via the wireless connection between EPD and MD 104, one or more monitoring and/or treatment parameters and/or thresholds of MD 104 for use in operation of MD 104 (e.g., for use in the second mode of MD 104, such as a diagnostic or treatment mode of MD 104, or the like). For example, the one or more monitoring and/or treatment parameters and/or thresholds may include a parameter and/or threshold associated with at least one of the following: a patient name; a patient gender; a patient weight; a unique patient identifier; a unique provider identifier; a number of allowed uses of the uninitialized medical device; a frequency at which the uninitialized medical device communicates with a remote computer system; a wavelength of at least one LED of at least one sensor of the uninitialized medical device; a peripheral arterial measurement of a pneumo-optical sensor of the uninitialized medical device; a photoplethysmogram measurement of a photoplethysmogram (PPG) sensor of the uninitialized medical device; a heart rate measurement of a heart rate sensor of the uninitialized medical device; an actigraphy measurement of an actigraphy sensor of the uninitialized medical device; a snoring measurement of a snoring sensor of the uninitialized medical device; a chest motion measurement of a chest motion sensor of the uninitialized medical device; a body position measurement of a body position sensor of the uninitialized medical device; an arm position measurement of an arm position sensor of the uninitialized medical device; a sleep stage measurement of a sleep stage sensor of the uninitialized medical device; or any combination thereof.

As an example, MD 104 may include one or more optical sensors including one or more red and/or infrared LEDs and/or diodes. For example, measuring pulse oximetry may use at least two LEDs with different wavelengths (e.g., a red LED and an infrared LED), which wavelengths are used by MD 104. As an example, accurate oximetry calculations may rely on the wavelength's actual value of the LEDs used for measuring the red and infrared values, and the actual measured wavelength value of each specific LED in that specific MD 102 may be determined or measured (e.g., during assembly, during a calibration process, etc.). For example, a calibration process may assign a discrete curve (e.g., out of a 1-5 range, etc.) based on the measured wavelength of the LEDs that is used by MD 104 to determine coefficients to be used for calculation of oximetry saturation. In such an example, each curve may be characterized by its corresponding set of coefficients. As such, the assigned curve and its corresponding coefficients may be the characteristics of the LED(s) of MD 104, which may differ between MDs 104 or the LEDs. These values from the assigned curve may be transmitted to MD 104 for use in performing oximetry calculations.

In some embodiments, processor 306 may be configured to execute one or more hardware and/or software tests and transmit, via the wireless connection between EPD 102 and MD 104, a result of the one or more hardware and/or software tests. For example, the one or more hardware and/or software tests may include a test of hardware and/or software associated with at least one of the following: an LED operation; a photodiode operation; a DC-DC Component; a battery; a flash memory integrity; an actigraphy sensor; a chest motion sensor; or any combination thereof.

As further shown in FIG. 3, MD 104 may further include buffer 308, voltage receiving circuitry 310, and/or battery terminals 312. Voltage receiving circuitry 310 may be connected to battery terminals 312. For example, voltage receiving circuitry 310 may be configured to receive a voltage signal via battery terminals 312 (e.g., via wired connection 108 including a pair of electrical battery terminals 312).

In some embodiments, MD 104 may be configured to operate in a plurality of different modes. For example, in response to receiving the voltage signal via the wired connection, MD 104 may be configured to operate in a first mode (e.g., an initialization mode, a pre-programming mode, a production mode, or other such mode configured for initializing the uninitialized medical device) in response to a voltage of the voltage signal being within a first voltage range, and to boot or power-on and/or operate in a second mode (e.g., a diagnostic or treatment mode, a normal operation mode, or the like) different than the first mode in response to the voltage of the voltage signal being within a second voltage range higher than and disjoint of the first voltage range. As an example, the first voltage range may be between about 1.6 V and about 3.3 V (e.g., ±0.1 V, etc.), and the voltage of the voltage signal may be within the first voltage range, and/or the second voltage range may be between about 3.4 V and 5.0 V (e.g., ±0.1 V, etc.).

In some embodiments, voltage receiving circuitry 310 may receive the voltage signal as a predetermined supply voltage associated with the voltage-based index value. For example, voltage receiving circuitry 310 may receive the voltage signal within a predetermined voltage range (e.g., between about 1.6 V and about 3.3 V) sufficient to feed stable power to MD 104 to boot or power-on and operate (e.g., to boot and operate in a first mode, such as an initialization mode, a pre-programming mode, a production mode, or other such mode configured for initializing the uninitialized medical device) and at a predetermined voltage level within the voltage range that identifies EPD 102. As an example, voltage receiving circuitry 310 may include a voltage sensor that provides voltage data that indicates the voltage level of the voltage signal to processor 306. In such an example, the voltage level may directly identify the EPD 102 to MD 104, such as directly identify a Bluetooth address of EPD 102, directly identify a Wi-Fi SSID of EPD 102, and/or the like (e.g., the Bluetooth address of EPD 102*a* may be preconfigured as 1.7, the Bluetooth address of EPD 102*b* may be preconfigured as 2.0, etc.) and/or MD 104 may access a look-up table (e.g., pre-stored in memory 307, etc.) that determines which voltage level identifies which EPD of the plurality of EPDs 102*a*, 102*b*, . . . 102*n*.

In some embodiments, voltage receiving circuitry 310 may receive the voltage signal as varying voltages between two predefined voltage levels that encodes the voltage-based index value in the voltage signal. For example, voltage receiving circuitry 310 may receive the voltage signal within a predetermined voltage range (e.g., between about 1.6 V and about 3.3 V) sufficient to feed stable power to MD 104 to operate in a first mode, such as an initialization mode, a pre-programming mode, a production mode, or other such mode configured for initializing the uninitialized medical device as described herein, and with varying voltages within the voltage range that encodes the voltage-based index value that identifies EPD 102 in the voltage signal. For example, voltage receiving circuitry 310 may be configured to determine, based on the voltage signal, a binary sequence of bits and store, in buffer 308, the binary sequence of bits. Processor 306 may be operatively coupled to buffer 308. For example, processor 306 may be configured to read, from buffer 308, the binary sequence of bits and determine, based on the binary sequence of bits, a voltage-based index value that identifies EPD 102.

In some embodiments, as described herein in more detail with respect to FIG. 1F, devices of a UART-compatible power line communication system 175 may correspond to one or more devices of MD 104 (e.g., voltage receiving circuitry 310, etc.), and/or MD 104 (e.g., voltage receiving circuitry 310, etc.) may include at least one device of system 175 and/or at least one component of a device of system 175. As such, voltage receiving circuitry 310 may be configured to provide as demodulated and reconstructed data by the MD 104's receiver's comparator to the receiver's UART RxD port, the voltage-based index value that identifies EPD 102 in response to receiving a modulated carrier on the bus (e.g., on wired connection 108, etc.) generated by index generation circuitry 204 of EPD 102 based on the voltage-based index being sent from the EPD 102's transceiver's UART Tx port.

In some embodiments, MD 104 may include a system-on-chip (SoC) 314 that includes wireless communications circuitry 304, processor 306, memory 307, buffer 308, voltage receiving circuitry 310, any combination thereof, and/or the like.

In some embodiments, MD 104 may be uninitialized. For example, an uninitialized MD 104 may include a medical device that is not uniquely addressable from other medical devices (e.g., from other medical devices of the plurality of medical devices 104*a*, 104*b*, . . . 104*n*), a medical device for which one or more monitoring and/or treatment parameters and/or thresholds have not been set and/or assigned a value, a medical device for which one or more hardware and/or software tests have not been executed by the medical device and/or confirmed by EPD 102, any combination thereof, and/or the like. As an example, an uninitialized MD 104 may not have received and/or stored (e.g., burned-in, etc.) in memory 307 a unique medical device identifier that causes the uninitialized medical device to be uniquely addressable, may not have received and/or assigned values to one or more monitoring and/or treatment parameters and/or thresholds (e.g., a wavelength of at least one LED of sensor(s) 302, etc.), may not have executed and/or provided a result to EPD 102 of one or more hardware and/or software tests (e.g., a flash memory integrity test, etc.), or any combination thereof, and/or the like.

In some embodiments, MD 104 may include a sleep apnea diagnostic or treatment device. For example, the one or more physiological sensors 302 may be configured to sense the one or more physiological signals from the patient during sleep over the period of time. As an example, wireless communications circuitry 304 may be configured to transmit sleep data based on the one or more physiological signals sensed from the patient during sleep over the period of time. In such an example, processor 306 may control acquisition of the one or more physiological signals from the one or more physiological sensors and/or control the transmission of the sleep data.

Figure 4:
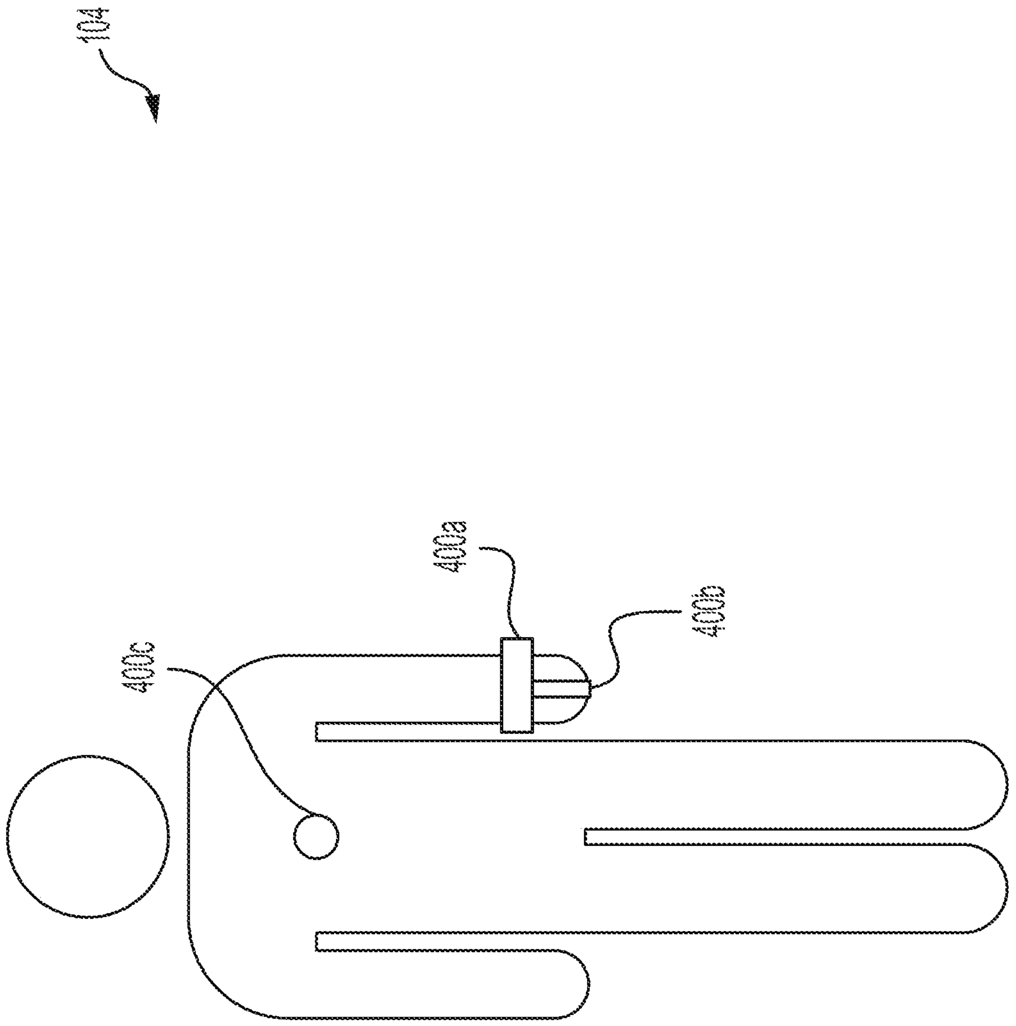
FIG. 4 shows an example diagram of a MD, according to some embodiments.

Referring now to FIG. 4, FIG. 4 shows an example diagram of MD 104, according to some embodiments. As shown in FIG. 4, MD 104 may include wrist-worn portion 400*a*, finger probe portion 400*b*, and/or chest probe portion 400*c*. In some embodiments, the one or more physiological sensors 302 of MD 104 may include a PPG sensor configured to be bodily-attached to a portion of the patient's body and sense an arterial pulse of the patient (e.g., in finger probe portion 400*b*). The one or more physiological sensors 302 (e.g., the PPG sensor, etc.) may be configured to apply a substantially uniform subdiastolic pressure to a portion of the patient's body while sensing an arterial pulse as a peripheral arterial signal of the patient. For example, a peripheral arterial signal may rise and fall with changes in the patient's sympathetic nervous system and may be linked to an oxygen saturation signal, actigraphy, and a snore microphone via a breathing disturbance index. As an example, the peripheral arterial signal may be based on a plethysmographic technique that uses a pneumo-optical sensor for the continuous measurement of the digital arterial pulse wave volume. As described in more detail herein, pneumo-optical sensor, which may include a finger sensor, may apply a uniform, subdiastolic pressure field to a distal two thirds of the finger and fingertip that (1) clamps the probe to the finger, (2) facilitates the unloading of arterial wall tension, which increases the dynamic range of the PAT signal, and/or (3) inhibits or prevents distal venous pooling and distention to avoid the induction of venoarterial-mediated vasoconstriction. Accordingly, attenuation of the peripheral arterial signal may reflect digital vasoconstriction and increased sympathetic nerve activity and can serve as a marker for arousal from sleep. The peripheral arterial signal may also detect the peripheral vasoconstriction associated with REM sleep.

As such, the one or more portions of the patient's body may include one or more of a finger of the patient, a wrist of the patient, a toe of the patient, a lower arm of the patient, an upper arm of the patient, and/or a hand of the patient. As an example, the one or more physiological sensors 302 may include a finger probe including a pneumo-optical sensor. The pneumo-optical sensor may include the PPG sensor configured to be utilized in conjunction with a pressure device configured to apply the uniform subdiastolic pressure to the portion of the patient's body. For example, the pneumo-optical sensor may be configured to apply the uniform subdiastolic pressure to a distal two-thirds of the finger and fingertip of the patient's finger. In such an example, the uniform subdiastolic pressure may be configured to one or more of: clamp the finger probe to the patient's finger, facilitate unloading of arterial wall tension, facilitate increase in a dynamic range of a peripheral arterial signal of the patient relative to PPG signals without the uniform subdiastolic pressure, and/or mitigate distal venous pooling or distention to avoid induction of venoarterial-mediated vasoconstriction.

In some embodiments, MD 104 may include (e.g., in wrist-worn portion 400*a*, in finger probe portion 400*b*, and/or in chest probe portion 400*c*) at least one other physiological sensor, such as at least one of a heart rate sensor, an oxygen saturation sensor, an actigraphy sensor, a snoring sensor, a chest motion sensor, a body position sensor, an arm position sensor, a sleep stage sensor, a PPG sensor, any combination thereof, and/or the like. Processor 306 may be operatively connected to the pneumo-optical sensor and/or the at least one other physiological sensor. For example, processor 306 may be configured to receive peripheral arterial signals and/or data from the peripheral arterial sensor and/or physiological data from the at least one other physiological sensor. Additionally, processor 306 may be configured to communicate the peripheral arterial signals and/or data and/or the physiological data to a remote computer system. In some embodiments, MD 104 may include a finger PPG sensor (e.g., in finger probe portion 400*b*). For example, MD 104 may include the finger PPG sensor in addition to or in lieu of a pneumo-optical sensor.

Figure 5:
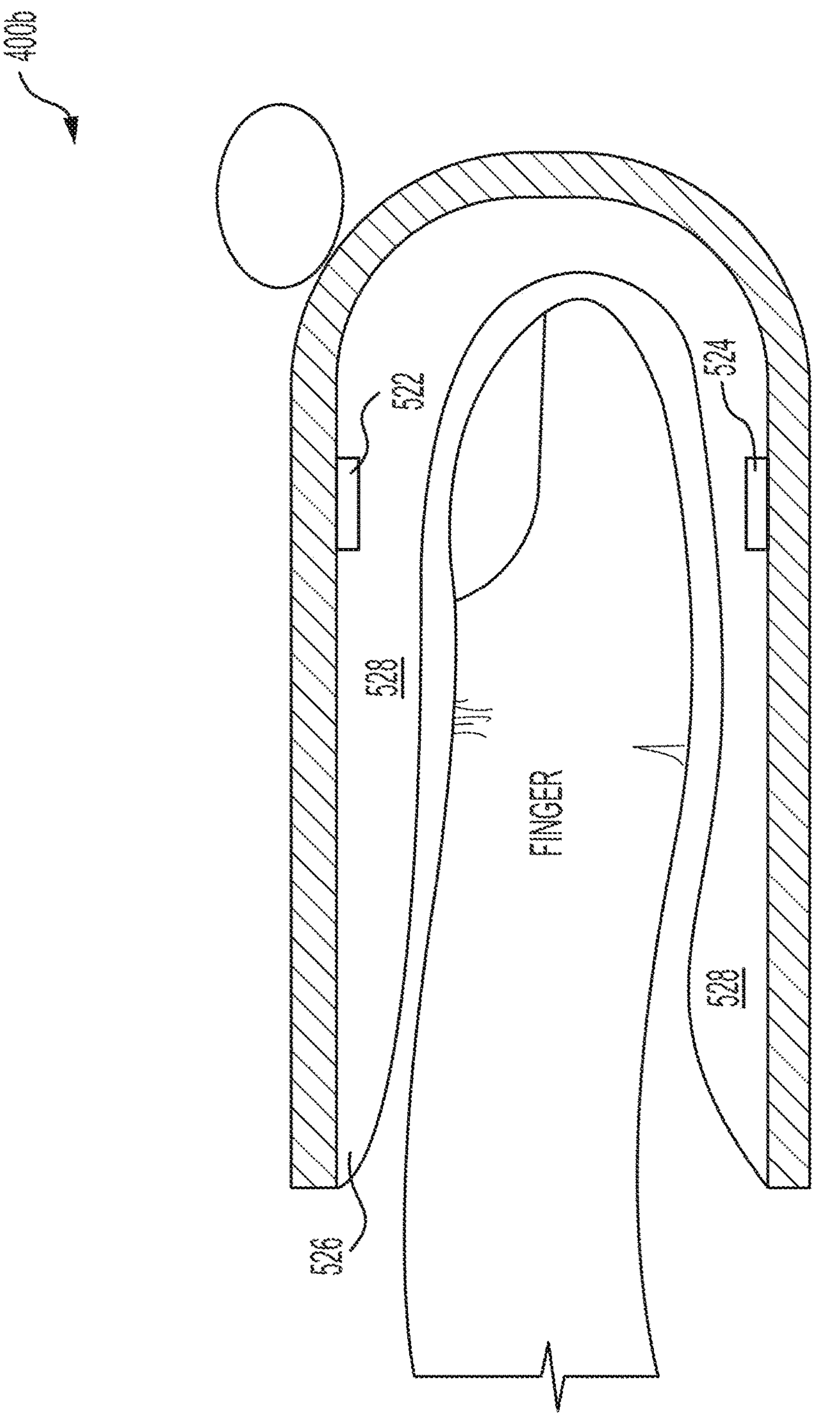
FIG. 5 shows an example diagram of a finger probe portion of a MD, according to some embodiments.

Referring now to FIG. 5, FIG. 5 shows an example diagram of finger probe portion 400*b* of MD 104, according to some embodiments. As shown in FIG. 5, finger probe portion 400*b* may be tubular, with a closed end and an open end, such that, when a patient's finger is placed therein, a distal part of the finger (e.g., the fingertip) is closest to the closed end, and a proximal part of the finger is closest to the open end of finger probe portion 400*b*.

As previously described herein, finger probe portion 400*b* may include a pneumo-optical sensor, which may include light emitting device 522 and light detecting device 524. For example, light emitting device 522 may include at least one of a light emitting diode (LED), a photoemitter, a laser, any combination thereof, and/or the like. Light detecting device 524 may include at least one of a photodiode, a photodetector, a photosensor, a photoresistor, a semiconductor based photodetector, any combination thereof, and/or the like. In some embodiments, light emitting device 522 may have a wavelength of about 550 nm (e.g., substantially visible green), about 650 nm (e.g., substantially visible red), 660 nm, about 780 nm (e.g., substantially infrared), 800 nm, 910 nm, 940 nm, and/or the like.

In some embodiments, finger probe portion 400*b* may include at least one other physiological sensor (not pictured) as described herein.

In some embodiments, finger probe portion 400*b* may include a plurality of light emitting devices 522. For example, each respective light emitting device 522 may have a respective wavelength. In some embodiments, the respective wavelength of each respective light emitting device 522 may be different than the wavelengths of at least some of (e.g., all of) the other light emitting devices 522. For example, a first light emitting device 522 may have a first wavelength (e.g., about 650 nm, about 660 nm, and/or the like) and a second light emitting device 522 may have a second wavelength (e.g., about 550 nm). In some embodiments, a single light detecting device 524 may detect light from all light emitting devices 522. In some embodiments, finger probe portion 400*b* may include a plurality of light detecting devices 524, each respective light detecting device 524 corresponding to (e.g., configured to detect the respective wavelength of) a wavelength of at least one of the light emitting devices 522.

In some embodiments, an inner portion of finger probe portion 400*b* may include a uniform pressure field. For example, a uniform pressure field may be achieved by inserting clastic member 526 into the open end of finger probe portion 400*b* and attaching clastic member 526 to the open end of finger probe portion 400*b* such that an enclosed seal is formed between an inner portion of finger probe portion 400*b* and elastic member 526 to define pocket 528. A fluid (such as an inert gas) may be inserted (e.g., injected and/or the like) into pocket 528 and cause clastic member 526 to elastically deform. For example, the pneumo-optical sensor may be utilized in conjunction with elastic member 526 to apply the uniform subdiastolic pressure to the portion of the patient's body (e.g., to a distal two-thirds of the finger and fingertip of the patient's finger, etc.), whereby the uniform subdiastolic pressure may one or more of: clamp the finger probe to the patient's finger, facilitate unloading of arterial wall tension, facilitate increase in a dynamic range of a peripheral arterial signal of the patient relative to PPG signals without the uniform subdiastolic pressure, and/or mitigate distal venous pooling or distention to avoid induction of venoarterial-mediated vasoconstriction.

In some embodiments, the uniform pressure field may be static and, when utilized in conjunction with light emitting device 522 and light detecting device 524, may produce a peripheral arterial signal or measurement.

In some embodiments, in order to apply finger probe portion 400*b* to an appendage, such as a finger, pressure (e.g., the uniform pressure field) may be applied so that finger probe portion 400*b* does not move. Additionally or alternatively, an adhesive may be used to secure finger probe portion 400*b* in place, and/or positioning members may attach finger probe portion 400*b* to a wristband, a watch band, and/or the like (e.g., to wrist-worn portion 400*a*, etc.).

In some embodiments, a uniform pressure field may be static and/or may inhibit or prevent pooling of venous blood in the distal end of a finger while allowing pulsatile blood delivered by the arteries to be returned via the veins. In some embodiments, the pressure applied by the uniform pressure field may be sufficient to prevent free venous flow due to, for example, hydrostatic pressure and shock waves, while allowing the veins to carry blood delivered by the arteries out of the finger. In some embodiments, the pressure required to prevent venous pooling may differ from patient to patient.

In some embodiments, noise reduction (e.g., improved signal to noise ratio) in the peripheral arterial signal or measurement may be achieved by applying sufficient pressure to partially unload, but not occlude, the wall tension of the arteries in the finger, when the finger is near heart level. This may allow the arterial wall to move freely to accommodate the pulsatile blood delivery of the heart. The applied pressure may be slightly above the maximum pressure in the veins when the hand is fully lowered (e.g., 5% higher and/or the like).

Figure 6:
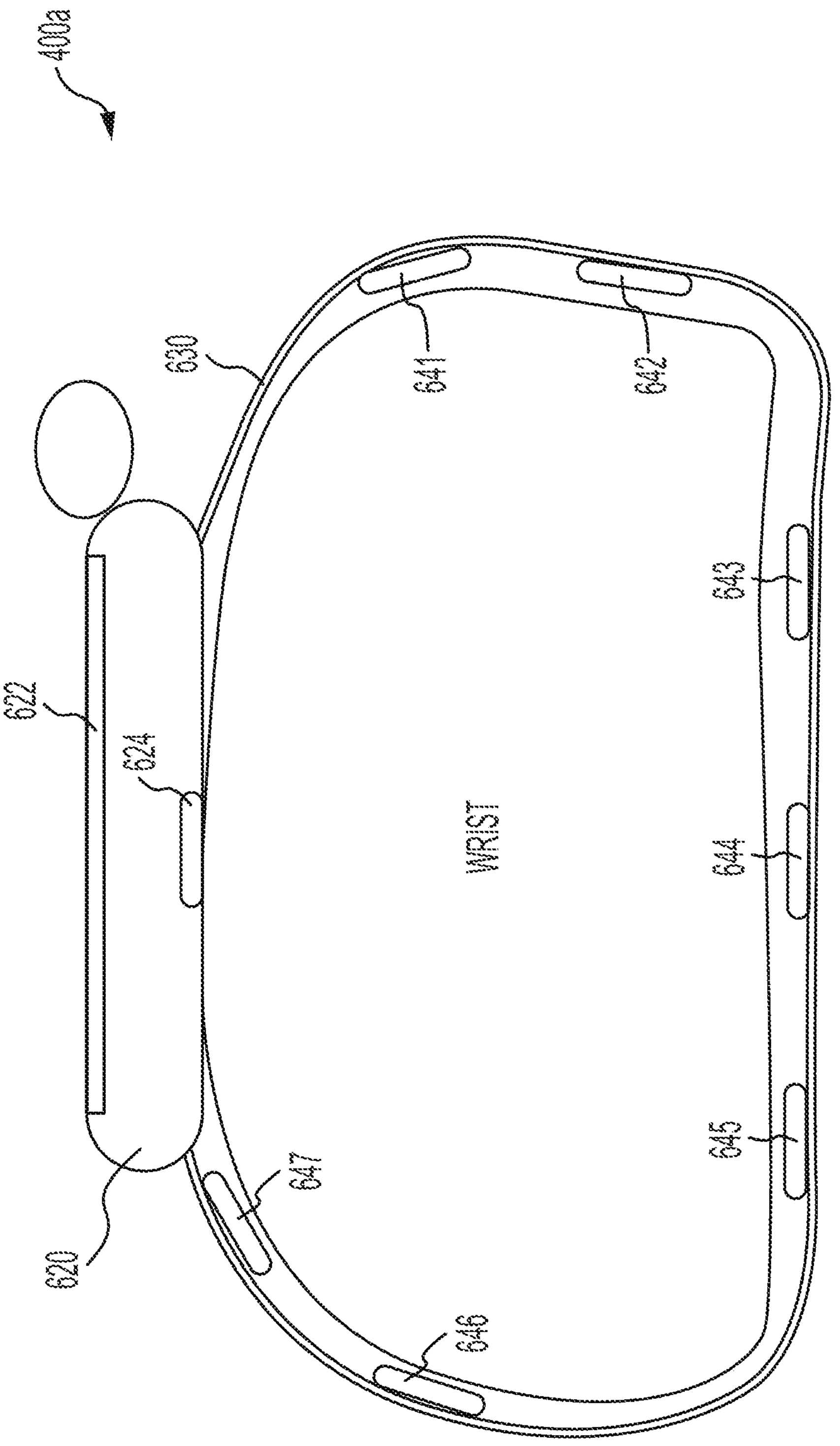
FIG. 6 shows an example diagram of wrist-worn portion of a MD, according to some embodiments.

Referring now to FIG. 6, FIG. 6 shows an example diagram of wrist-worn portion 400*a* of MD 104, according to some embodiments. As shown in FIG. 6, wrist-worn portion 400*a* may be may be worn on (e.g., encircle) a patient's wrist. For example, wrist-worn portion 400*a* may include a computing device 620 attached to a strap 630. In some embodiments, computing device 620 may include display 622.

In some embodiments, wrist-worn portion 400*a* may include at least one sensor. For example, wrist-worn portion 400*a* may include sensor 624. In some embodiments, sensor 624 may include at least one PPG sensor, which may include at least one light emitting device (e.g., a photoemitter) and at least one light detecting device (e.g., a photodetector), as described herein. For example, sensor 624 may include a plurality of light emitting devices (e.g., 3 light emitting devices having different wavelengths) and a light detecting device (e.g., configured to detect light of each wavelength of the light emitting devices), as described herein.

In some embodiments, wrist-worn portion 400*a* (e.g., computing device 620 thereof) may further include at least one other physiological sensor, such as at least one of a heart rate sensor, an oxygen saturation sensor, an actigraphy sensor (e.g., an accelerometer), an arm position sensor, a sleep stage sensor, an accelerometer, an electrode, a gyroscope, any combination thereof, and/or the like, as described herein.

In some non-limiting embodiments, wrist-worn portion 400*a* (e.g., computing device 620 thereof) may further include a communication interface, as described herein. In some embodiments, the communication interface may enable the computing device 620 to communicate with a communication network and/or a gateway device, as described herein.

In some embodiments, wrist-worn portion 400*a* may include (e.g., computing device 620 may be coupled to) a plurality of additional sensors 641-647. For example, each of additional sensors 641-647 may include a PPG sensor (e.g., including a light emitting device and a light detecting device, as described herein). In some embodiments, while eight total sensors (e.g., sensor 624 and additional sensors 641-647) are depicted, any suitable number of sensors may be included in wrist-worn portion 400*a*, such as 10 sensors, 18 sensors, 20 sensors, and/or the like. In some embodiments, additional sensors 641-647 may be dispersed along strap 630. For example, additional sensor 644 may be located opposite sensor 624 (e.g., additional sensor 644 may be located medial to sensor 624, which may be located lateral to first measurement device 644). Additionally or alternatively, additional sensor 641 may be located opposite additional sensor 646 (e.g., additional sensor 641 may be located anterior to additional sensor 646, which may be located posterior to additional sensor 641). In some embodiments, dispersing additional sensors 641-647 allows generation of a plurality of PPG signals from different sites, as described herein. Utilizing a plurality of PPG signals from different sites allows selecting at least a subset of PPG signals, as described herein.

In some embodiments, display 622 of computing device 620 may be configured to render content on the display 622. For example, display 622 may render first content in response to detecting an SDB event based on PPG data. Additionally or alternatively, display 622 may render second content displaying continuous measurements, such as heart rate, oxygen saturation, device status, time (e.g., as a watch), any combination thereof, and/or the like. Additionally or alternatively, display 622 may render third content displaying a status of an initialization or configuration process of MD 104, such as information relating to a burning-in of a unique medical device identifier to MD 104 that causes the uninitialized medical device to be uniquely addressable, information relating to setting one or more monitoring and/or treatment parameters and/or thresholds, information relating to execution of one or more hardware and/or software tests of MD 104, information relating to an initialization status of MD 104 (e.g., uninitialized, initialized, etc.), any combination thereof, and/or the like.

In some embodiments, chest probe portion 400*c* may include at least one sensor. For example, chest probe portion 400*c* may include a chest motion sensor configured to be disposed on an upper chest area of the patient. The chest motion sensor may include one or more of a snoring microphone, a vibration sensor, or an accelerometer, e.g., configured to monitor for chest wall motion/movement, respiration motion, body position (e.g., upright, supine, lying-on-left-side, lying-on-right-side, etc.). Additionally or alternatively, chest probe portion 400*c* may include one or more of ECG electrodes and a body impedance sensor. In some embodiments, chest probe portion 400*c* may further include at least one other physiological sensor, such as at least one of an ECG-based or PPG-based heart rate sensor, an oxygen saturation sensor, a gyroscope, any combination thereof, and/or the like, as described herein.

In some embodiments, wrist-worn portion 400*a* may include one or more of wireless communications circuitry 304, processor 306, buffer 308, voltage receiving circuitry 310, SoC 314 any combination thereof, and/or the like, as described herein. In some embodiments, finger probe portion 400*b* may include one or more of wireless communications circuitry 304, processor 306, buffer 308, voltage receiving circuitry 310, SoC 314 any combination thereof, and/or the like, as described herein. In some embodiments, chest probe portion 400*c* may include one or more of wireless communications circuitry 304, processor 306, buffer 308, voltage receiving circuitry 310, SoC 314 any combination thereof, and/or the like, as described herein.

Wireless communication network 106 may include one or more wired and/or wireless networks. For example, wireless communication network 106 may include a cellular communication network, a Bluetooth communication network, Advanced Message Queuing Protocol (AMQP) communication network, Constrained Application Protocol (CoAP) connection, a Wi-Fi communication network, a ZigBee communication network, a Z-Wave communication network, a wireless personal area network (WPAN) communication network, an Infrared Data Association (IrDA) communication network, any combination thereof, and/or the like. For example, wireless communication network 106 may be established between EPD 102 and MD 104 based on a voltage-based index value.

Returning again to FIG. 1B, configuration system 120 may include one or more devices capable of receiving information from and/or communicating information to EPD 102 (e.g., via one or more wired and/or wireless communication connections). In some embodiments, configuration system 120 may include a server, a group of servers, and/or other like devices, as described herein. Additionally or alternatively, configuration system 120 may include at least one other computing device separate from or including the server and/or group of servers, such as a portable and/or handheld device (e.g., a computer, a laptop, a personal digital assistant (PDA), a smartphone, a tablet, and/or the like), a desktop computer, and/or other like devices, as described herein. In some embodiments, configuration system 120 may include at least one network interface (e.g., a server network interface and/or the like), at least one data storage device (e.g., a server database and/or the like), at least one processor (e.g., a server processor and/or the like), any combination thereof, and/or the like. For example, configuration system 120 may include at least one processor operatively connected to a non-transitory computer-readable medium, as described herein. In some embodiments, configuration system 120 may be in communication with at least one data storage device (e.g., a server database and/or the like), which may be local or remote to configuration system 120. In some embodiments, configuration system 120 may be capable of receiving information from, storing information in, communicating information to, or searching information stored in the data storage device (e.g., a server database and/or the like).

In some embodiments, configuration system 120 may be configured to control the plurality of EPDs 102*a*, 102*b*, . . . 102*n* for configuring or initializing the plurality of MDs 104*a*, 104*b*, . . . 104*n*. For example configuration system 120 may be configured to generate and/or designate a different voltage-based index value for each of the plurality of EPDs 102*a*, 102*b*, 102*n*.

The number and arrangement of systems, devices, and/or networks shown in FIGS. 1A-IF and 2-6 are provided as an example. There may be additional systems, devices, and/or networks; fewer systems, devices, and/or networks; different systems, devices, and/or networks; and/or differently arranged systems, devices, and/or networks than those shown in FIGS. 1A, 1B, and 2-6. Furthermore, two or more systems or devices shown in FIGS. 1A-1F and 2-6 may be implemented within a single system or device, or a single system or device shown in FIGS. 1A-IF and 2-6 may be implemented as multiple, distributed systems or devices. Additionally or alternatively, a set of systems (e.g., one or more systems) or a set of devices (e.g., one or more devices) of system 100 may perform one or more functions described as being performed by another set of systems or another set of devices of system 100.

Figure 7A:
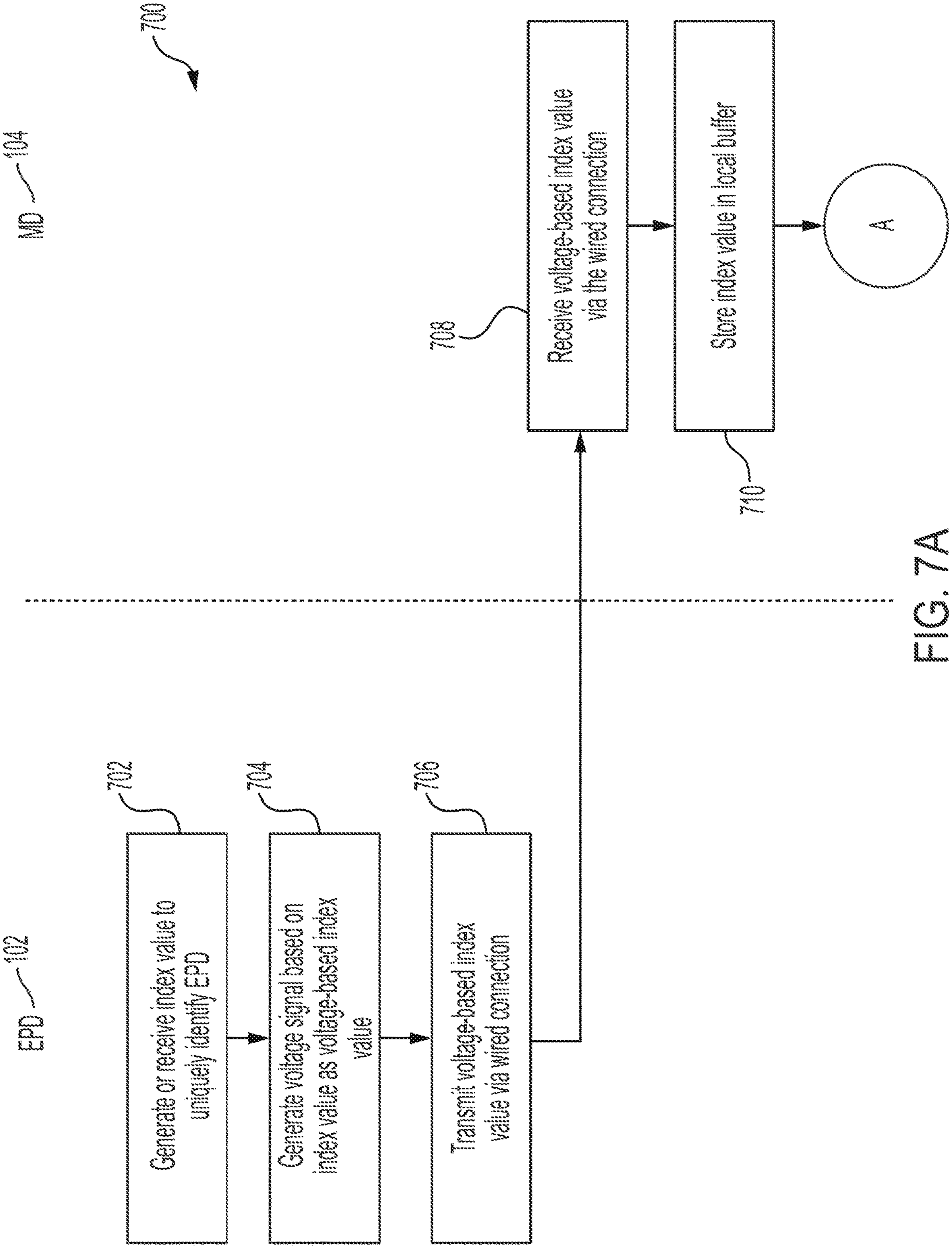
FIGS. 7A-7C are an example flowchart of a process for initializing medical devices, according to some embodiments.
Figure 7B:
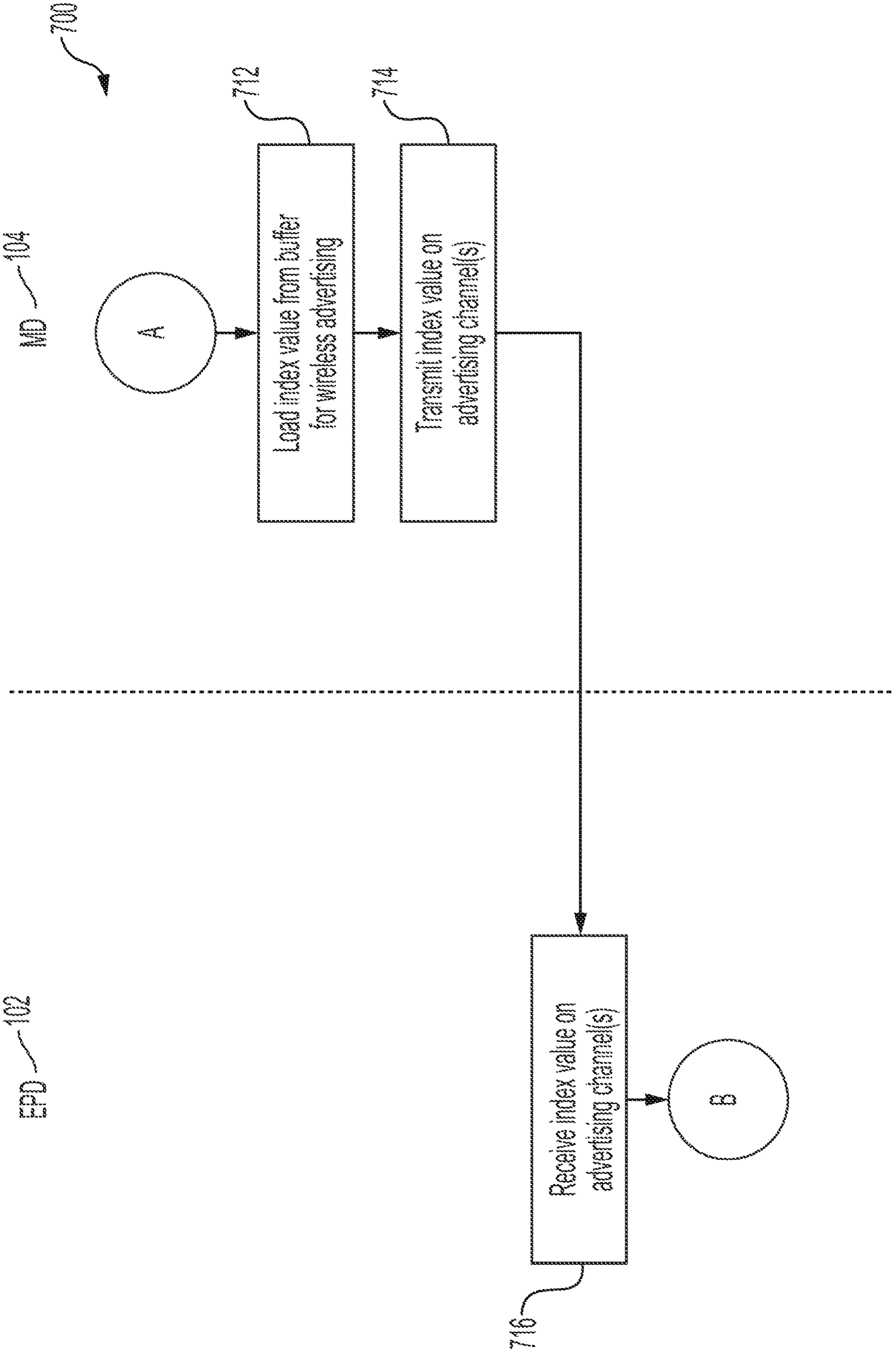
Figure 7C:
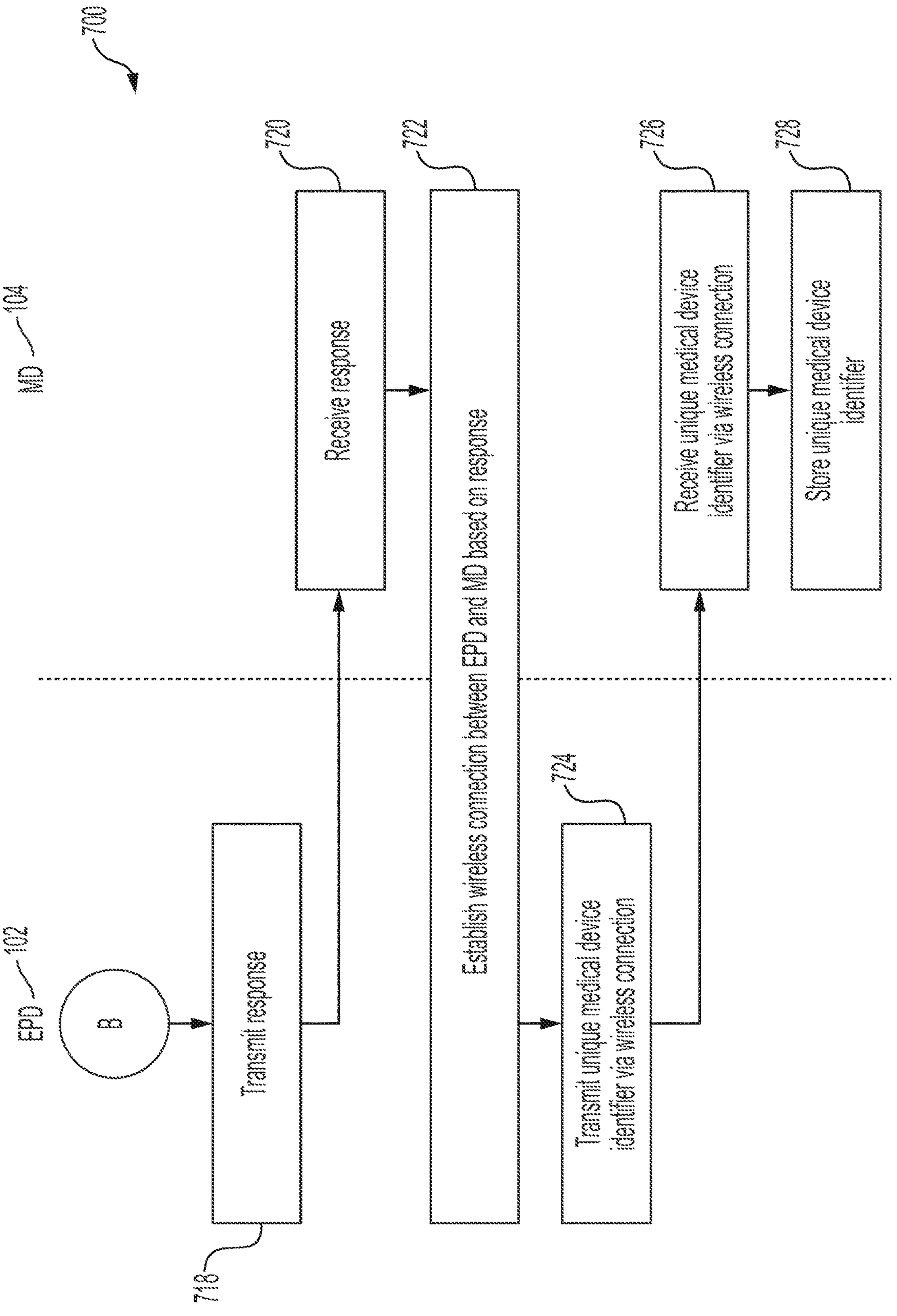

Referring now to FIGS. 7A-7C, FIGS. 7A-7C show an example flowchart of a process 700 for initializing medical devices, according to some embodiments. In some embodiments, one or more of the steps of process 700 may be performed (e.g., completely, partially, and/or the like) by EPD 102. In some non-limiting embodiments, one or more of the steps of process 700 may be performed (e.g., completely, partially, and/or the like) by another system, another device, another group of systems, or another group of devices, separate from or including EPD 102, such as MD 104, configuration system 120, and/or the like. The steps shown in FIGS. 7A-7C are for example purposes only. It will be appreciated that additional, fewer, different, and/or a different order of steps may be used in some embodiments.

As shown in FIG. 7A, at step 702, process 700 may include generating or receiving an index value to uniquely identify an EPD. For example, EPD 102 may generate or receive an index value to uniquely identify EPD 102. As an example, index generation circuitry 204 of EPD 102 may generate the index value based on a predetermined input to index generation circuitry 204. In such an example, user interface 210 (e.g., a touch screen display, a keyboard, a keypad, a mouse, a button, a switch, a microphone, a camera, input component 810, and/or the like) may receive a user input and produce the predetermined input to index generation circuitry 204 based on the user input. The user input may include an index value that uniquely identifies EPD 102 and/or a wireless communication network associated with EPD 102 (e.g., a Bluetooth address, a Wi-Fi service set identifier (SSID), etc.).

As shown in FIG. 7A, at step 704, process 700 may include generating a voltage signal based on the index value as a voltage-based index value. For example, EPD 102 may generate a voltage signal based on the index value as a voltage-based index value. As an example, voltage generation circuitry 150 of index generation circuitry 204 of EPD 102 may generate the voltage signal as a predetermined supply voltage associated with the index value and/or the voltage signal as varying voltages between two predefined voltage levels to encode the index value in the voltage signal.

As shown in FIG. 7A, at step 706, process 700 may include transmitting the voltage-based index value via a wired connection. For example, EPD 102 may transmit the voltage-based index value via wired connection 108. As an example, MD 104 may include an uninitialized medical device of a plurality of uninitialized medical devices. In such an example, electrical adapter terminals 206 of EPD 102 may be connected to electrical battery terminals 312 of MD 104 to create wired connection 108. As an example, power line communication system 175 of EPD 102 modulate the index value on a power supply provided to MD 104 from EPD 102 via wired connection 108.

As shown in FIG. 7A, at step 708, process 700 may include receiving the voltage-based index value via the wired connection. For example, MD 104 may receive the voltage-based index value via wired connection 108. As an example, voltage receiving circuitry 310 of MD 104 may receive the voltage signal and determine, based on the voltage signal, the index value that identifies the external programming device. In such an example, voltage receiving circuitry 310 may determine the index value as a binary sequence.

As shown in FIG. 7A, at step 710, process 700 may include storing the index value in a local buffer. For example, MD 104 may store the index value in a local buffer (e.g., buffer 308, etc.). As an example, voltage receiving circuitry 310 may store the binary sequence of bits in buffer 308.

As shown in FIG. 7B, at step 712, process 700 may include loading the index value from the local buffer for wireless advertising. For example, MD 104 may load the index value from the local buffer (e.g., buffer 308, etc.) for wireless advertising (e.g., for Bluetooth or BLE advertising, etc.). As an example, processor 306 of MD 104 may load the binary sequence of bits from buffer 308 as the index value for wireless advertising.

As shown in FIG. 7B, at step 714, process 700 may include transmitting the index value on one or more advertising channels. For example, MD 104 may transmit the index value on one or more advertising channels (e.g., one or more BLE channels, etc.). As an example, MD 104 may transmit the index value on one or more of BLE channels 37, 38, and 39 used for the initial exchange of advertising packets.

For communication, the BLE protocol employs a predetermined set of data channels. For example, the protocol includes 40 physical data channels, which range in number from 0 to 39, and are separated from one another by 2 MHz in the 2.4 GHz frequency range. Frequency hopping is a technique used by BLE to reduce interference and boost dependability. This technique avoids using channels that are experiencing interference by having the transmitter and receiver rapidly switch channels in a pseudo-random order. For implementations herein, a BLE connection can be first established by EPD 102 and MD 104 by exchanging advertising packets, which are used to broadcast details about EPD 102. The devices transition to a different set of channels, known as the data channels, which are used once a connection request has been made.

Figure 8:
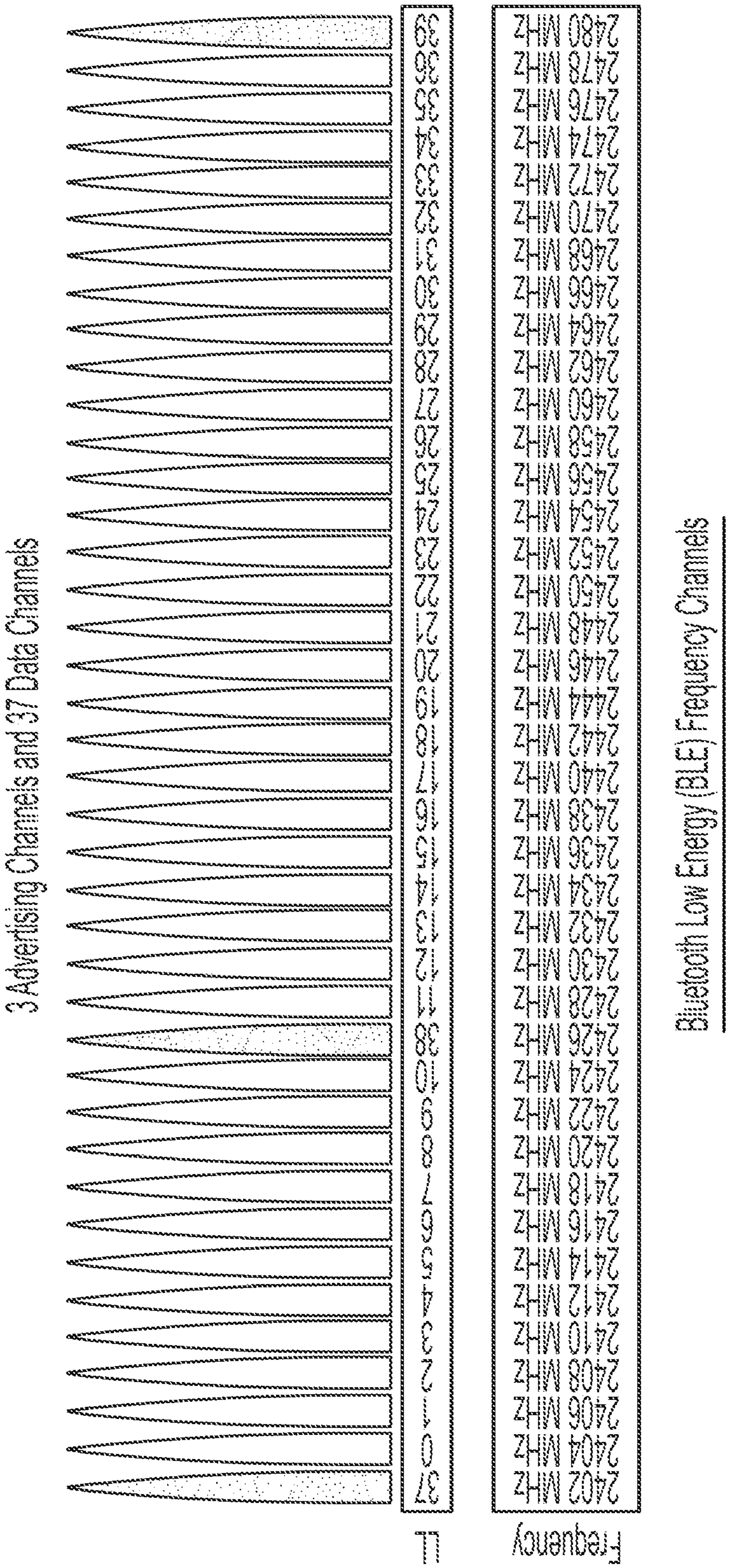
FIG. 8 shows the mapping between frequencies and Bluetooth Low Energy (LE) channels.

The Bluetooth LE system operates in the 2.4 GHZ ISM band at 2400-2483.5 MHz. It uses 40 RF channels (each channel is 2 MHz wide). FIG. 8 shows the mapping between the frequencies and Bluetooth LE channels. Each of these RF channels is allocated a unique channel index (labeled as channel in the figure).

As shown in FIG. 7B, at step 716, process 700 may include receiving the index value on the one or more advertising channels. For example, EPD 102 may receive the index value on the one or more advertising channels (e.g., the one or more BLE channels, etc.). As an example, EPD 102 may receive the index value on the one or more of BLE channels 37, 38, and 39 used for the initial exchange of advertising packets.

In examples, certain advertising channels (e.g., channels 37, 38, and 39) of the BLE protocol can be used for the initial exchange of advertising packets. The data channels (0 to 36) can be used for actual data transmission once the connection has been established. In one implementation, to use the index string from the local buffer to establish a BLE connection to another device, MD 104 can send a connection request packet to EPD 102 (e.g., the target device). In some example implementations, the connection request packet can include the index string as part of the data payload. EPD 102 can extract the index string from the payload of the connection request packet and confirm that the index string is genuine (e.g., using a predefined authentication process). While in this example the MD 104 is described as sending a connection request, in some examples, the MD 104 can be configured to send advertising packets which are received at the EPD 102. In these examples, when the EPD 102 receives the advertising packets, the MD 104 can respond by initiating the connection request.

As shown in FIG. 7C, at step 718, process 700 may include transmitting a response. For example, EPD 102 may transmit a response. As an example, EPD 102 can send a response packet indicating that EPD 102 is prepared to establish a BLE connection if the index value is correct and corresponds to a MD 104 that is authorized to connect to the EPD 102. For example, EPD 102 as the target device knows its own index value identifying EPD 102 and as such is able to authenticate the request. Also, one of the data channels can be used to send the response packet.

As shown in FIG. 7C, at step 720, process 700 may include receiving the response. For example, MD 104 may receive the response. As an example, MD 104 may receive the response packet indicating that EPD 102 is prepared to establish a BLE connection.

As shown in FIG. 7C, at step 722, process 700 may include establishing a wireless connection between an EPD and a MD based on the response. As an example, assuming the device processor gets a legitimate response packet, MD 104 can connect to EPD 102 via BLE on one of the data channels. The two devices can communicate and share data once the BLE connection has been made. Specific data channel frequency bands that can be used may depend on the implementation of the BLE protocol.

In an alternate scheme, when establishing a BLE connection, MD 104 and EPD 102 may first exchange advertising packets, which are used to broadcast information about the devices. To include the index value in the connection request, the MD processor can append the index string to a value that is transmitted in the advertising packets. EPD 102 can then extract the index value from the received advertising packets and use it to verify that the connection request is legitimate. For example, the MD processor may include the index value as part of the device name in the advertising packets. The advertising packets are transmitted on the primary advertising channels (37, 38, and 39) and are spaced 2 MHz apart in the 2.4 GHz frequency band. When EPD 102 receives the advertising packets, EPD 102 can extract the MD name and parse out the index string. EPD 102 can verify that the index string is valid and corresponds to a device that is allowed to connect. Once EPD 102 has verified the index value, EPD 102 can send a response packet indicating that EPD 102 is ready to establish a BLE connection. The response packet can also include the index string as part of the data payload, which the MD processor can use to verify that the response is legitimate. Assuming the MD processor receives a valid response packet, MD 104 can establish a BLE connection with the target device on one of the data channels, which are used for actual data transmission once the connection has been established. The specific implementation of this scenario may vary. For example, the MD processor can be configured to ensure that the index value is correctly formatted and appended to the correct value in the advertising packets. EPD 102 can implement additional security measures to prevent unauthorized access. Additionally, the specific data channel frequency bands used may depend on the frequency-hopping scheme used by the devices.

As shown in FIG. 7C, at step 724, process 700 may include transmitting a unique medical device identifier via the wireless connection. For example, EPD 102 may transmit, via the wireless connection between EPD 102 and MD 104 (e.g., via a Bluetooth connection, etc.), a unique medical device identifier to MD 104 that causes MD 104 to be uniquely addressable. As an example, EPD 102 may transmit the unique medical device identifier to MD 104 via BLE on one of the data channels.

In some embodiments, EPD 102 may program, via the wireless connection between EPD 102 and MD 104, one or more monitoring and/or treatment parameters and/or thresholds of MD 104 for use in operation of MD 104, as described in more detail herein.

As shown in FIG. 7C, at step 726, process 700 may include receiving the unique medical device identifier via the wireless connection. For example, MD 104 may receive, via the wireless connection (e.g., via wireless communication network 106, etc.) between EPD 102 and MD 104, a unique medical device identifier that causes MD 104 to be uniquely addressable. As an example, MD 104 may receive the unique medical device identifier from EPD 102 via BLE on one of the data channels.

In some embodiments, MD 104 may receive, via the wireless connection between EPD 102 and MD 104, one or more monitoring and/or treatment parameters and/or thresholds of the uninitialized medical device for use in operation of the uninitialized medical device, as described in more detail herein.

As shown in FIG. 7C, at step 728, process 700 may include storing a unique medical device identifier. For example, MD 104 may store, in a non-volatile memory (e.g., memory 307, etc.), the unique medical device identifier to initialize MD 104 by causing MD 104 to be uniquely addressable, as described in more detail herein.

In some embodiments, MD 104 may execute one or more hardware and/or software built-in tests and transmit, via the wireless connection between EPD 102 and MD 104, a result of the one or more hardware and/or software built-in tests, as described in more detail herein.

Although described herein primarily with respect to an external programming device configured to transmit a voltage-based index value through a wired connection to an uninitialized medical device to uniquely identify the external programming device for establishing a wireless connection between the uninitialized medical device and the external programming device, described in further detail below are other systems, devices, methods, and computer program products for transmitting an index value to an uninitialized medical device. For example, EPD 102 may be configured to transmit an index value through a non-wired connection to one or more physiological sensors (and/or other sensors) of MD 104 and establish a wireless connection between EPD 102 and MD 104 based on the index value. As an example, MD 104 may be configured to receive, via a non-wired connection using the one or more physiological sensors (and/or other sensors), from EPD 102, the index value that identifies EPD 102 and establish a wireless connection between EPD 102 and MD 104 based on the index value.

Example non-wired connections can be based on accelerometer signals, e.g., using orientation or motion sensing or both. Example non-wired connections can be based on light signals. Example non-wired connections can be based on sound signals. Example non-wired connections can be based on pressure signals. Details of each of these examples are provided below.

Figure 9A:
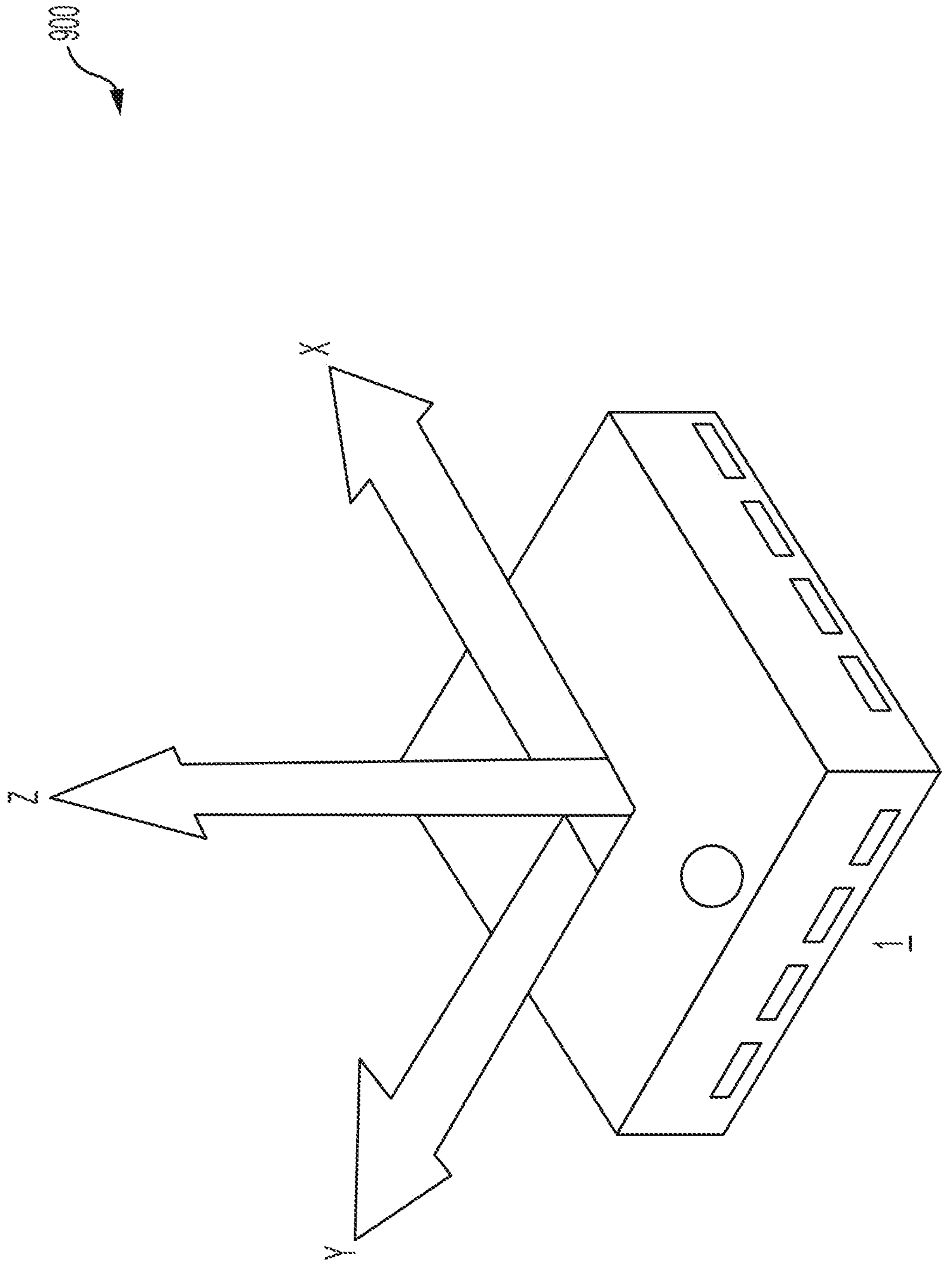
FIG. 9A shows three detected orthogonal axes of an accelerometer of a MD.
Figure 9B:
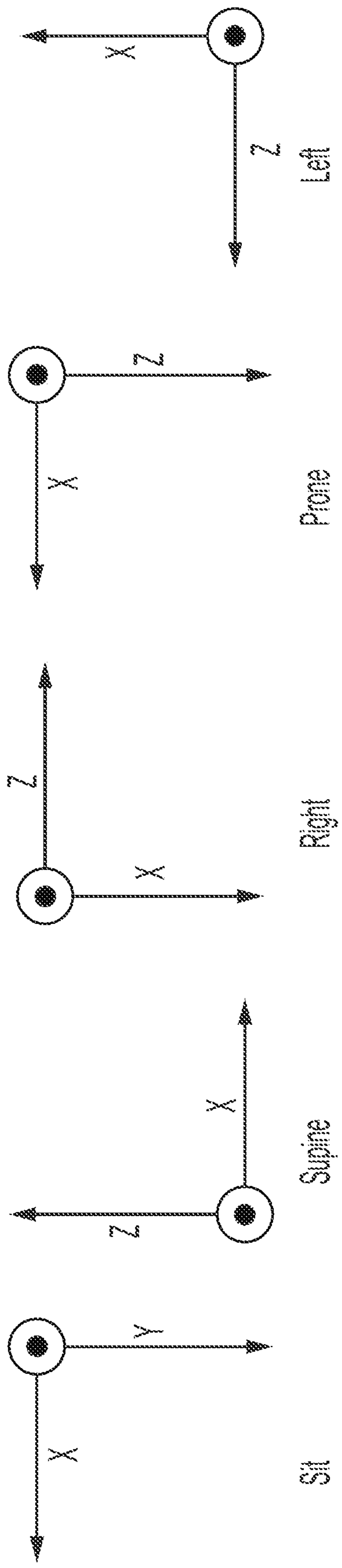
FIG. 9B shows an example of accelerometer's orientations at specific body postures.
Figure 9C:
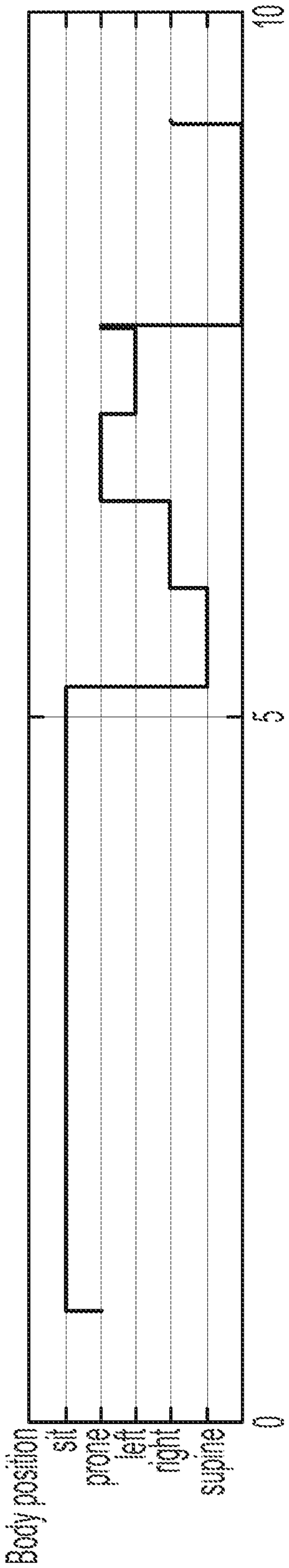
FIG. 9C shows an example plot of series of orientations or body postures along the time axis, representing an operation code.

Referring now to FIGS. 9A-9C, EPD 102 may be configured to transmit an index value via an orientation change of MD 104. For example, EPD 102 may include a serial or parallel manipulator robot configured to generate the index value that identifies EPD 102 as a modification of an orientation of MD 104. As an example, a microcontroller (e.g., SoC 314) in communication with an accelerometer 900 of MD 104. The microcontroller can be configured to analyze the MD's orientation, e.g., based on accelerometer 900 signals, and as such is configured to receive the index value via the orientation change (e.g., the index value may be encoded within the orientation change). In such an example, the accelerometer 900 provides the micro-controller (e.g., SoC 314, etc.) of MD 104 raw signals representing the gravity force on each of its three orthogonal axes of the geophysical axes system as shown in FIG. 9A, and the microcontroller may translate the raw data into orientation values. When included in and/or mounted onto MD 104, the accelerometer 900 may practically sense the orientation of the medical device in which the accelerometer 900 is embedded. The microcontroller of MD 104 may translate the raw signals from the accelerometer 102 into various device orientations (e.g., using a similar coding scheme as that for body postures). For example, such a scheme based on body postures is illustrated in FIG. 9B, including a left lateral posture, a right lateral posture, a sitting posture, a supine posture, a prone posture, an upside down posture, and/or the like.

As shown in FIG. 9C, a predefined sequence of MD's orientations can be used to instruct MD 104 to enter an initialization mode, a pre-programming mode, a production mode, or other such mode configured for initializing the uninitialized medical device and to code the index value to MD 104. For example, EPD 102 may manipulate MD 104 including accelerometer 900 (e.g., using a serial or parallel manipulator robot, etc.) in a series of orientations to communicate the index value to MD 104. As an example, a series of the following orientations may represent an operation code that instructs MD 104 to switch to an initialization mode: LEFT-RIGHT-LEFT-RIGHT-SIT-LEFT. EPD 102 may hold MD 104 at each orientation for a predetermined time period (e.g., 2 seconds, etc.) so that a series of readings can be averaged. MD 104 may constantly track the raw data stream from the accelerometer 900, calculating the sampled values.

Once MD 104 detects the orientation sequence that instructs MD 104 to switch to an initialization mode sequence, MD 104 enters into the initialization mode. When in the initialization mode, the microcontroller of MD 104 may interpret the stream of raw data from the accelerometer 900 as a stream of index values. The data stream may be composed of a repetition of the index word, delimited by one character. Each index word in this example can be created by two "characters" (a character being an orientation of the device). For example, if one orientation, such as the UPSIDE DOWN orientation, is used as a delimiter between words, 5 characters or orientations remain for use, which can create 25 different index words. If a wider range than 25 indices is used, a longer "word" can be used. For example, if a word is increased from a length of two to three, that enables 125 different indices numbers. The word's length can be as long as needed.

Many accelerometers have a good enough accuracy and range that more orientations, e.g., non-orthogonal orientations, can be used for the coding purposes. If more data needs to be transferred to MD 104 at a given time, more characters can be created based on various predetermined spatial angles of MD 104. Thus, with more characters available, within the same length of word more data can be transferred. For example, when also using non-orthogonal orientations beyond canonic orientations, a much larger variety of characters can be defined. In this example, when using a set of 20 spatial angles as characters, the coding of the index value itself may only consume 6-7 characters.

In some implementations, EPD 102 may be configured to transmit an index value via a specific vibration pattern. For example, EPD 102 may include a vibrator configured to generate the index value that identifies the external programming device as a vibration signal (e.g., a knocking on MD 104 may vibrate MD 104, etc.). As an example, a microcontroller (e.g., SoC 314) in communication with an accelerometer 900 of MD 104. The microcontroller can be configured to analyze the MD's orientation, e.g., based on accelerometer 900 signals, and as such is configured to receive the index value via the specific vibration pattern (e.g., the index value may be encoded within the specific vibration pattern). In such an example, the vibration may be manifested as a change in the values of the accelerometer 900. An amplitude of the changes in the values of the accelerometer may vary, based on different parameters, such as an amount of force used to knock or vibrate MD 104, a material used to knock or vibrate MD 104, a material of a stage on which MD 104 is placed during the knocking or vibration, and/or the like. These parameters may be adjusted to create an environment that allows as many distinct amplitudes as needed. The knocks or vibrations may then be used to switch MD 104 to the initialization mode and transmit the index value or word to MD 104.

In some embodiments, EPD 102 may be configured to transmit an index value to MD 104 via an optical signal. For example, EPD 102 may include an optical emitter configured to generate the index value that identifies EPD 102 as an optical signal. As an example, MD 104 may include an optical sensor (e.g., sensor 302, etc.) configured to receive the index value that identifies EPD 102 via the optical signal (e.g., the index value may be encoded within the optical signal).

Emitted light may be used to initialize MD 104. When MD 104 is powered-on, MD 104 may search for a specific pattern in a light intensity sensed by the optical sensor, and if a correct pattern is detected MD may automatically enter or switch to an initialization mode, otherwise MD 104 may stay in a normal or working mode.

Figure 10:
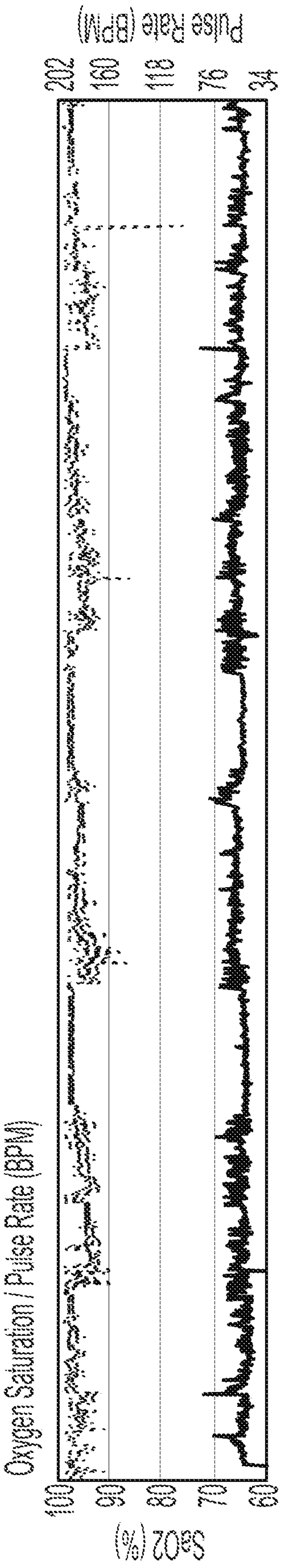
FIG. 10 shows an example plot of oxygen level in the blood and heart rate determined from a measured intensity of light.

When using a light source for the initialization, the optical emitter of EPD 102 may emit the light different intensities. For example, the optical sensor of MD 104 may include a photodiode that has high capabilities in measuring the intensity of its own emitted light at 3 different wavelengths, e.g., 660, 800 and 910 nm. As shown in FIG. 10, this measured intensity may be used by MD 104 to determine different clinical situations, such as the oxygen level in the blood and/or heart rate. In examples herein, such photodiode can be used for detecting MD 104 for the initialization process based on the sensed light intensity value used as the character, and with a sequence of characters used as a word or index value.

EPD 102 may include the optical emitter or a light source generator configured to emit light at several predefined intensity levels. EPD 102 may direct the emitted light at the photodiode of MD 104, which in some examples may be located in the inner chamber of the finger probe portion. The photodiode may generate a current flow according to the light intensity received. The microcontroller of MD 104 may receive and sample the current flow rates and determine intensity levels received by the photodiode. The microcontroller of MD 104 may translate the intensity levels to characters, and the characters to words. The words may be used to switch modes of MD 104, transmit the index value to MD 104, and/or the like.

In some embodiments, EPD 102 may be configured to transmit an index value to MD 104 via an audio signal. For example, EPD 102 may include a speaker configured to generate an index value (e.g., where the index value is configured as an identifier of the EPD 102) in the form of an audio output. As an example, MD 104 may include a microphone configured to receive the index value that identifies EPD 102 via the audio signal (e.g., the index value may be encoded within the audio signal).

Generated sounds may be used to initialize MD 104. When MD 104 is powered on, MD 104 may search for a specific pattern in an audio signal received by the microphone, and if a correct pattern is detected MD 104 may automatically enter or switch to a programming mode.

Figure 11:
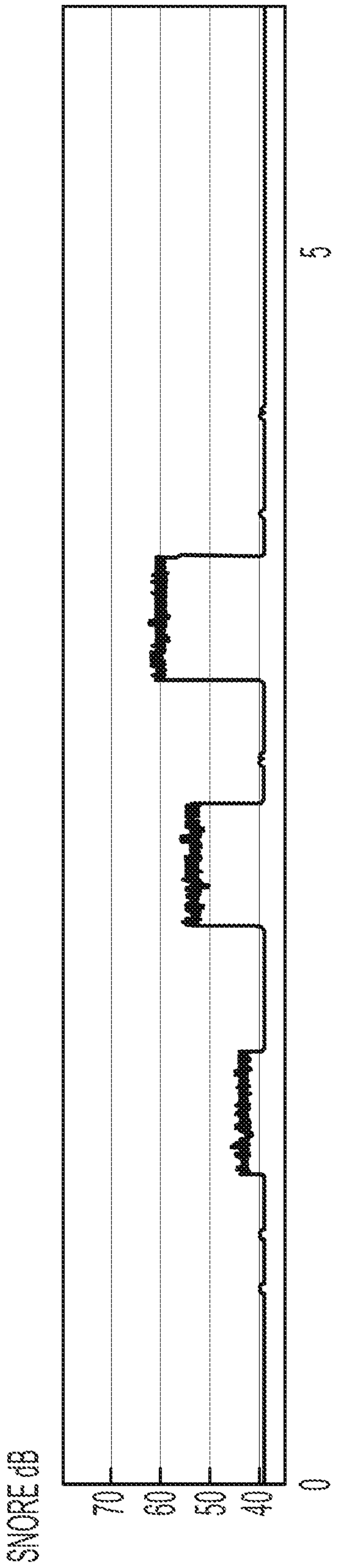
FIG. 11 shows an example plot of detected snoring sounds.

As shown in FIG. 11, a snoring sensor or microphone of MD 104 may be configured to detect snoring sounds in a range of 40 dB to 70 dB. For programming purposes, this range can be broken to a plurality of amplitudes, with each individual amplitude being a character. The size of the character set is based on the signal acquiring device's sensitivity. As shown in Table 2 below, 13 or more different example amplitudes (measured in dB) of white sound may recorded by MD 104, which enables an example data set of at least 13 characters.

TABLE 2

| | |
|---|---|
| 1 | 40.3 |
| 2 | 42.6 |
| 3 | 44.5 |
| 4 | 45.6 |
| 5 | 46.5 |
| 6 | 48.1 |
| 7 | 49.4 |
| 8 | 51.5 |
| 9 | 52.4 |
| 10 | 54.6 |
| 11 | 60.6 |
| 12 | 61.3 |
| 13 | 65.3 |

EPD 102 may include a sound wave generator or speaker configured to generate white sound signals at a plurality of predefined amplitude levels that may be picked up or received by the microphone of MD 104, which may be located in the chest sensor portion of MD 104. The microphone may generate a current flow or data stream according to the detected amplitude. The microcontroller of MD 104 may receive and sample the microphone data stream, determine the amplitudes received by the microphone, and convert the detected amplitudes into characters, and the characters into words. The words may then be used to instruct MD 104 to switch operating modes, transmit the index number to MD 104, and/or the like.

In some embodiments, EPD 102 may be configured to transmit an index value to MD 104 via a pressure signal. For example, EPD 102 may include a pressure generator configured to generate the index value that identifies EPD 102 as a pressure applied MD 104. As an example, MD 104 may include a pressure transducer (e.g., sensor 302, etc.) configured to receive the index value that identifies EPD 102 via a pressure signal.

Pressure changes can be used to initialize or program MD 104. When MD 104 is powered on, MD 104 may search for a specific pattern in the pressure changes, and if a specific pattern is detected, MD 104 may automatically enter or switch to a programming mode.

Figure 12A:
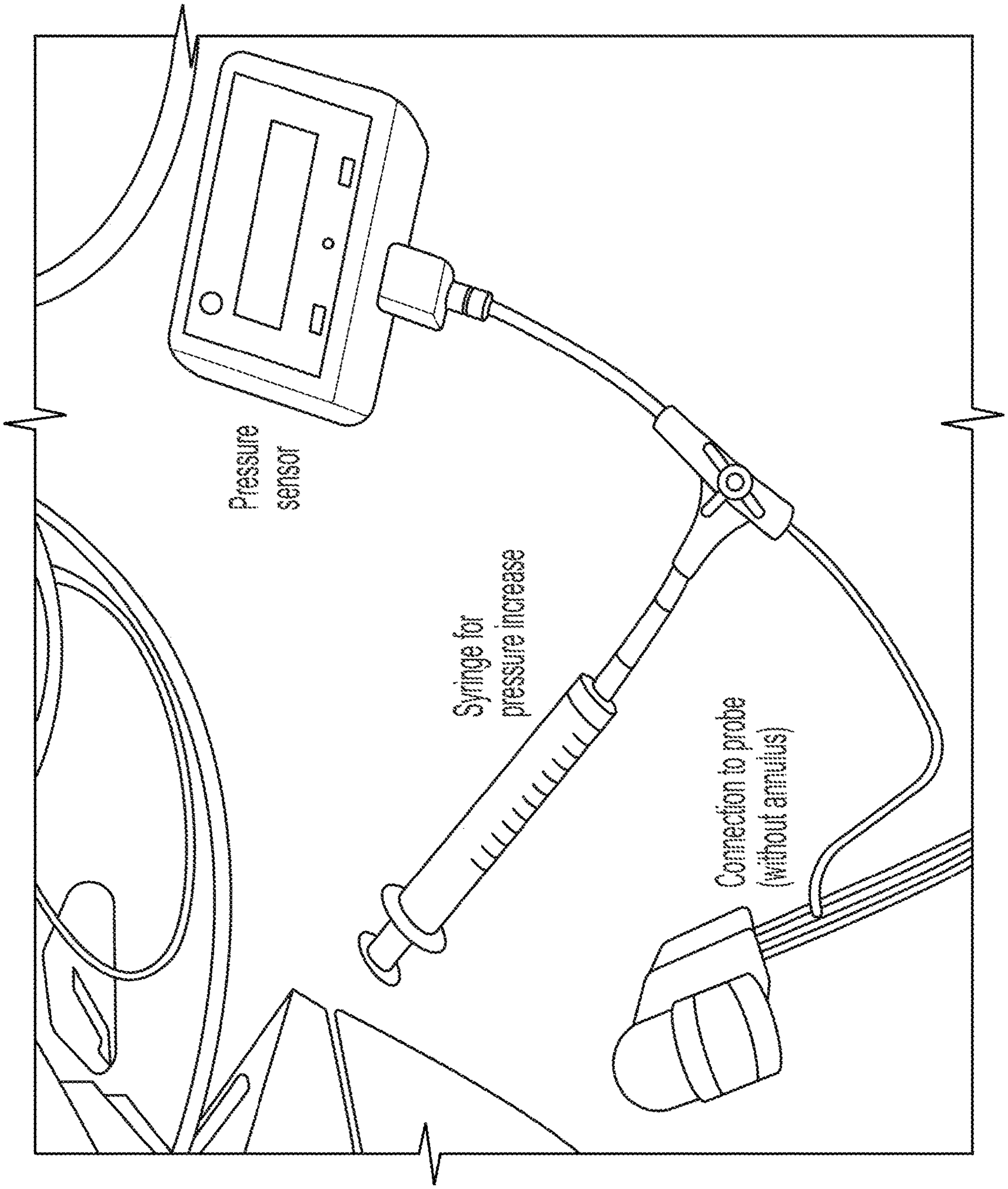
FIGS. 12A-12C show examples of closed air systems.
Figure 12B:
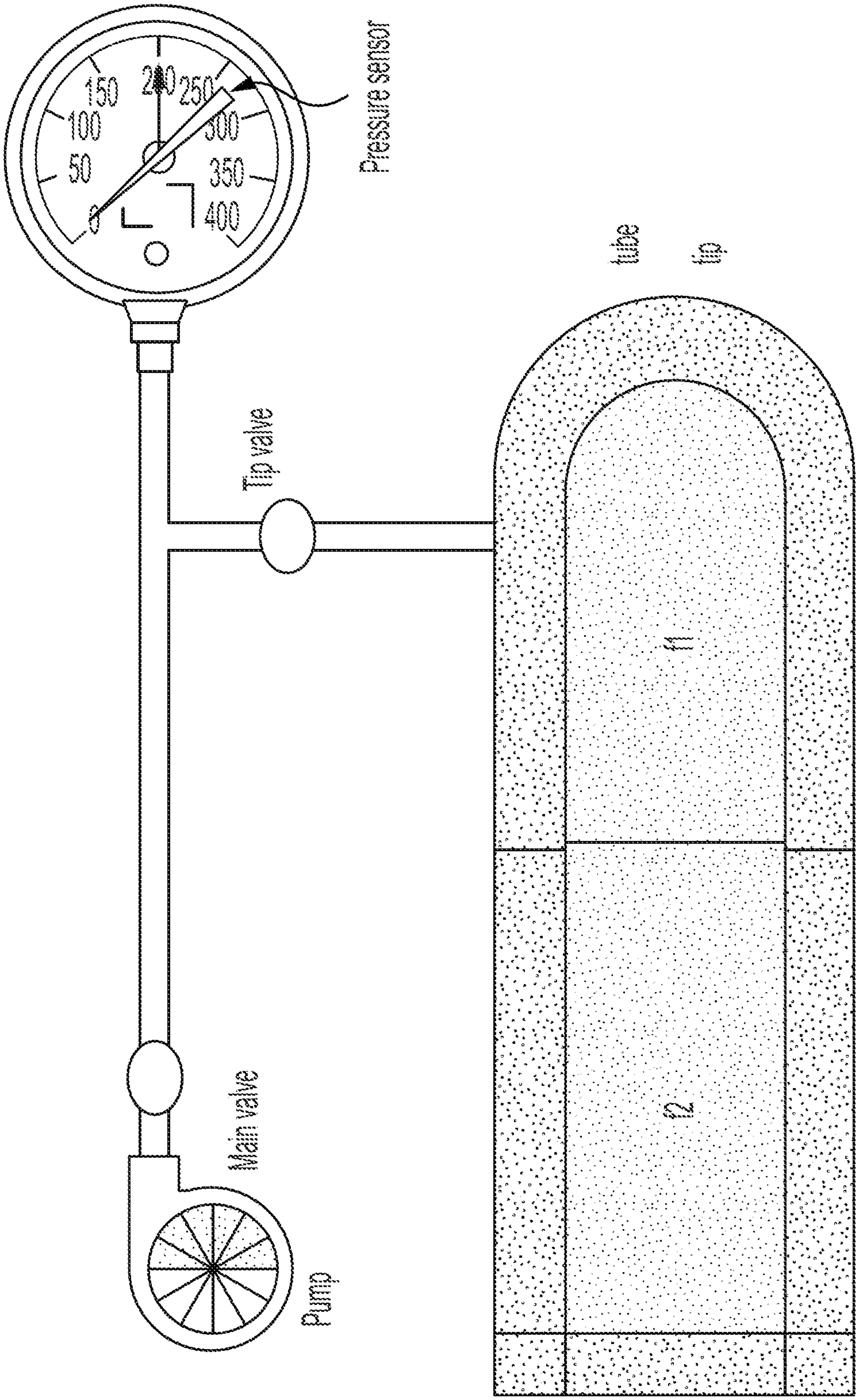

As shown in FIGS. 12A and 12B, in some implementations, EPD 102 may include a closed air system, such as a syringe or a pump. A pressure channel of MD 104 (e.g., the finger probe portion, a pressure transducer thereof) may be connected to the syringe or pump, and the syringe or pump may change its internal air pressure mechanically. The mechanical change can be controlled to have a plurality of steps, one step per each predefined pressure. Each pressure level can be a character, and the characters can be used to create words. For example, a pressure transducer of MD 104 may have more than 12 bits effective range, which may enable a data set that can have more than 50 characters. As shown in Table 2 below, different example pressures (measured in PSI) recorded by MD 104 enables an example data set of different characters.

TABLE 3

| PSI | Character |
|---|---|
| 10 PSI | 1 |
| 20 PSI | 2 |
| 30 PSI | 3 |
| 40 PSI | 4 |
| 50 PSI | 5 |

Figure 12C:
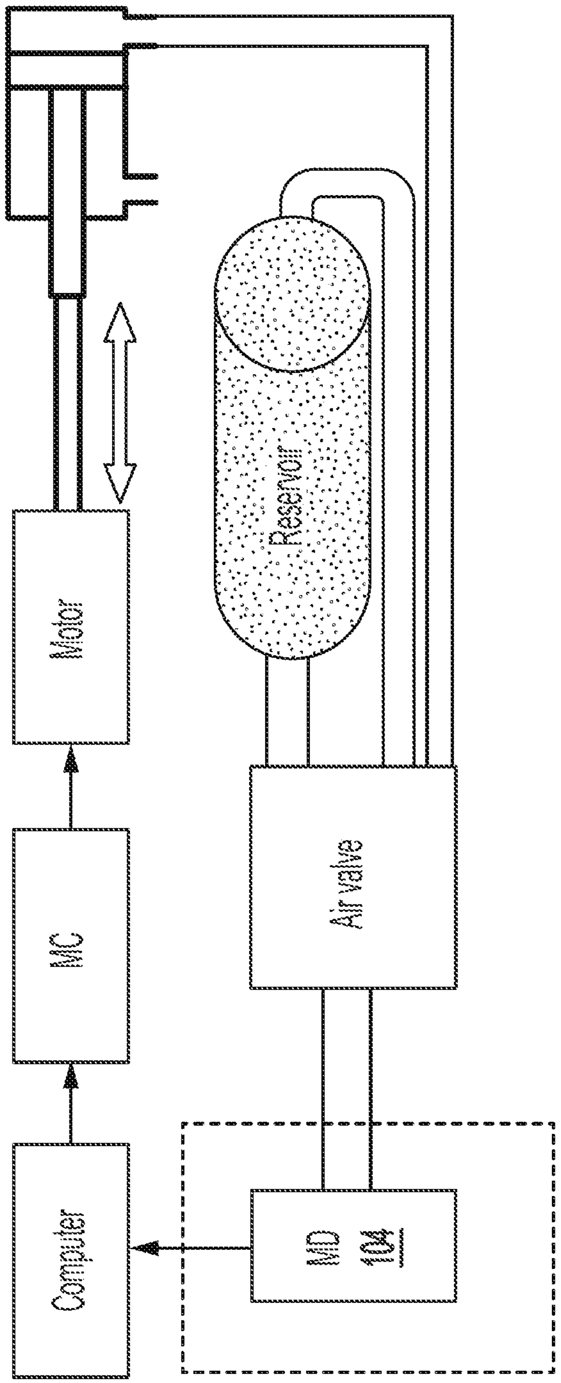

As shown in FIG. 12C, an EPD can be implemented as a computer configured to send a command to a microcontroller (MC). The microcontroller is configured to control the motor to generate the pressure changes based on commands from the computer. For example, the motor may be connected to an air cylinder and create volume changes within the air cylinder to generate the pressure change. The air cylinder may be connected directly or via an intermediate reservoir to MD 104 to apply the pressure changes to the pressure transducer of MD 104.

Figure 13A:
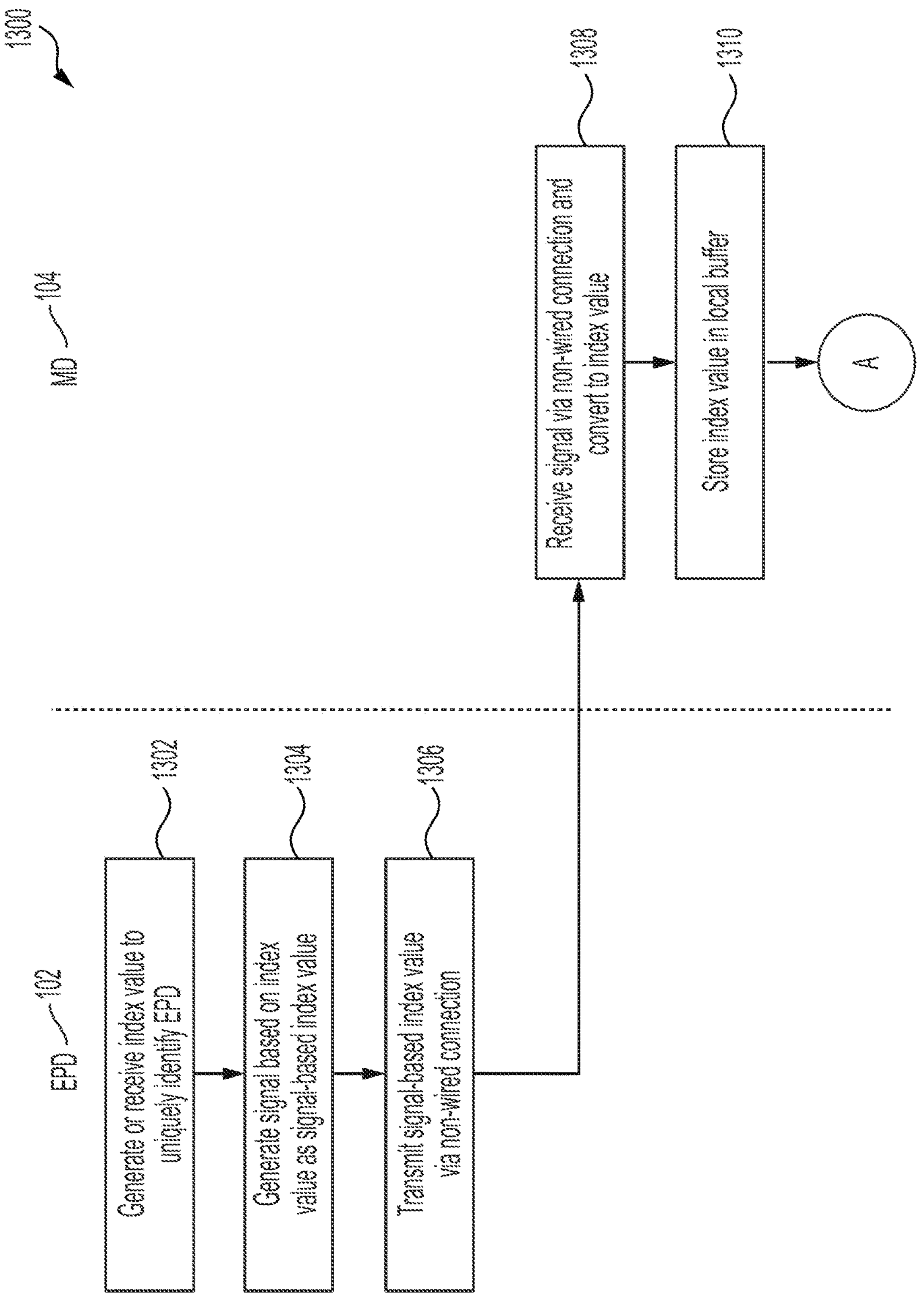
FIGS. 13A-13C are an example flowchart of a process for initializing medical devices, according to some embodiments.
Figure 13B:
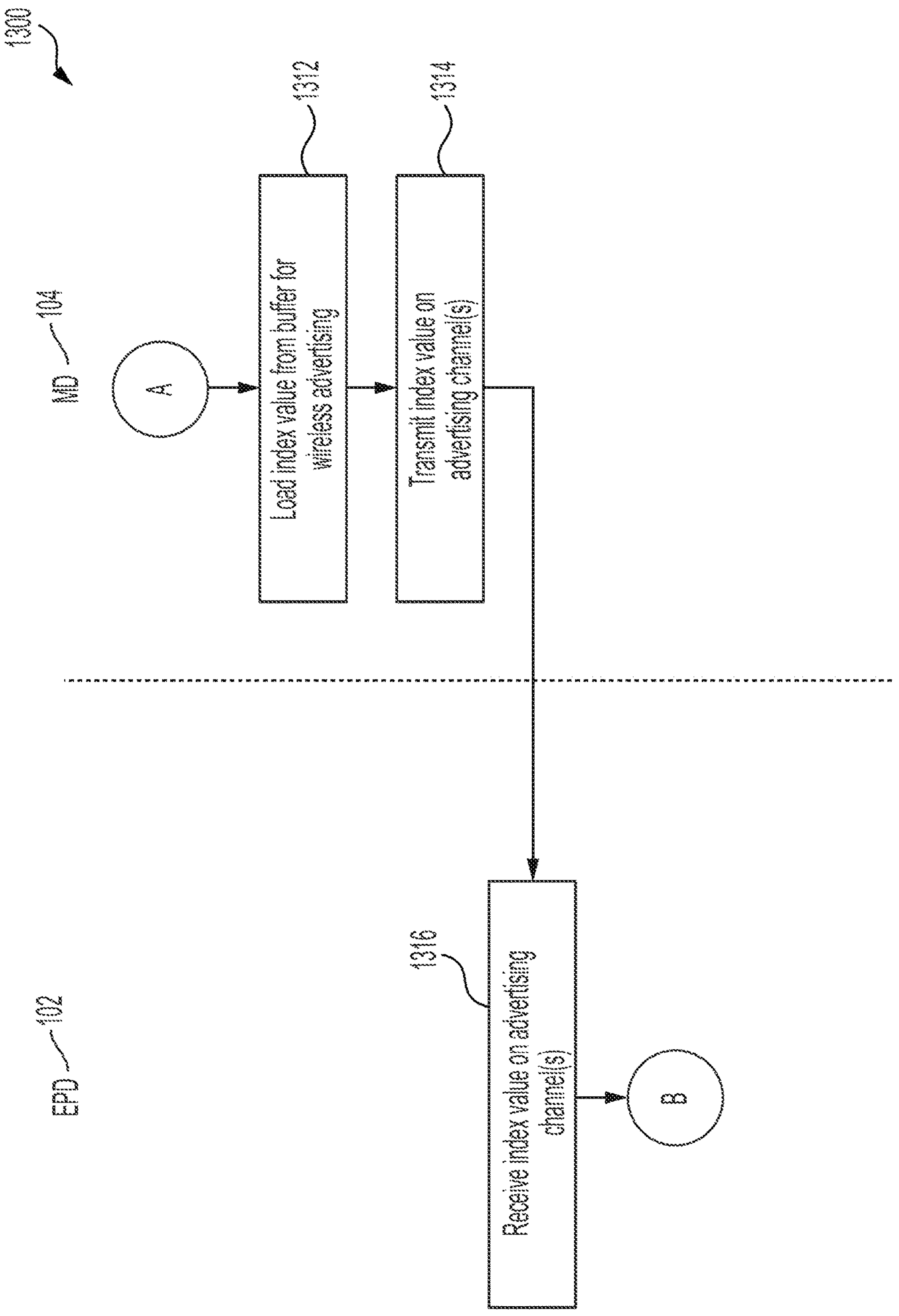
Figure 13C:
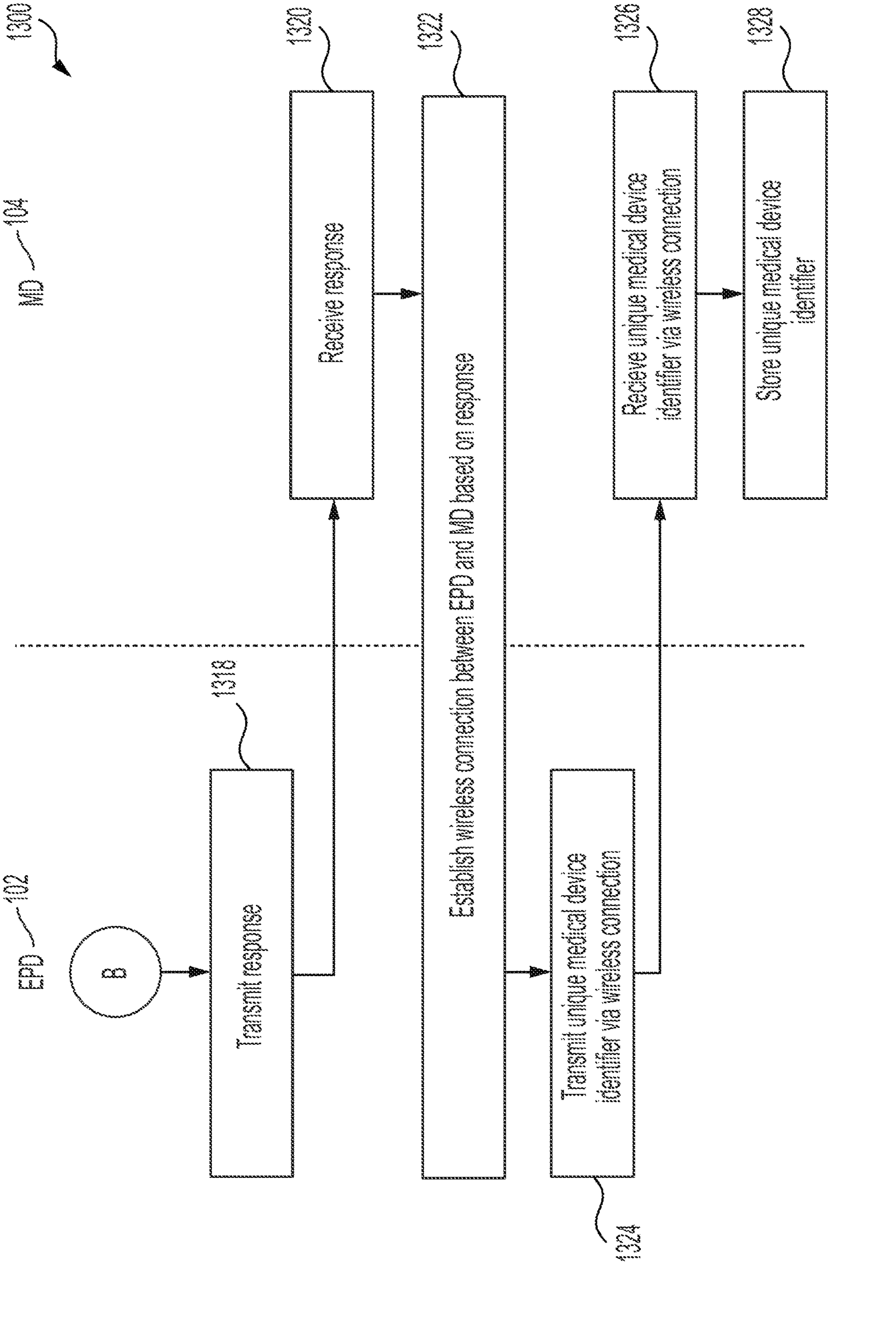

Referring now to FIGS. 13A-13C, FIGS. 13A-13C show an example flowchart of a process 1300 for initializing medical devices, according to some embodiments. In some embodiments, one or more of the steps of process 1300 may be performed (e.g., completely, partially, and/or the like) by EPD 102. In some non-limiting embodiments, one or more of the steps of process 1300 may be performed (e.g., completely, partially, and/or the like) by another system, another device, another group of systems, or another group of devices, separate from or including EPD 102, such as MD 104, configuration system 120, and/or the like. The steps shown in FIGS. 13A-13C are for example purposes only. It will be appreciated that additional, fewer, different, and/or a different order of steps may be used in some embodiments.

As shown in FIG. 13A, at step 1302, process 1300 may include generating or receiving an index value to uniquely identify an EPD. For example, EPD 102 may generate or receive an index value to uniquely identify EPD 102. As an example, index generation circuitry 204 of EPD 102 may generate the index value based on a predetermined input to index generation circuitry 204. In such an example, user interface 210 (e.g., a touch screen display, a keyboard, a keypad, a mouse, a button, a switch, a microphone, a camera, input component 810, and/or the like) may receive a user input and produce the predetermined input to index generation circuitry 204 based on the user input. The user input may include an index value that uniquely identifies EPD 102 and/or a wireless communication network associated with EPD 102 (e.g., a Bluetooth address, a Wi-Fi service set identifier (SSID), etc.).

As shown in FIG. 13A, at step 1304, process 1300 may include generating a signal based on the index value as a signal-based index value. For example, EPD 102 may generate a signal (e.g., an audio signal, an optical signal, a pressure signal, a vibration signal, an orientation signal, etc.) based on the index value as a signal-based index value. As an example, EPD 102 may include a speaker, an optical emitter, a pressure generator, a vibrator, a serial or parallel manipulator robot, and/or the like configured to encode the index value in the signal.

As shown in FIG. 13A, at step 1306, process 1300 may include transmitting the signal-based index value via a non-wired connection. For example, EPD 102 may transmit the signal-based index value via a non-wired connection. As an example, MD 104 may include an uninitialized medical device of a plurality of uninitialized medical devices. In such an example, MD 104 may include one or more sensors (e.g., a microphone, an optical sensor, a pressure transducer, an accelerometer, etc.) configured to receive or pick-up the signal-based index value.

As shown in FIG. 13A, at step 1308, process 1300 includes receiving a signal via the non-wired connection. For example, MD 104 may receive the signal via non-wired connection 108. As an example, the one or more sensors of MD 104 may receive the signal and determine, based on the signal, the index value that identifies EPD 102. For example, as described herein, the MD interprets the received signal and converts such signal into the index value that identifies the EPD 102. In one example, MD 104 may determine the index value as a predetermined sequence, e.g., as a word including a plurality of characters. For example, the predetermined sequence may be based on a binary system, a hexadecimal system, an octal system, or other such system.

As shown in FIG. 13A, at step 1310, process 1300 may include storing the index value in a local buffer. For example, MD 104 may store the index value in a local buffer (e.g., buffer 308, etc.).

As shown in FIG. 13B, at step 1312, process 1300 may include loading the index value from the local buffer for wireless advertising. For example, MD 104 may load the index value from the local buffer (e.g., buffer 308, etc.) for wireless advertising (e.g., for Bluetooth or BLE advertising, etc.). As an example, processor 306 of MD 104 may load the binary sequence of bits from buffer 308 as the index value for wireless advertising.

As shown in FIG. 13B, at step 1314, process 1300 may include transmitting the index value on one or more advertising channels. For example, MD 104 may transmit the index value on one or more advertising channels (e.g., one or more BLE channels, etc.). As an example, MD 104 may transmit the index value on one or more of BLE channels 37, 38, and 39 used for the initial exchange of advertising packets.

For communication, the BLE protocol employs a predetermined set of data channels. For example, the protocol includes 40 physical data channels, which range in number from 0 to 39, and are separated from one another by 2 MHz in the 2.4 GHz frequency range. Frequency hopping is a technique used by BLE to reduce interference and boost dependability. This technique avoids using channels that are experiencing interference by having the transmitter and receiver rapidly switch channels in a pseudo-random order. For implementations herein, a BLE connection can be first established by EPD 102 and MD 104 by exchanging advertising packets, which are used to broadcast details about EPD 102. The devices transition to a different set of channels, known as the data channels, which are used once a connection request has been made.

The Bluetooth LE system operates in the 2.4 GHZ ISM band at 2400-2483.5 MHZ. It uses 40 RF channels (each channel is 2 MHz wide). FIG. 8 shows the mapping between the frequencies and Bluetooth LE channels. Each of these RF channels is allocated a unique channel index (labeled as channel in the figure).

As shown in FIG. 13B, at step 1316, process 1300 may include receiving the index value on the one or more advertising channels. For example, EPD 102 may receive the index value on the one or more advertising channels (e.g., the one or more BLE channels, etc.). As an example, EPD 102 may receive the index value on one or more of BLE channels 37, 38, and 39 used for the initial exchange of advertising packets.

In examples, certain advertising channels (e.g., channels 37, 38, and 39) of the BLE protocol can be used for the initial exchange of advertising packets. The data channels (0 to 36) can be used for actual data transmission once the connection has been established. In one implementation, to use the index string from the local buffer to establish a BLE connection to another device, MD 104 can send a connection request packet to EPD 102 (e.g., the target device). In some example implementations, the connection request packet can include the index string as part of the data payload. EPD 102 can extract the index string from the payload of the connection request packet and confirm that the index string is genuine (e.g., using a predefined authentication process). In another implementation, the MD 104 can send advertising packets, and the EPD 102 can send a connection request packet to MD 104 on receiving the advertising packets.

As shown in FIG. 13C, at step 1318, process 1300 may include transmitting a response. For example, EPD 102 may transmit a response. As an example, EPD 102 can send a response packet indicating that EPD 102 is prepared to establish a BLE connection if the index value is correct and corresponds to a MD 104 that is authorized to connect to the EPD 102. For example, EPD 102 as the target device knows its own index value identifying EPD 102 and as such is able to authenticate the request. Also, one of the data channels can be used to send the response packet.

As shown in FIG. 13C, at step 1320, process 1300 may include receiving the response. For example, MD 104 may receive the response. As an example, MD 104 may receive the response packet indicating that EPD 102 is prepared to establish a BLE connection.

As shown in FIG. 13C, at step 1322, process 1300 may include establishing a wireless connection between an EPD and a MD based on the response. As an example, assuming the device processor gets a legitimate response packet, MD 104 can connect to EPD 102 via BLE on one of the data channels. The two devices can communicate and share data once the BLE connection has been made. Specific data channel frequency bands that can be used may depend on the implementation of the BLE protocol.

In an alternate scheme, when establishing a BLE connection, MD 104 may send advertising packets, which are used to broadcast information about the MD. To include the index value in the connection request, the MD processor can append the index string to a value that is transmitted in the advertising packets. EPD 102 can then extract the index value from the received advertising packets and use it to verify that the index value is legitimate. For example, the MD processor may include the index value as part of the device name in the advertising packets. The advertising packets can be transmitted on primary advertising channels (37, 38, and 39). When EPD 102 receives the advertising packets, EPD 102 can extract the MD name and parse out the index string. EPD 102 can verify that the index string is valid and corresponds to a device that is allowed to connect. Once EPD 102 has verified the index value, EPD 102 can send a response packet indicating that EPD 102 is ready to establish a BLE connection. The response packet can also include the index string as part of the data payload, which the MD processor can use to verify that the request is legitimate. Assuming the MD processor receives a valid request packet, MD 104 can establish a BLE connection with the target device on one of the data channels, which are used for actual data transmission once the connection has been established. The specific implementation of this scenario may vary. For example, the MD processor can be configured to ensure that the index value is correctly formatted and appended to the correct value in the advertising packets. EPD 102 can implement additional security measures to prevent unauthorized access. Additionally, the specific data channel frequency bands used may depend on the frequency-hopping scheme used by the devices.

As shown in FIG. 13C, at step 1324, process 1300 may include transmitting a unique medical device identifier via the wireless connection. For example, EPD 102 may transmit, via the wireless connection between EPD 102 and MD 104 (e.g., via a Bluetooth connection, etc.), a unique medical device identifier to MD 104 that causes MD 104 to be uniquely addressable. As an example, EPD 102 may transmit the unique medical device identifier to MD 104 via BLE on one of the data channels.

In some embodiments, EPD 102 may program, via the wireless connection between EPD 102 and MD 104, one or more monitoring and/or treatment parameters and/or thresholds of MD 104 for use in operation of MD 104, as described in more detail herein.

As shown in FIG. 13C, at step 1326, process 1300 may include receiving the unique medical device identifier via the wireless connection. For example, MD 104 may receive, via the wireless connection (e.g., via wireless communication network 106, etc.) between EPD 102 and MD 104, a unique medical device identifier that causes MD 104 to be uniquely identifiable. As an example, MD 104 may receive the unique medical device identifier from EPD 102 via BLE on one of the data channels.

In some embodiments, MD 104 may receive, via the wireless connection between EPD 102 and MD 104, one or more monitoring and/or treatment parameters and/or thresholds of the uninitialized medical device for use in operation of the uninitialized medical device, as described in more detail herein.

As shown in FIG. 13C, at step 1328, process 1300 may include storing a unique medical device identifier. For example, MD 104 may store, in a non-volatile memory (e.g., memory 307, etc.), the unique medical device identifier to initialize MD 104 by causing MD 104 to be uniquely addressable, as described in more detail herein.

In some embodiments, MD 104 may execute one or more hardware and/or software built-in tests and transmit, via the wireless connection between EPD 102 and MD 104, a result of the one or more hardware and/or software built-in tests, as described in more detail herein.

Figure 14:
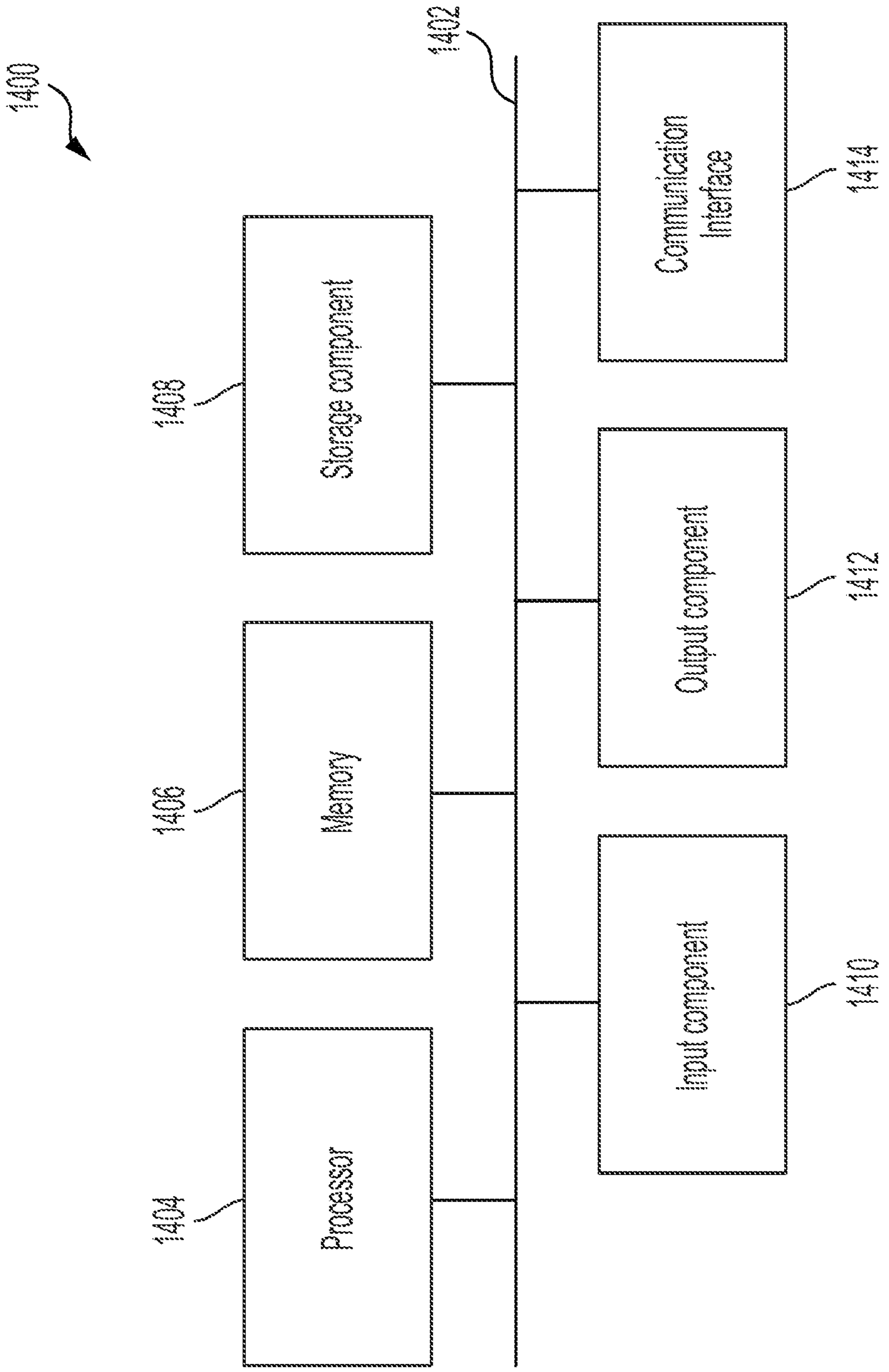
FIG. 14 shows an example block diagram of components of one or more computing devices on which the processes described herein can be implemented, according to some embodiments.

Referring now to FIG. 14, FIG. 14 is a diagram of example components of a device 1400, according to some embodiments. Device 1400 may correspond to one or more devices of EPD 102, MD 104, and/or configuration system 120. In some non-limiting embodiments, EPD 102, MD 104, and/or configuration system 120 may include at least one device 1400 and/or at least one component of device 1400. As shown in FIG. 14, device 1400 may include bus 1402, processor 1404, memory 1406, storage component 1408, input component 1410, output component 1412, and communication interface 1414.

Bus 1402 may include a component that permits communication among the components of device 1400. In some non-limiting embodiments, processor 1404 may be implemented in hardware, firmware, and/or a combination of hardware and software. For example, processor 1404 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), an application-specific standard product (ASSP), a system-on-a-chip (SOC), a tensor processing units (TPU), and/or the like), and/or the like, which can be programmed to perform a function. Memory 1406 may include random access memory (RAM), read only memory (ROM), and/or another type of dynamic or static storage device (e.g., flash memory, magnetic memory, optical memory, and/or the like) that stores information and/or instructions for use by processor 1404.

Storage component 1408 may store information and/or software related to the operation and use of device 1400. For example, storage component 1408 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 1410 may include a component that permits device 1400 to receive information, such as via user input (e.g., a touch screen display, a keyboard, a keypad, a mouse, a button, a switch, a microphone, a camera, and/or the like). Additionally or alternatively, input component 1410 may include a sensor for sensing information (e.g., a heart rate sensor, an oxygen saturation sensor, an actigraphy sensor (e.g., an accelerometer), a snoring sensor (e.g., a microphone, a vibration sensor, and/or the like), a chest motion sensor, a body position sensor, an arm position sensor, a sleep stage sensor, a global positioning system (GPS) component, an accelerometer, a gyroscope, an actuator, an electrode, any combination thereof, and/or the like). Output component 1412 may include a component that provides output information from device 1400 (e.g., a display, a speaker, one or more light-emitting diodes (LEDs), and/or the like).

Communication interface 1414 may include a transceiver-like component (e.g., a transceiver, a receiver and transmitter that are separate, and/or the like) that enables device 1400 to communicate with other devices, such as via a wired connection, a wireless connection, or a combination of wired and wireless connections. Communication interface 1414 may permit device 1400 to receive information from another device and/or provide information to another device. For example, communication interface 1414 may include a network interface controller (NIC), an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

Device 1400 may perform one or more processes described herein. Device 1400 may perform these processes based on processor 1404 executing software instructions stored by a computer-readable medium, such as memory 1406 and/or storage component 1408. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 1406 and/or storage component 1408 from another computer-readable medium or from another device via communication interface 1414. When executed, software instructions stored in memory 1406 and/or storage component 1408 may cause processor 1404 to perform one or more processes described herein. Additionally or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 14 are provided as an example. In some non-limiting embodiments, device 1400 may include additional components, fewer components, different components, or differently arranged components than those shown in FIG. 14. Additionally or alternatively, a set of components (e.g., one or more components) of device 1400 may perform one or more functions described as being performed by another set of components of device 1400.

Figure 15:
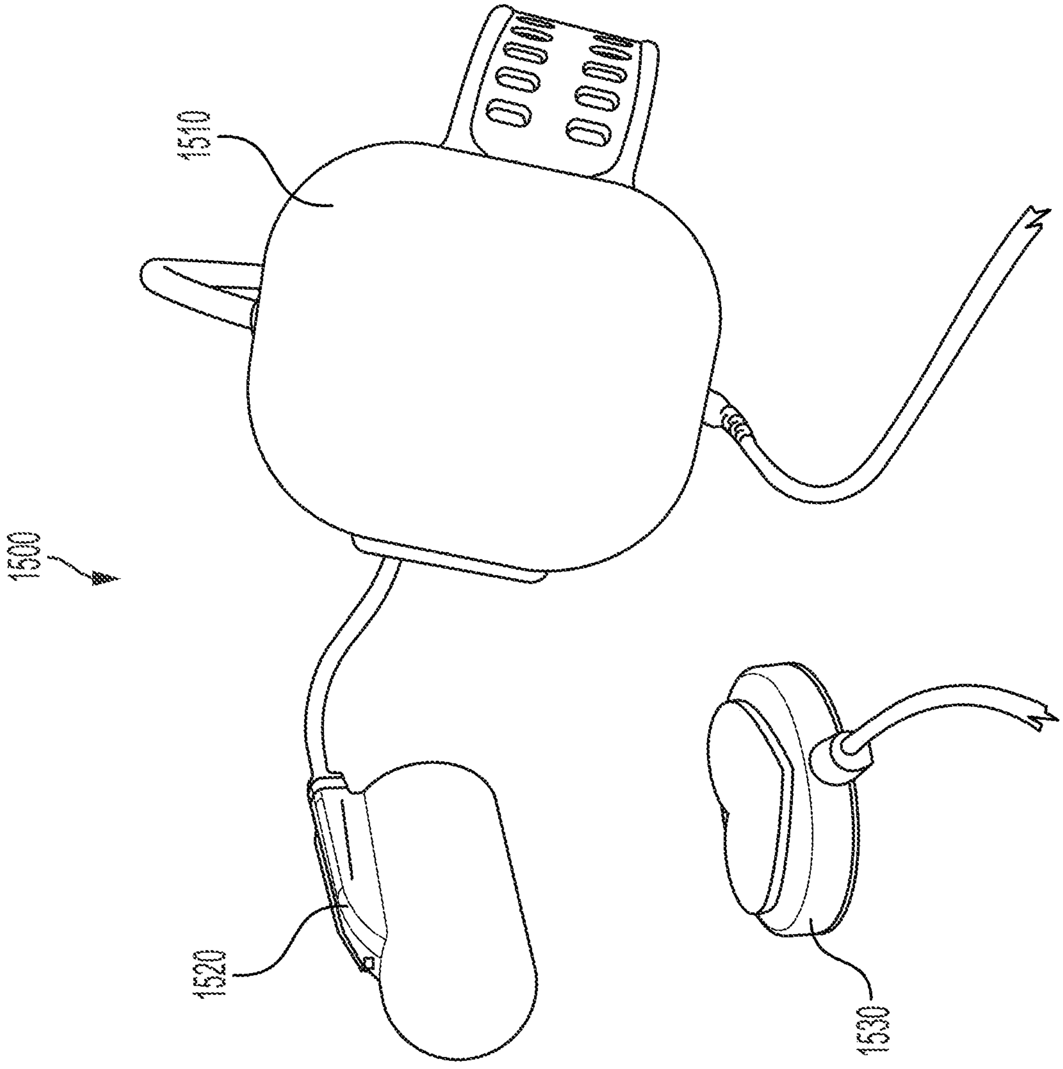
FIG. 15 shows a wearable device for monitoring sleep disordered breathing parameters.

Referring to FIG. 15, a wearable device 1500 for monitoring sleep disordered breathing parameters includes a wrist device 1510, a finger probe 1520, and/or a chest sensor 1530. In some embodiments, the wearable device 1500 may include only the wrist device 1510 and the finger probe 1520. In some embodiments, the wearable device 1500 may include only the finger probe 1520. In some embodiments, the wearable device 1500 may include each of the wrist device 1510, the finger probe 1520, and the chest sensor 1530.

Wearable devices as described herein are capable of being continuously used or continuously worn by, or attached or connected to, the patient without substantial interruption (e.g., overnight, for around 8 hours, for around 10 hours, for around 12 hours, for around 24 hours, around 2 days, around 5 days, around 7 days, or beyond, such as multiple weeks). In some implementations, such devices may be worn for a period of use (e.g., for a single night of use, etc.) In some implementations, such devices may be worn for multiple periods of use (e.g., for multiple nights of use, etc.). In some implementations, such devices may be briefly removed for a period of time before use, wear, attachment, or connection to the patient is resumed. Such substantially or nearly continuous use, monitoring, or wear as described herein may nonetheless be considered continuous use, monitoring, or wear. As an illustration, the device may be removed for charging, to carry out technical service, to update the device software or firmware, for the patient to make a fit or comfort adjustment, and/or for other reasons or activities.

The wrist device 1510 is configured to be strapped to a wrist of a patient, preferably the wrist of the non-dominant arm of the patient. The wrist device 1510 may include a battery compartment, and preferably may be powered by a standard size battery, such as a AAA battery. Prior to strapping the wrist device 1510 to his or her wrist, the patient may insert the battery into the battery compartment.

Figure 18:
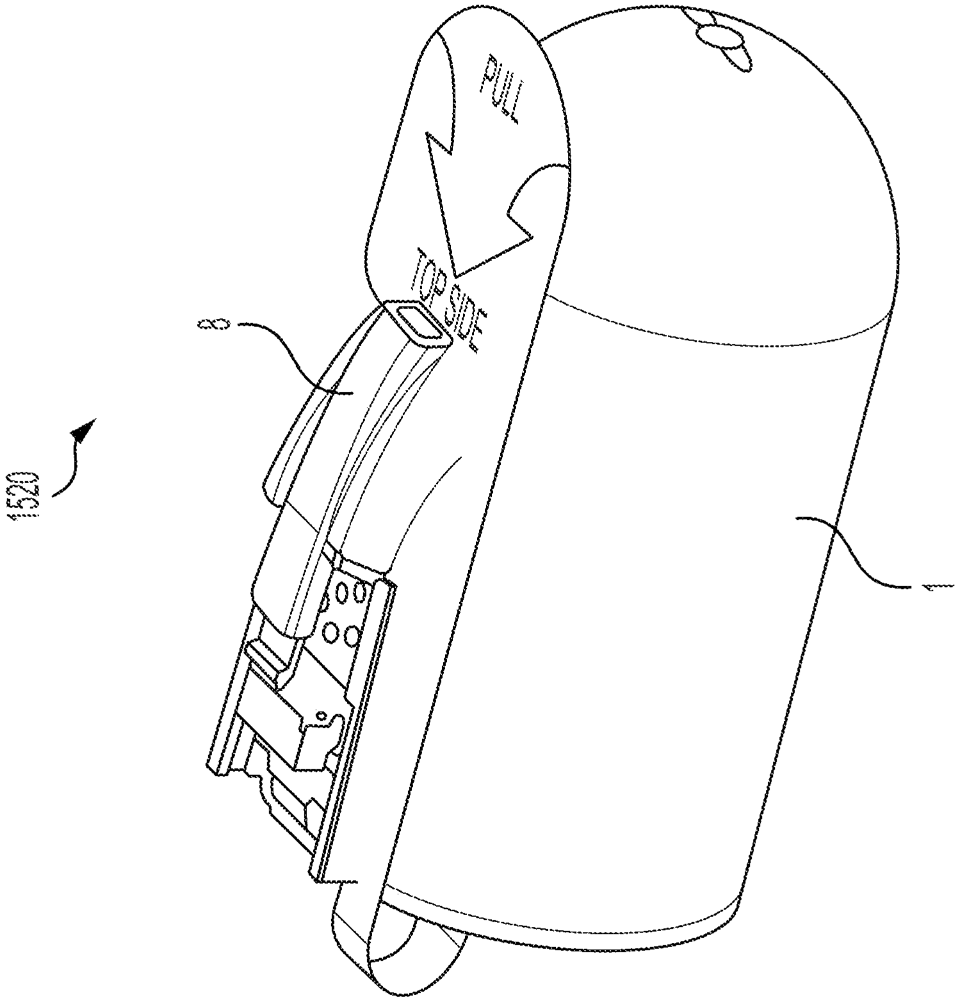
FIG. 18 shows a finger probe of a wearable device for monitoring sleep disordered breathing parameters.

Referring to FIGS. 15 and 18 the finger probe 1520 may include a PPG probe and/or an electro-opto-pneumatic finger-mounted probe. For example, the finger probe 1520 may include a sensor for measuring a PPG signal and/or a peripheral arterial signal, e.g., through the application of a pressure field on the portion of the patient's body to which the sensor is attached. In operation, the finger probe 1520 is configured to continuously optically measure the relative state of vasomotor activity in a distal part of a finger on which the finger probe 1520 is secured to obtain a plethysmogram that can be used to detect blood volume changes in the microvascular bed of tissue. In some implementations, the finger probe 1520 is configured to cover the distal part of a finger of the patient with a uniform predetermined pressure field extending to a tip of the finger for measuring. Application of the pressure field can prevent venous blood pooling, engorgement and stasis, which inhibits retrograde venous shock wave propagation, and allows partial unloading of arterial wall tension that significantly improves the dynamic range of the measured signal. The optic component of the probe can measure optical density related changes of the arterial blood volume in the digital arteries, associated with each heartbeat. Peripheral arterial constrictions, when present, are shown by attenuation in a peripheral arterial signal, a marker of sympathetic activation.

Although described herein primarily as a finger probe, the probe 1520 may include a PPG probe and/or an electro-opto-pneumatic probe configured for mounting or attachment to another body part or digit of the patient. For example, the probe 1520 may be configured for mounting to another portion or digit of the patient at which the relative state of vasomotor activity of the patient may be optically measured to obtain a plethysmogram that can be used to detect blood volume changes in the microvascular bed of tissue. As an example, the finger probe 1520 may be configured to continuously optically measure the relative state of vasomotor activity in a toc, a neck, a wrist, and/or the like on which the probe 1520 is secured to obtain a plethysmogram that can be used to detect blood volume changes in the microvascular bed of tissue. In such an example, the probe 1520 may be configured to cover the other portion or digit of the patient with a uniform predetermined pressure field extending to a tip of the finger.

The finger probe 1520 incorporates at least one optical sensor. In implementations, the finger probe 1520 incorporates at least a pair of LED light sources and detectors. For example, the pair of LED light sources and detectors is configured to measure red and infrared signals at different wavelengths, which can be used to calculate the patient's oxygen saturation. In examples, the finger probe 1520 can measure changes in absorbance of the finger at both red and infrared light at peak wavelengths of approximately 660 nm and 910 nm, respectively. In some implementations, a maximum optical output power may be about 65 mW, e.g., in a range of about 60 mW to 70 mW. These measurements may be used to calculate pulse oximetry, i.e., oxygen saturation ($SpO_2$), using an offline program according to known principles.

Figure 17:
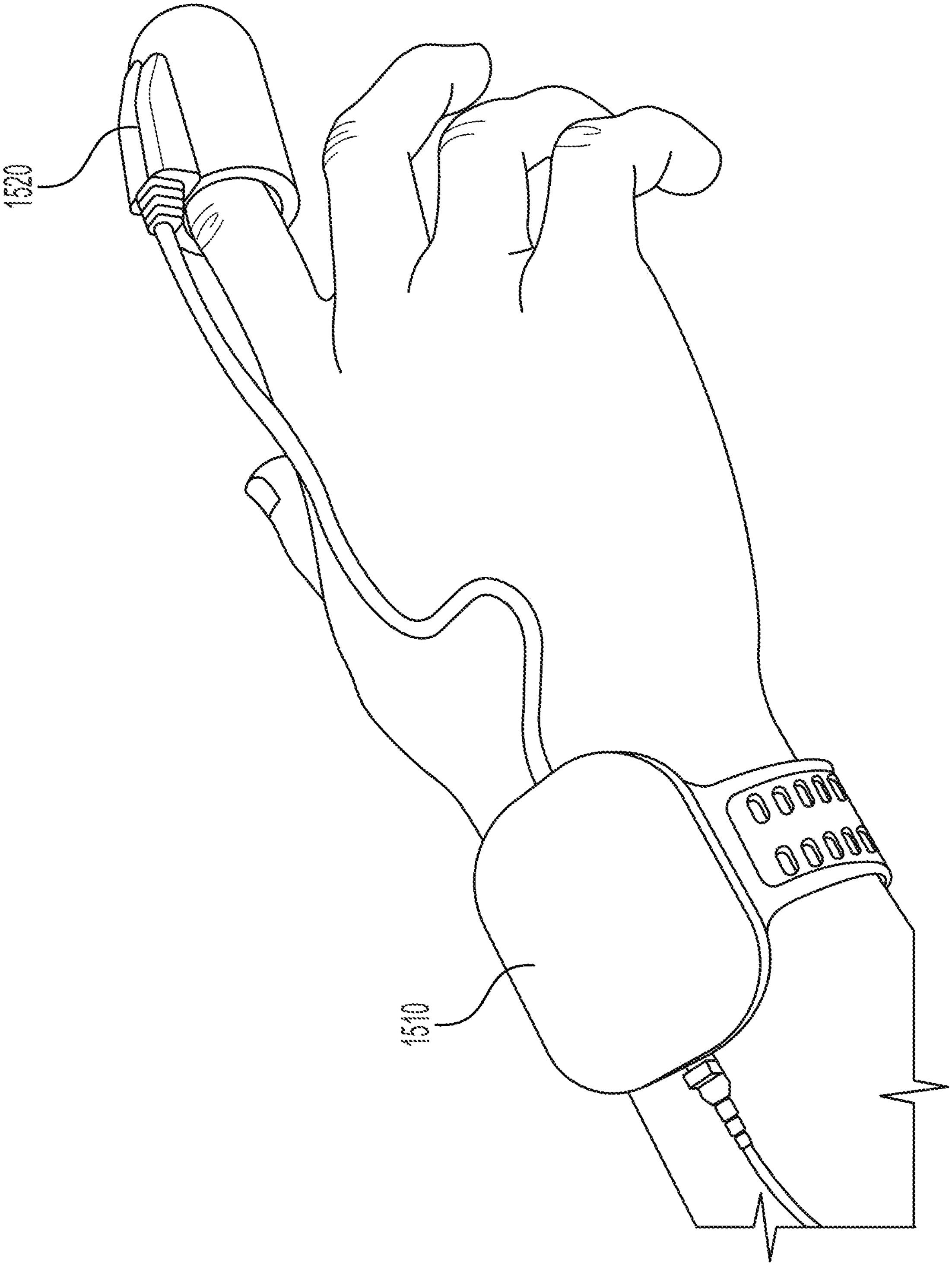
FIG. 17 shows a wrist device and a finger probe of a wearable device for monitoring sleep disordered breathing parameters.

Referring to FIGS. 17-18, the finger probe 1520 incorporates a pressure device that is configured to apply a substantially uniform sub-diastolic pressure field to the patient's finger when secured in the finger probe 1520. The pressure device includes inner and outer membranes contained within a housing of the finger probe 1520. By application of the pressure device, it is possible to maintain a substantially uniform pressure field inside the finger probe 1520 that is independent of a volume of the patient's finger.

Referring again to FIG. 15, the chest sensor 1530 is optionally provided to detect snore and/or movement of the patient's chest. In particular, the chest sensor 1530 may internally incorporate two sensors: a snore sensor and a chest movement sensor. For example, the snore sensor may be an acoustic decibel detector that includes a microphone to detect snoring or other sounds in an audio range and convert them to an output signal. The chest movement sensor may be a 3-axis accelerometer that provides a signal that reflects movement of the patient's chest. The signal can be analyzed to determine the patient's sleeping posture (supine, prone, right, left, and sit), and an indication of the patient's chest movement resulting from breathing.

Figure 16:
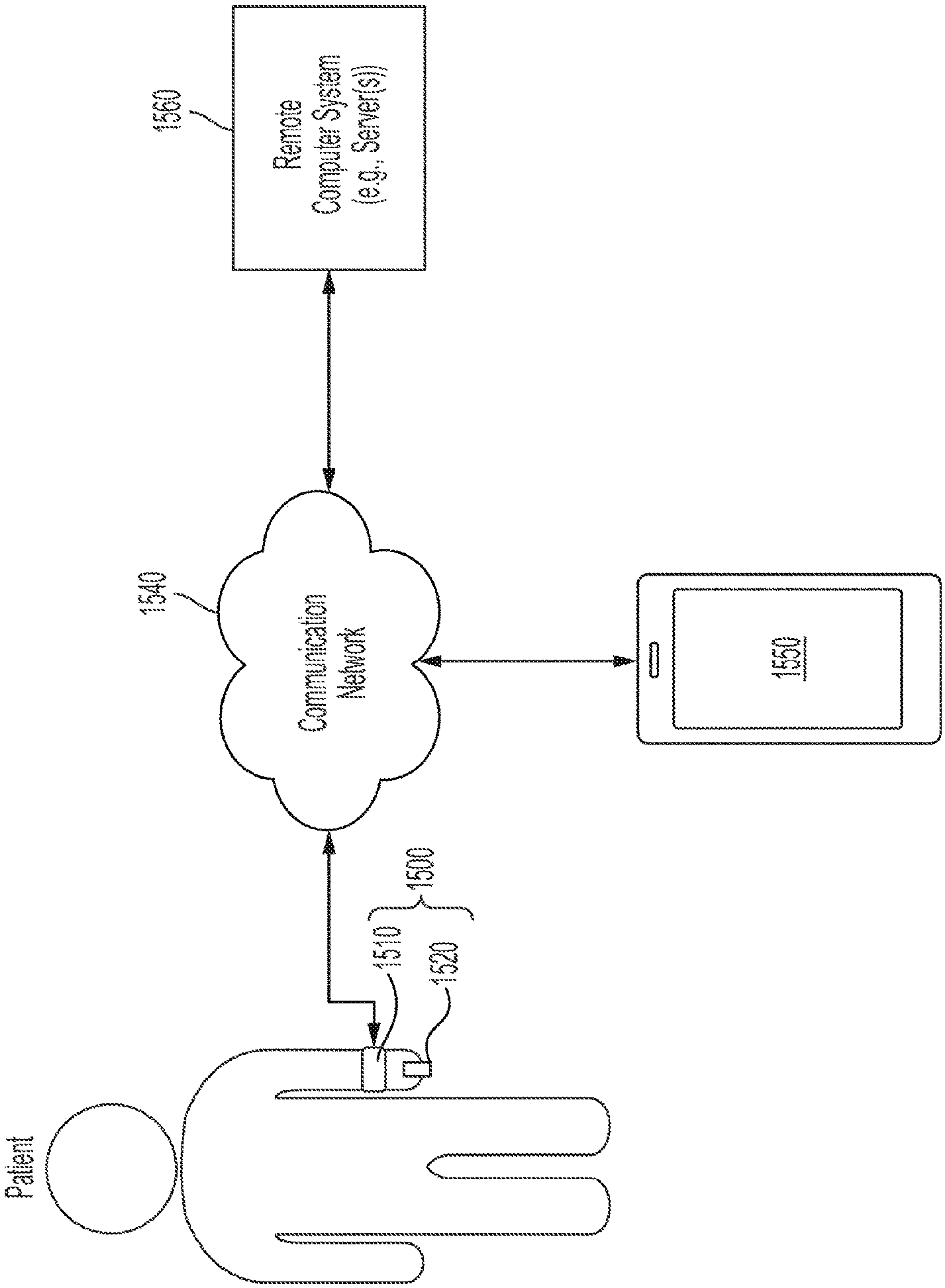
FIG. 16 shows a system for conducting a remote sleep study, e.g., a sleep study that is not conducted in a sleep lab. For example, such remote sleep study includes a home sleep study where the patient sleeps in their own bed at home.

Referring to FIG. 16, a system for conducting a home and/or remote sleep study includes the wearable device 1500 in which the wrist device 1510 is strapped to the wrist of the patient and the finger probe 1520 is secured to the patient's finger. The wrist device 1510 is configured to receive PPG signals, a peripheral arterial signal and/or oxygen saturation data from the finger probe 1520 and actigraphy (movement) data from the chest sensor 1530 (not shown in FIG. 16) and transmit the relevant data using an application running on a mobile device 1550 of the patient via a communication network 1540 to a remote computer system (e.g., one or more web servers) 1560 for further processing. For example, the wrist device 1520 may include wireless communications circuitry including at least one of the following: cellular communications circuitry, Bluetooth communications circuitry, Advanced Message Queuing Protocol (AMQP) circuitry, Constrained Application Protocol (CoAP) circuitry, Wi-Fi circuitry, ZigBee circuitry, Z-Wave circuitry, wireless personal area network (WPAN) circuitry, Infrared Data Association (IrDA) circuitry, any combination thereof, and/or the like. For example, the wireless communications circuitry may be configured to establish at least one of the following types of wireless connections with the remote computing system 1560 and/or mobile device 1550: a cellular connection, a Bluetooth connection, Advanced Message Queuing Protocol (AMQP) connection, Constrained Application Protocol (CoAP) connection, a Wi-Fi connection, a ZigBee connection, a Z-Wave connection, a wireless personal area network (WPAN) connection, an Infrared Data Association (IrDA) connection, any combination thereof, and/or the like. In such an example, communication network 1540 may include one or more wired and/or wireless networks. For example, communication network 1540 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

Processor 306 may be configured to control acquisition of the one or more physiological signals from the one or more physiological sensors and/or control the transmission of data by wireless communications circuitry 304 based on the one or more physiological signals.

The system depicted in FIG. 16 is useful for conducting a home and/or remote sleep study, such as an overnight sleep study. Data such as physiological data obtained from the sleep study is stored on the remote computer system 1560 and obtained, preferably after conclusion of the sleep study, for evaluation. The data may include respiratory and other events that occurred during sleep as well as periods of REM, deep sleep, light sleep and wakefulness. The pulse rate signal may be derived from the peripheral arterial signal and used in the automatic analysis. For example, the system is configured to generate various parameters, including but not limited to: a respiratory disturbance index, an apnea-hypopnea index, a central apnea-hypopnea index, a percentage of total sleep time with Cheyne-Stokes respiration pattern and sleep staging identification. A report may be generated, and the relevant data of the sleep study may be viewed on a screen and the automatically detected events can be revised manually by a physician as needed.

Figure 19A:
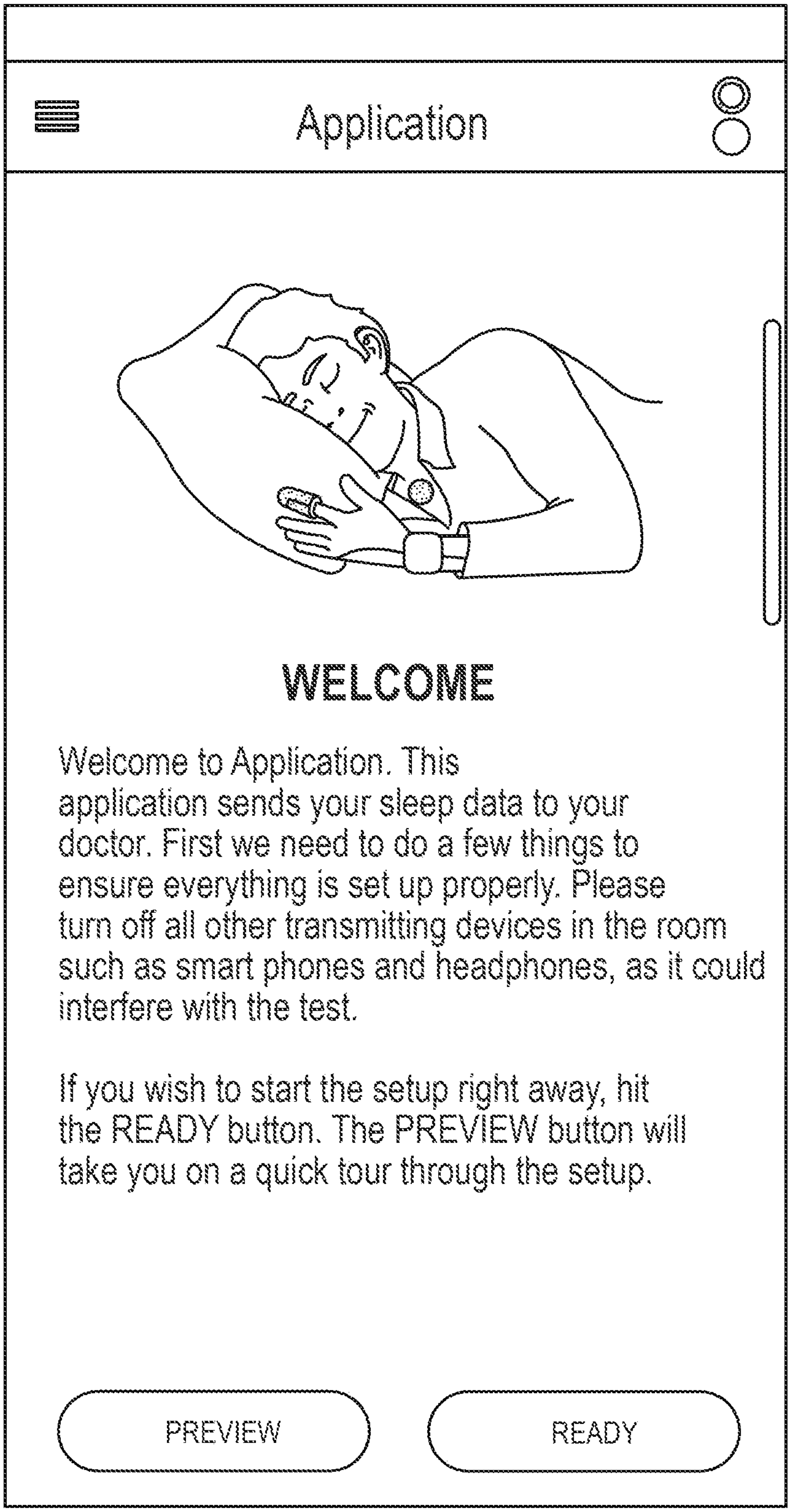
FIGS. 19A-19F show screen shots of an application running on a mobile device.
Figure 19B:
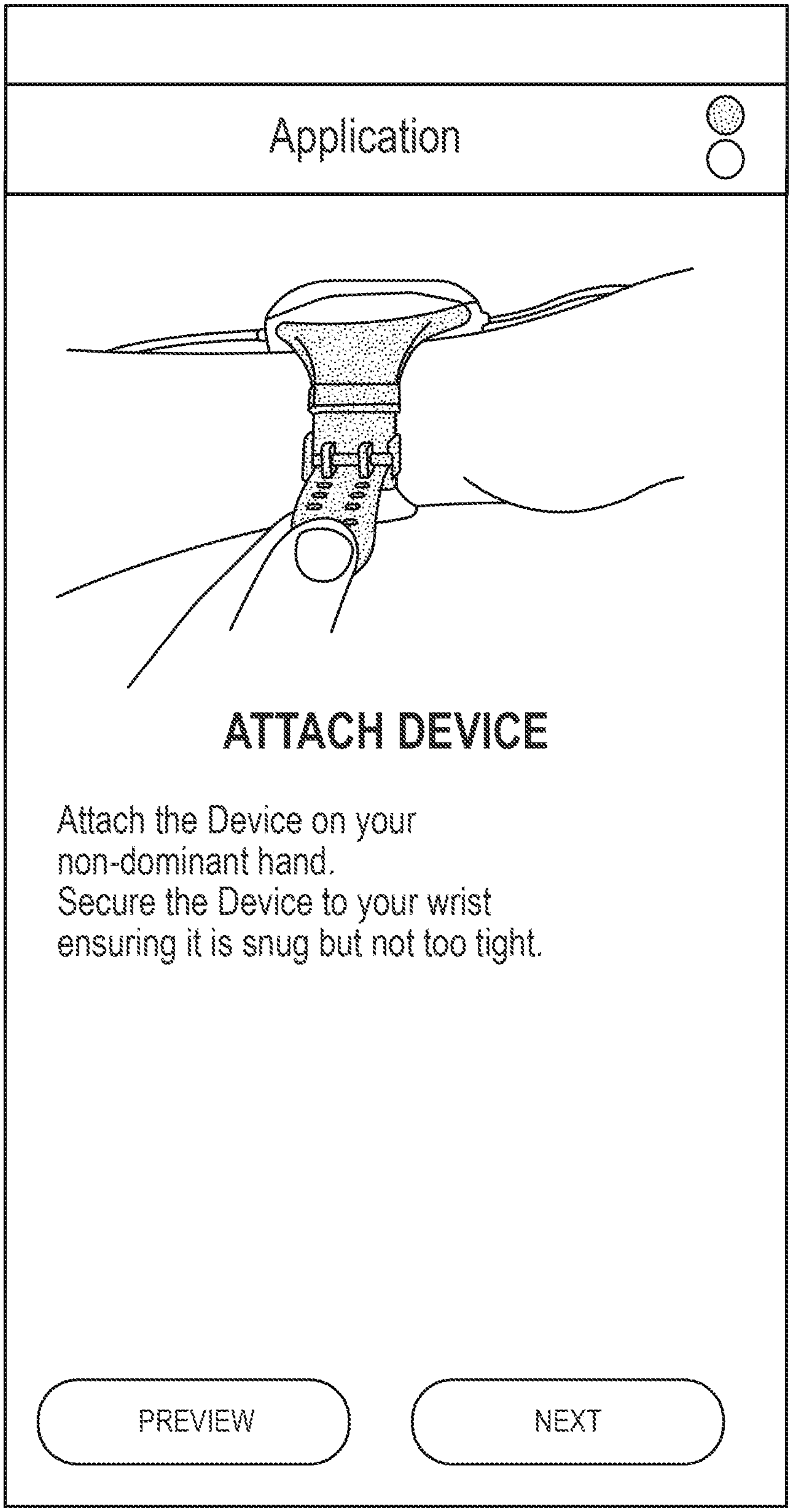
Figure 19C:
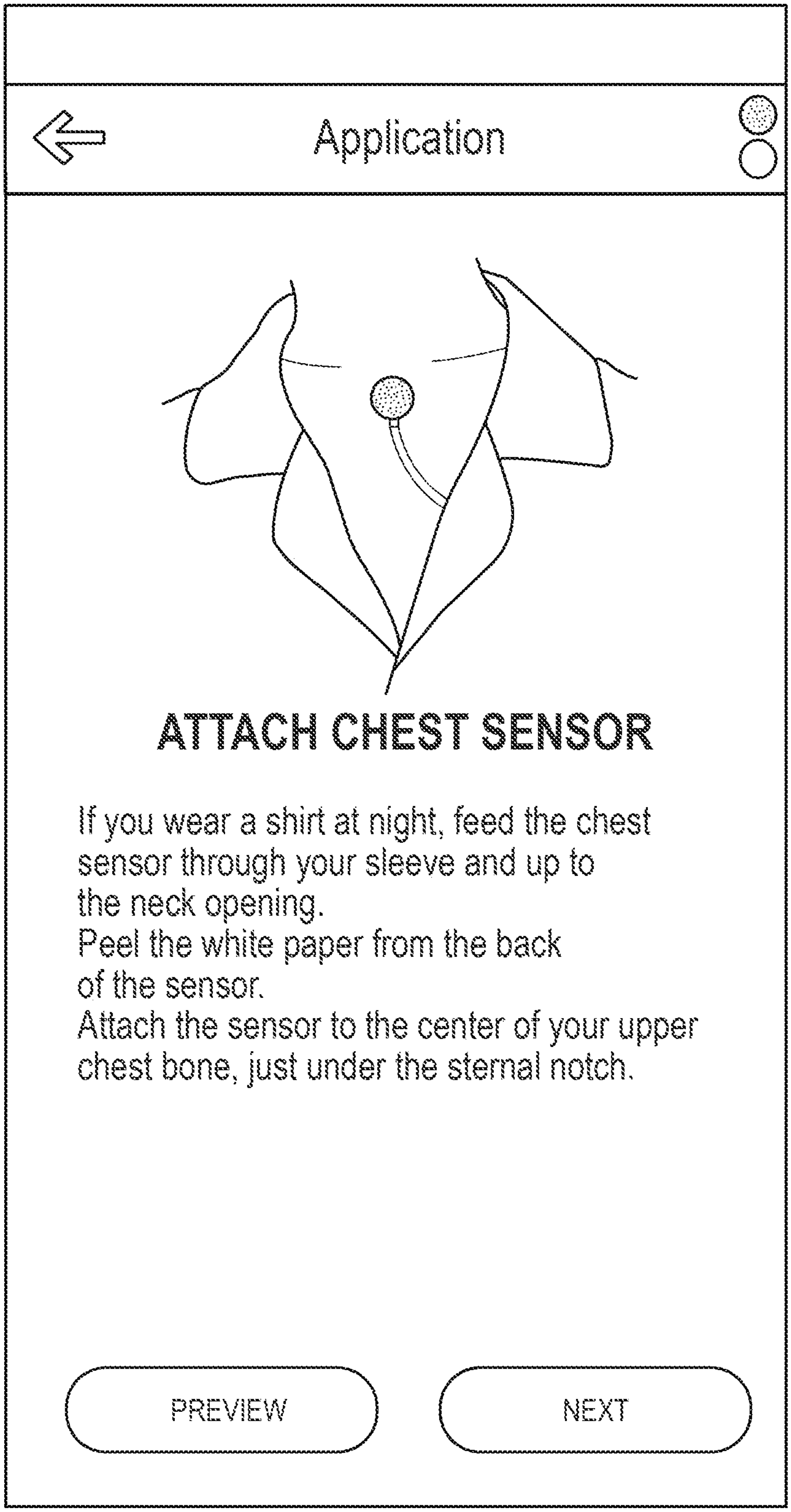
Figure 19D:
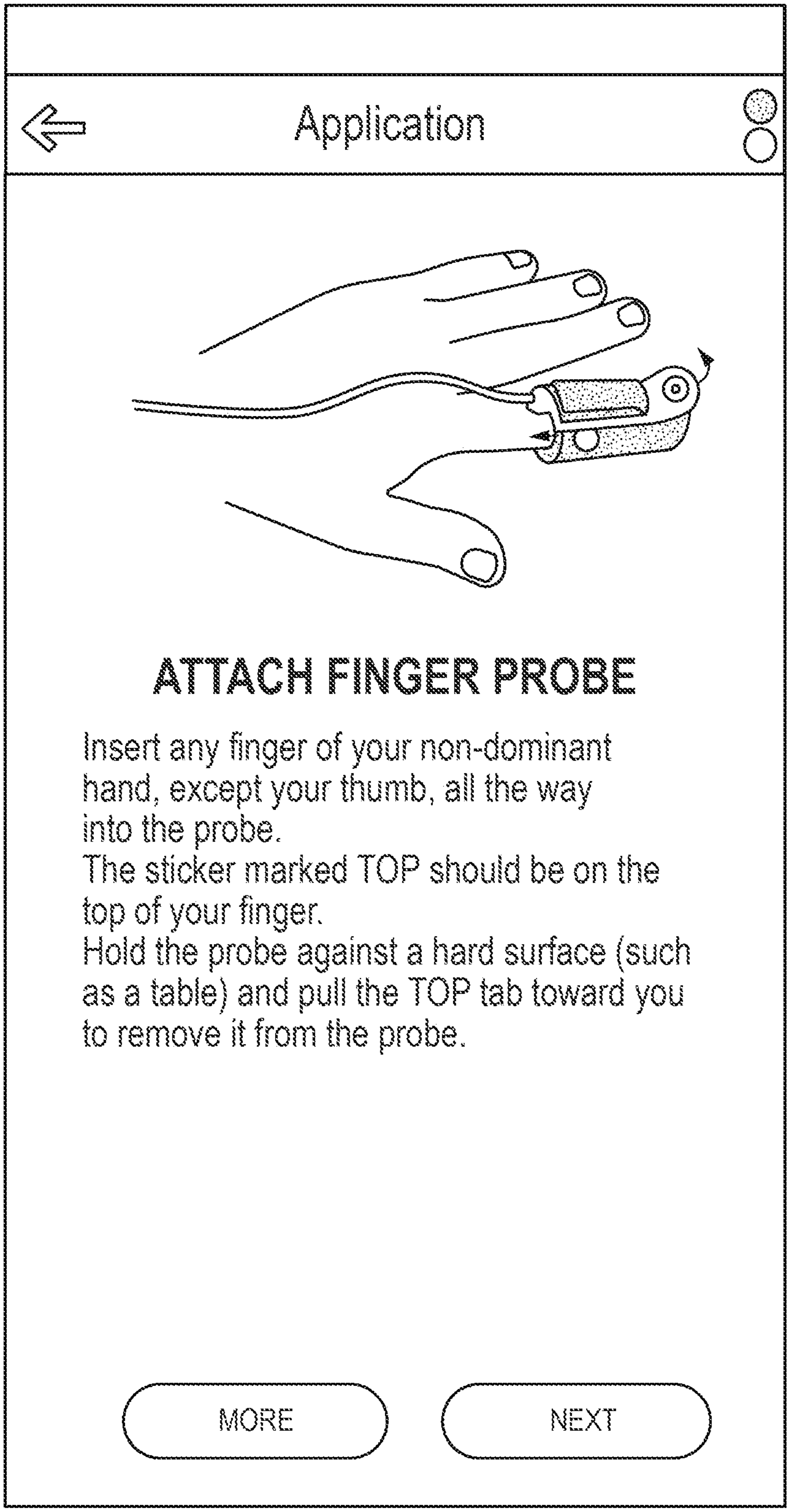
Figure 19E:
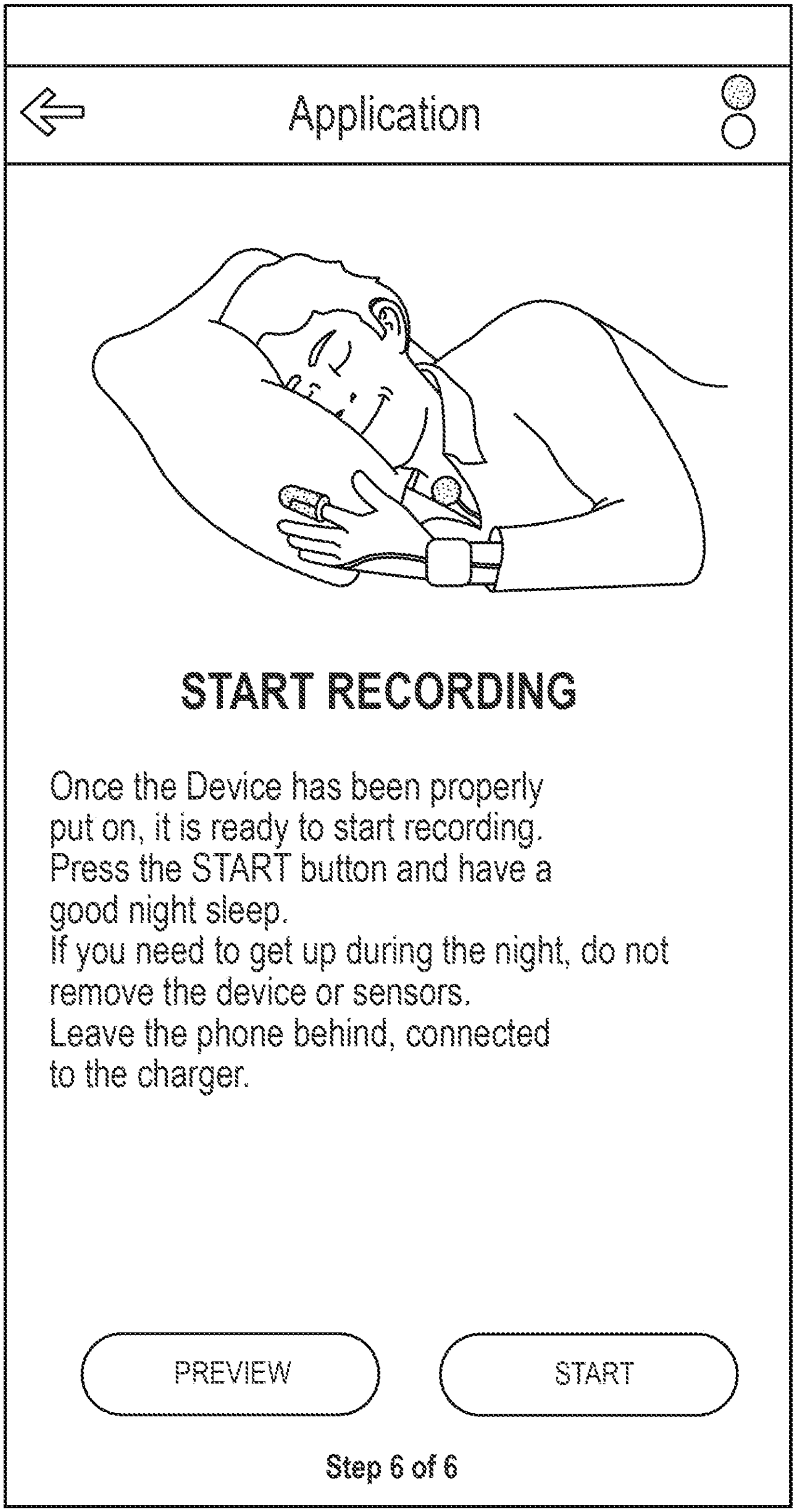
Figure 19F:
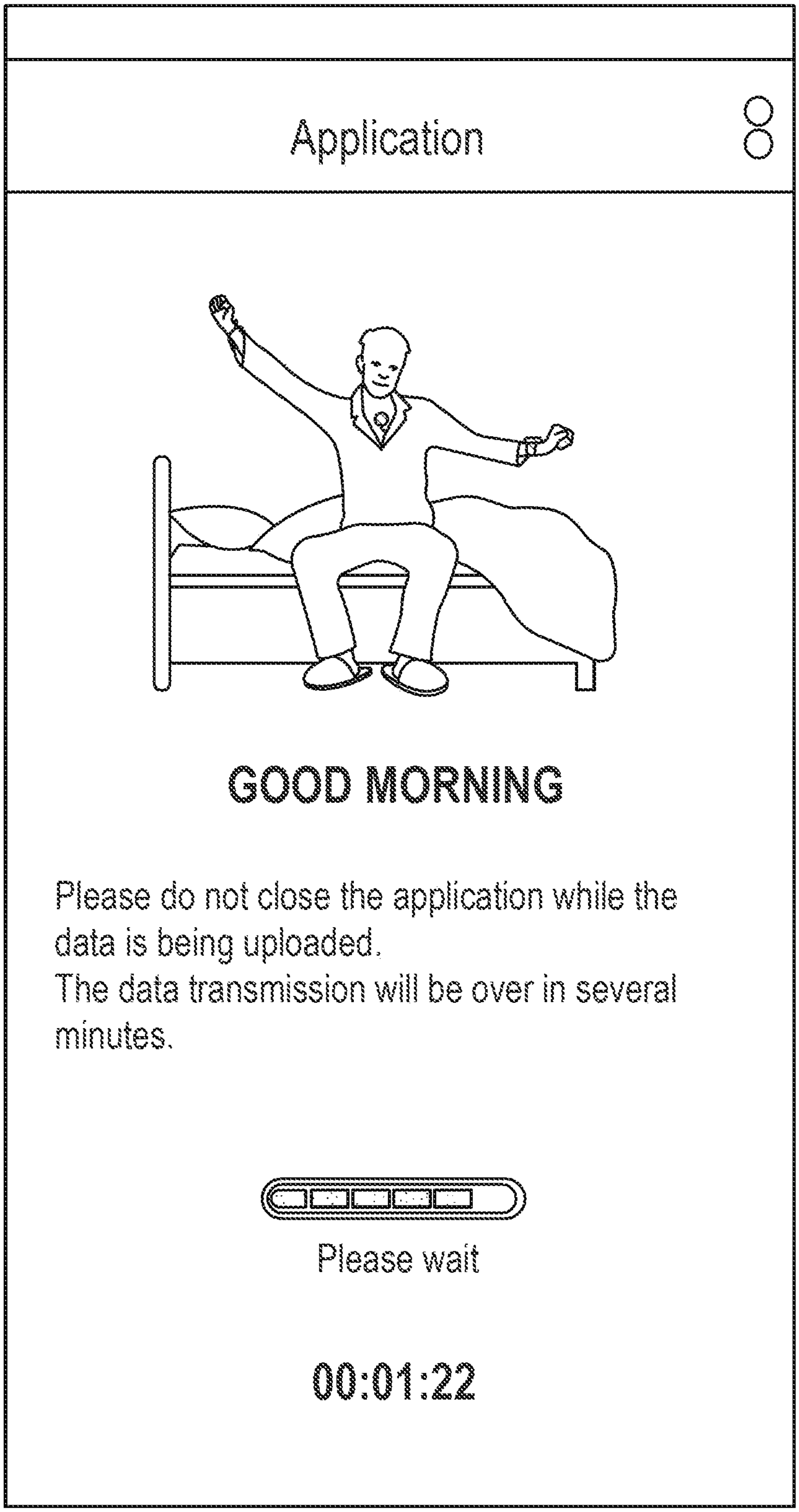

FIGS. 19A-19F depict screen shots of an application running on a mobile device, and describe an example method of conducting a sleep study. First, as shown in FIG. 19A, a patient may be informed that data from the sleep study may be sent to the patient's physician. In this example, in order to proceed with the sleep study, the patient may be instructed to turn off any other transmitting device(s) such as smart watches, other mobile devices, or headphones that may interfere with the sleep study, and when the patient is ready, to depress a "ready" button on the patient's mobile device. Second, as shown in FIG. 19B, the patient may be instructed to attach a component of a wearable device to themselves (e.g., a wrist device (e.g., the wrist device 1510 of wearable device 1500, etc.)) to the patient's non-dominant hand and secure the wrist device to the patient's wrist, etc.). Then, when the patient is ready to proceed, the patient may be instructed to depress a "next" button on the mobile device. Third, as shown in FIG. 19C, if the wearable device for the sleep study includes another component, the patient may be instructed to attach the another component of the wearable device to themselves (e.g., a chest sensor (e.g., the chest sensor 1530 of the wearable device 1500, etc.) to a center of the upper chest bone, just under the sternal notch, etc.) and to depress a "next" button on the mobile device. Fourth, as shown in FIG. 19D, if the wearable device for the sleep study includes still another component, the patient may be instructed to attach the still another component of the wearable device to themselves (e.g., a finger probe (e.g., the finger probe 1520 of the wearable device 1500, etc.) to any finger of the patient's non-dominant hand, except the thumb, by inserting the finger all the way into the finger probe, etc.) and to depress a "next" on the mobile device. Fifth, as shown in FIG. 19E, once the wearable device is properly worn by the patient, the patient may be instructed to depress a "start" button so that the wearable device will begin recording data. Finally, as shown in FIG. 19F, once the patient awakens the next morning, the patient is instructed to await data transmission before closing the application.

In some embodiments, physiological data may include at least one of heart rate data, oxygen saturation data, actigraphy data, snoring data, chest motion data, body position data, arm position data, sleep stage data, any combination thereof, and/or the like. For example, body position data may include at least one of supine, prone, recumbent, lateral recumbent, right lateral recumbent, left lateral recumbent, fowler's, Trendelenburg, any combination thereof, and/or the like. For example, arm position data may include inner wrist facing up, inner wrist facing down, inner wrist facing sideways, and/or the like. Additionally or alternatively arm position data may include at least one of both arms elevated (e.g., alongside head), right arm elevated, left arm elevated, both arms down (e.g., at patient's side), right arm down, left arm down, both arms crossed in front of chest, right arm in front of chest, left arm in front of chest, both arms crossed in front of abdomen, right arm in front of abdomen, left arm in front of abdomen, both arms crossed in front of pelvis, right arm in front of pelvis, left arm in front of pelvis, both arms behind back, right arm behind back, left arm behind back, any combination thereof, and/or the like. For example, sleep stage data may include at least one of awake, asleep, rapid eye movement (REM) sleep, non-REM sleep, light sleep, deep sleep, any combination thereof, and/or the like.

In some embodiments, physiological data may include at least one of oxygen saturation data, oxygen saturation data in combination with body position data, oxygen saturation data in combination with at least one of body position data or arm position data, any combination thereof, and/or the like.

In some embodiments, a uniform pressure field may be static and/or may prevent pooling of venous blood in the distal end of a finger while allowing pulsatile blood delivered by the arteries to be returned via the veins. In some embodiments, the pressure applied by the uniform pressure field may be sufficient to prevent free venous flow due to, for example, hydrostatic pressure and shock waves, while allowing the veins to carry blood delivered by the arteries out of the finger. In some embodiments, the pressure required to prevent venous pooling may differ from patient to patient.

In some embodiments, noise reduction (e.g., improved signal to noise ratio) in the peripheral arterial tone measurement may be achieved by applying sufficient pressure to partially unload, but not occlude, the wall tension of the arteries in the finger, when the finger is near heart level. This may allow the arterial wall to move freely to accommodate the pulsatile blood delivery of the heart. The applied pressure may be slightly above the maximum pressure in the veins when the hand is fully lowered (e.g., 5% higher and/or the like).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, computer program product, article, material, kit, and/or method described herein. In addition, any combination of two or more such features, systems, computer program products, articles, materials, kits, and/or methods, if such features, systems, computer program products, articles, materials, kits, and/or methods are not mutually inconsistent, is included within the inventive scope of the present disclosure. Embodiments disclosed herein may also be combined with one or more features, as well as complete systems, computer program products, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A programming system for initializing an uninitialized home sleep apnea medical device, the system comprising:

an external programming device configured to initialize the uninitialized home sleep apnea medical device, wherein the external programming device comprises at least one processor and computer-readable memory comprising instructions that when executed by the at least one processor cause the at least one processor to transmit a voltage-based index value through a wired connection to the uninitialized home sleep apnea medical device, wherein the voltage-based index value identifies the external programming device; and establish a wireless connection between the external programming device and the uninitialized home sleep apnea medical device based on the voltage-based index value.

2. The programming system of claim 1, wherein the uninitialized home sleep apnea medical device comprises a sleep apnea diagnostic device comprising a finger probe configured to secure to a finger of a patient.

3. The programming system of claim 2, wherein the sleep apnea diagnostic device is configured to apply a substantially uniform subdiastolic pressure to the finger of the patient while sensing an arterial pulse as a peripheral arterial signal of the patient.

4. The programming system of claim 2, wherein the sleep apnea diagnostic device further comprises a wrist-worn device having wireless communications circuitry and at least one processor coupled to a non-volatile memory.

5. The programming system of claim 2, wherein the sleep apnea diagnostic device further comprises a chest motion sensor configured for placement on an upper chest area of the patient.

6. The programming system of claim 1, wherein the external programming device comprises index generation circuitry configured to generate the voltage-based index value for transmission through the wired connection as a voltage signal based on a predetermined input to the index generation circuitry.

7. The programming system of claim 6, wherein the index generation circuitry is configured to generate the voltage signal as varying voltages between two predefined voltage levels to encode the voltage-based index value in the voltage signal.

8. The programming system of claim 7, wherein the voltage-based index value is encoded in the voltage signal as a binary sequence of bits.

9. The programming system of claim 6, wherein the uninitialized home sleep apnea medical device comprises voltage receiving circuitry connected to a pair of electrical battery terminals and configured to receive the voltage signal, determine, based on the voltage signal, a binary sequence of bits, and store, in a buffer, the binary sequence of bits.

10. The programming system of claim 9, wherein the uninitialized home sleep apnea medical device further comprises at least one processor coupled to a memory, wherein the at least one processor is configured to read, from the buffer, the binary sequence of bits; and determine, based on the binary sequence of bits, the voltage-based index value that identifies the external programming device.

11. The programming system of claim 1, wherein the voltage-based index value uniquely identifies the external programming device among a plurality of external programming devices.

12. The programming system of claim 1, wherein the external programming device is configured to establish the wireless connection between the external programming device and the uninitialized home sleep apnea medical device based on the voltage-based index value in response to receiving a wireless connection request from the uninitialized home sleep apnea medical device, wherein the wireless connection request includes the voltage-based index value.

13. The programming system of claim 1, further comprising the uninitialized home sleep apnea medical device.

* * * * *